United States Patent [19]

Lehrer

[11] Patent Number: 5,609,597
[45] Date of Patent: Mar. 11, 1997

[54] APPARATUS AND METHOD OF EXTRACORPOREALLY APPLYING AND LOCKING LAPAROSCOPIC SUTURE AND LOOP LIGATURES

[76] Inventor: Theodor Lehrer, 936 Intracoastal Dr., Apt. 21C, Ft. Lauderdale, Fla. 33304

[21] Appl. No.: 433,627

[22] Filed: May 3, 1995

Related U.S. Application Data

[63] Continuation-in-part of Ser. No. 351,550, Dec. 7, 1994, which is a continuation of Ser. No. 164,462, Dec. 9, 1993, Pat. No. 5,536,273.

[51] Int. Cl.$^6$ .................................................. A61B 17/04
[52] U.S. Cl. .............................. 606/139; 606/144; 289/17
[58] Field of Search .................................... 606/139, 144, 606/148; 289/2, 17

[56] References Cited

U.S. PATENT DOCUMENTS

| | | | |
|---|---|---|---|
| 3,344,790 | 10/1967 | Dorner | 128/340 |
| 3,871,379 | 3/1975 | Clarke | 128/326 |
| 4,493,323 | 1/1985 | Albright et al. | 128/340 |
| 4,597,390 | 7/1986 | Mulhollan et al. | 128/340 |
| 4,614,187 | 9/1986 | Mulhollan et al. | 128/303 R |
| 4,760,848 | 8/1988 | Hasson | 128/340 |
| 4,945,920 | 8/1990 | Clossick | 128/751 |
| 5,015,250 | 5/1991 | Foster | 606/147 |
| 5,037,433 | 8/1991 | Wilk et al. | 606/139 |
| 5,129,912 | 7/1992 | Noda et al. | 606/139 |
| 5,147,373 | 9/1992 | Ferzli | 606/144 |
| 5,273,545 | 12/1993 | Hunt et al. | 604/167 |
| 5,275,611 | 6/1994 | Behl | 606/198 |
| 5,312,360 | 5/1994 | Behl | 604/164 |

OTHER PUBLICATIONS

Graumont & Hensel, *Encyclopedia of Knots and Fancy Ropework*, New York 1945, preface & pp. 11, 56, 99–101.

*Primary Examiner*—Gary Jackson
*Attorney, Agent, or Firm*—John C. Smith

[57] ABSTRACT

A suture applier instrument for tying suture and loop ligatures in laparoscopic excisional procedures such as LAVH, tubal ligation, salpingectomy, cophorectomy and appendectomy; in the repair of the fallopian tubes, uterus and ovaries; and in retropubic colposuspension using locking slip knots; and an efficient extracorporeal method to effectively lock them. The slip knot is held at the tip of the suture applier instrument and is kept in position on the target tissues while its two suture strands are operated extracorporeally, tying the loop ligature with one of the strands and locking or tightening the knot itself with the other. Additional hitch knots may be introduced and tied after the slip knot has been applied, using the same instrument. New knots, spool for pretied knot sutures and knot tying techniques for use with the suture applier are presented.

20 Claims, 31 Drawing Sheets

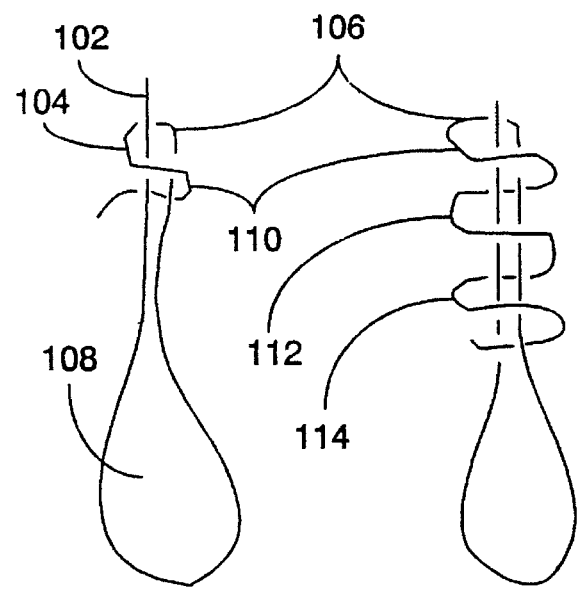
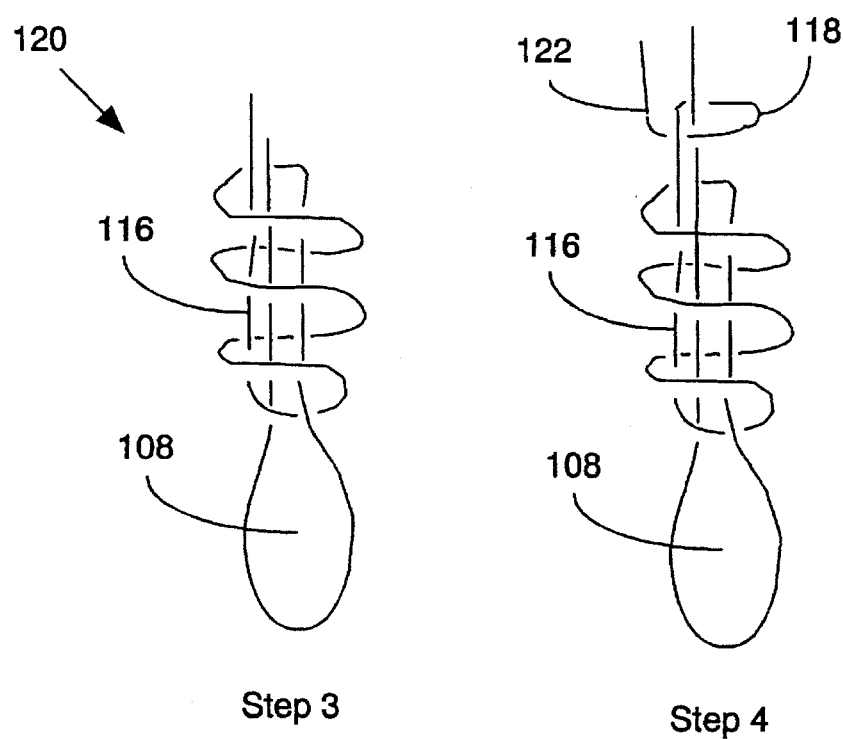
Figure 1

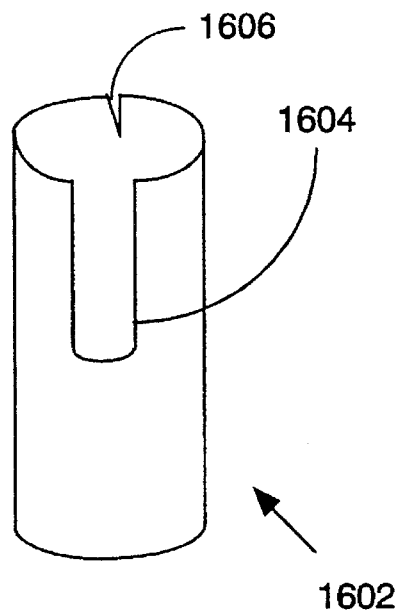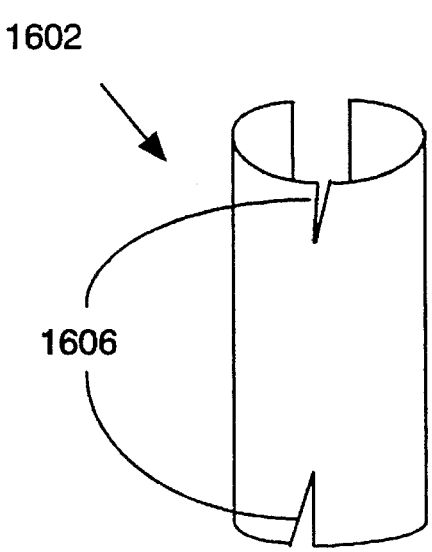
Figure 16A · Figure 16B
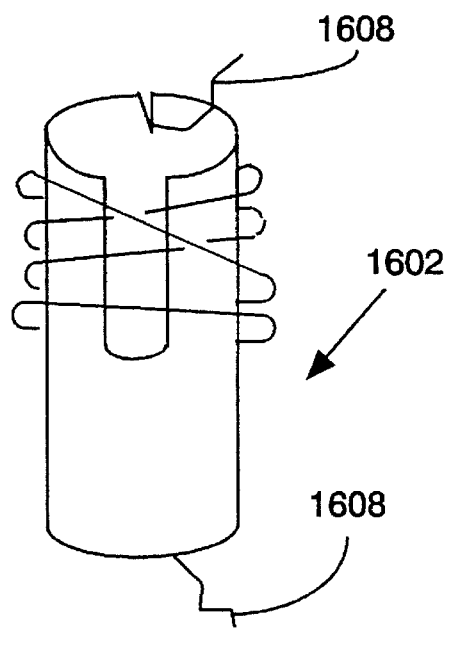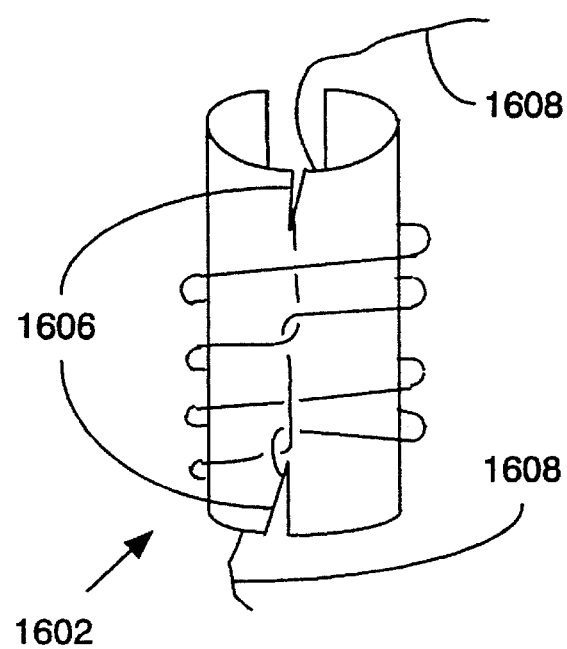
Figure 16C · Figure 16D

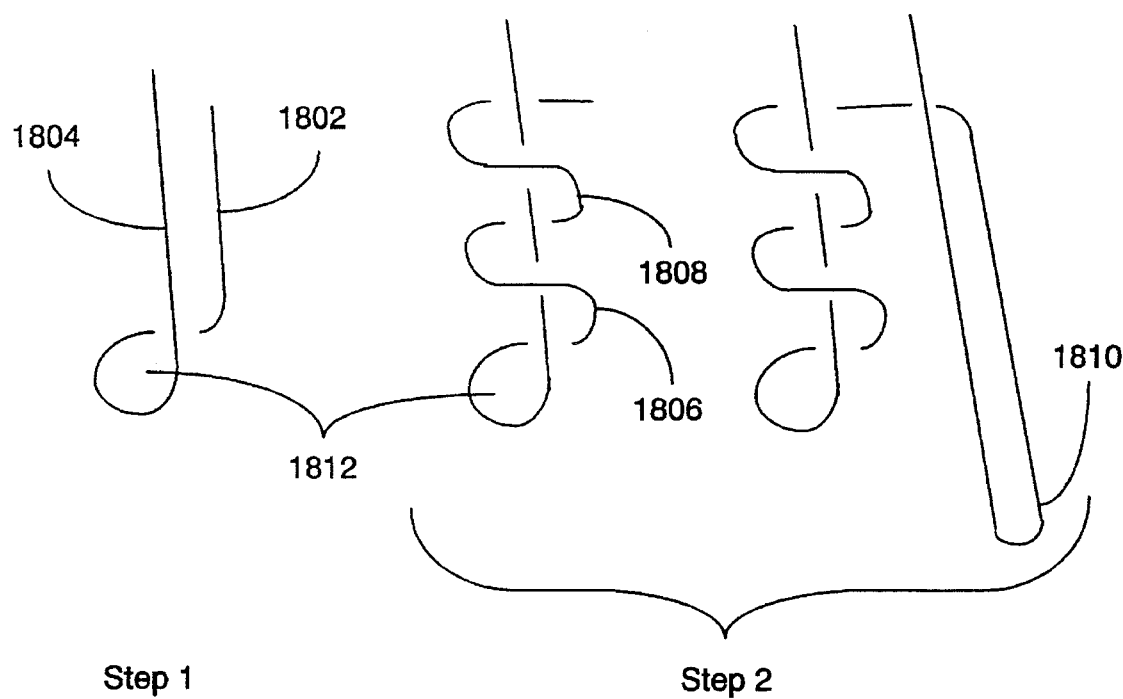
Step 1          Step 2
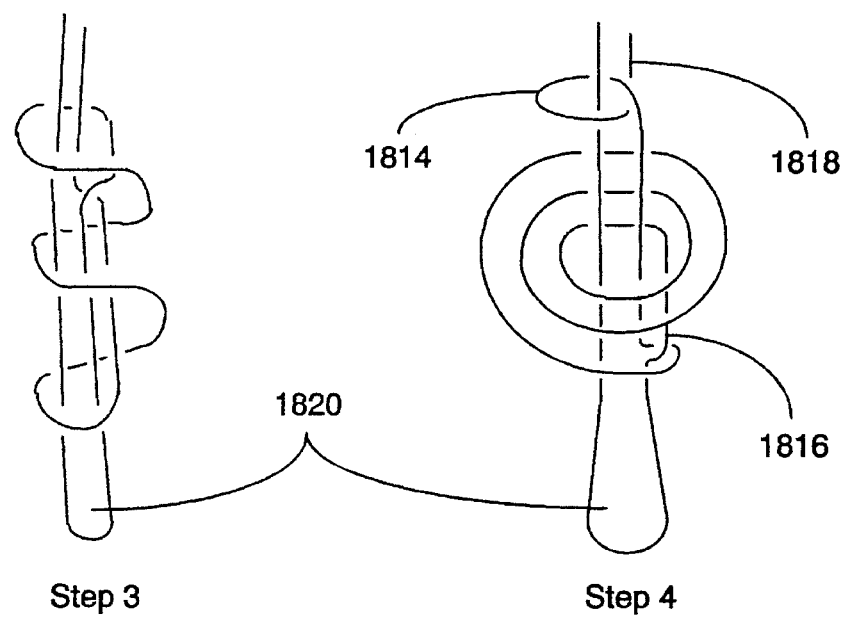
Step 3          Step 4
Figure 18

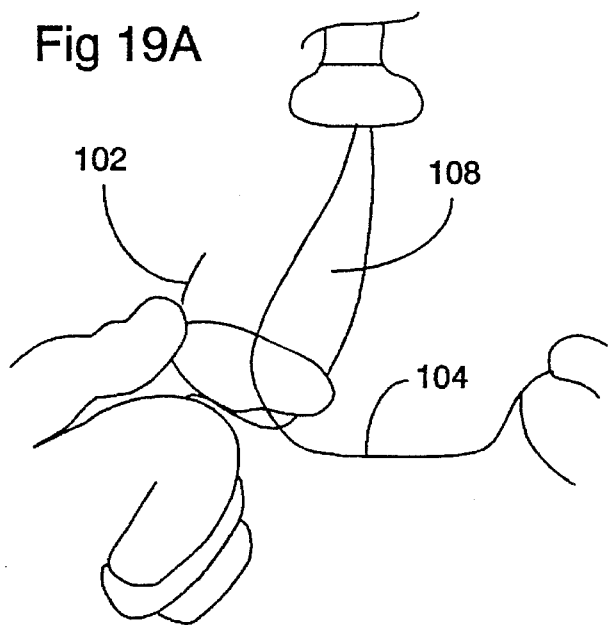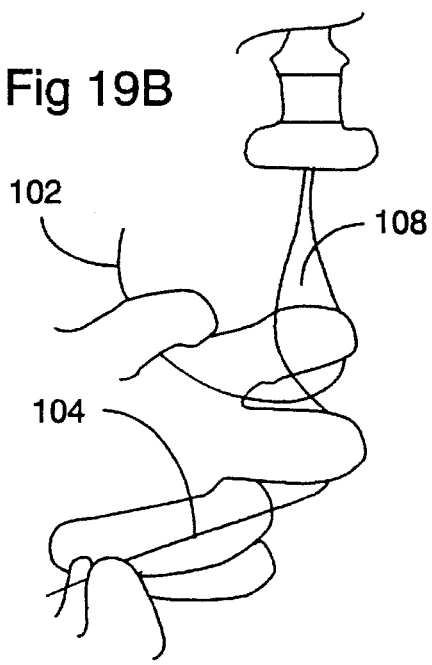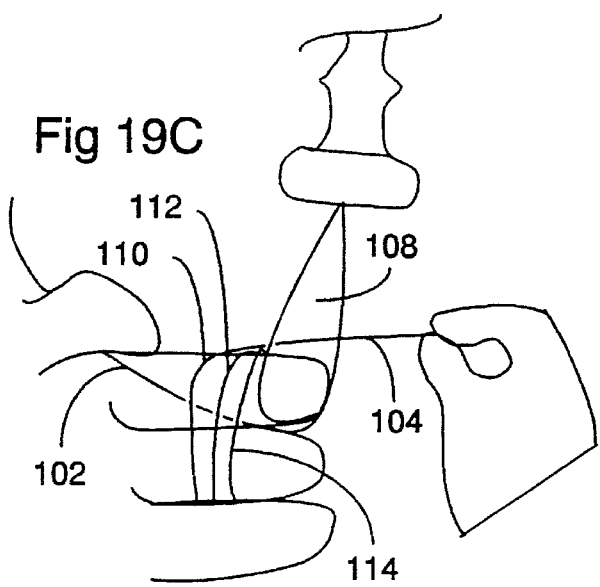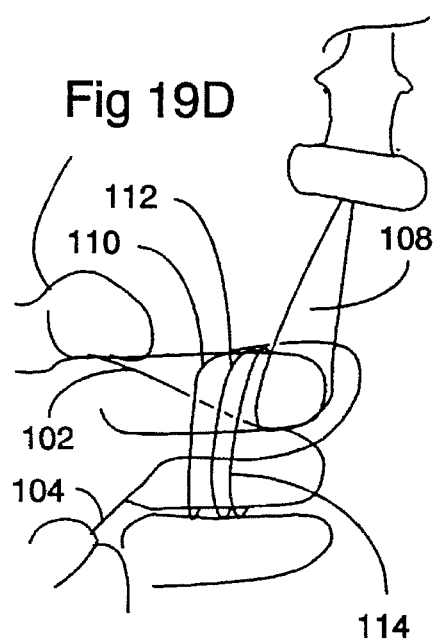
Figure 19

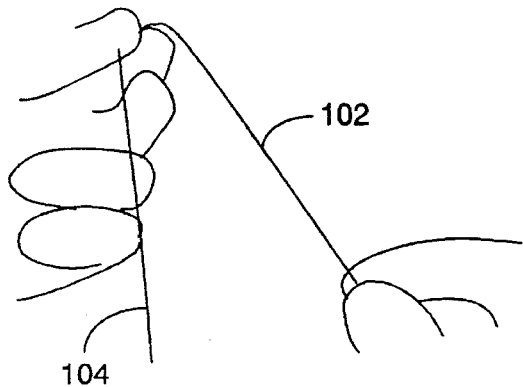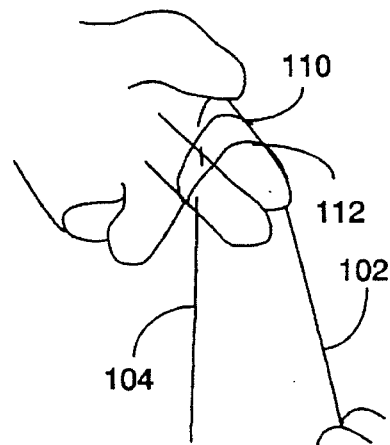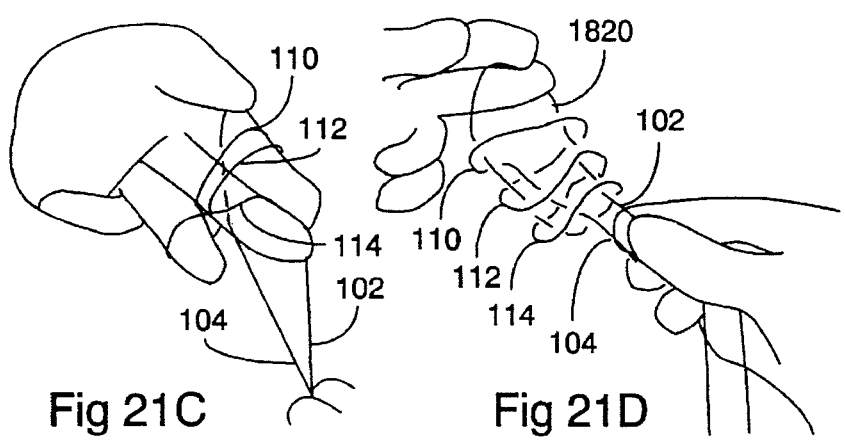
Figure 21

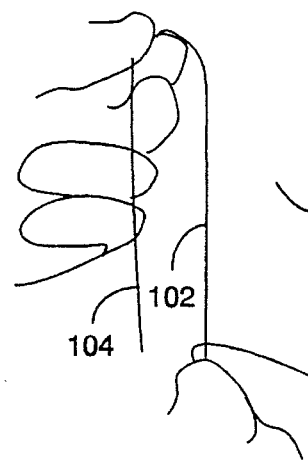
Fig 22A
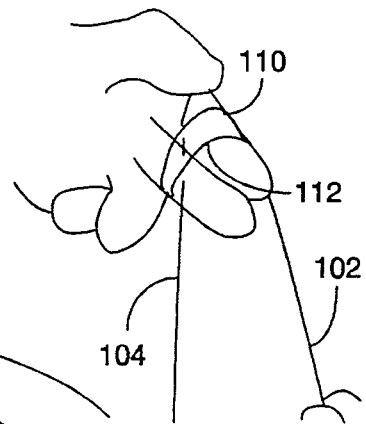
Fig 22B
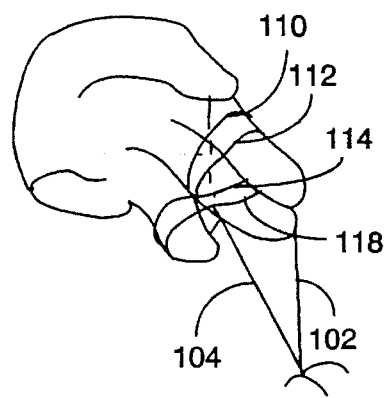
Fig 22C
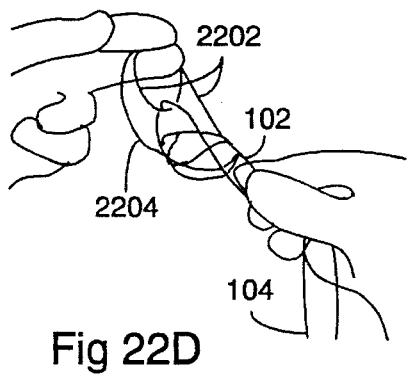
Fig 22D
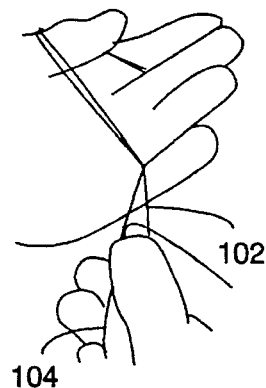
Fig 22E
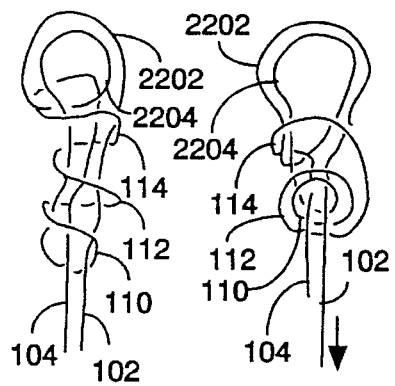
Fig 22F
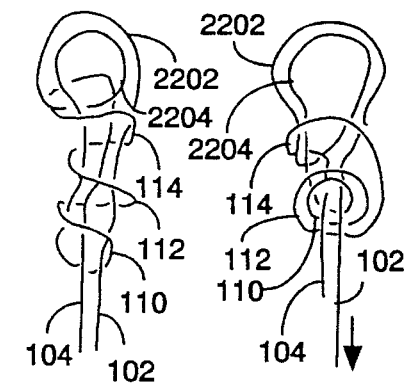
Fig 22G
Figure 22

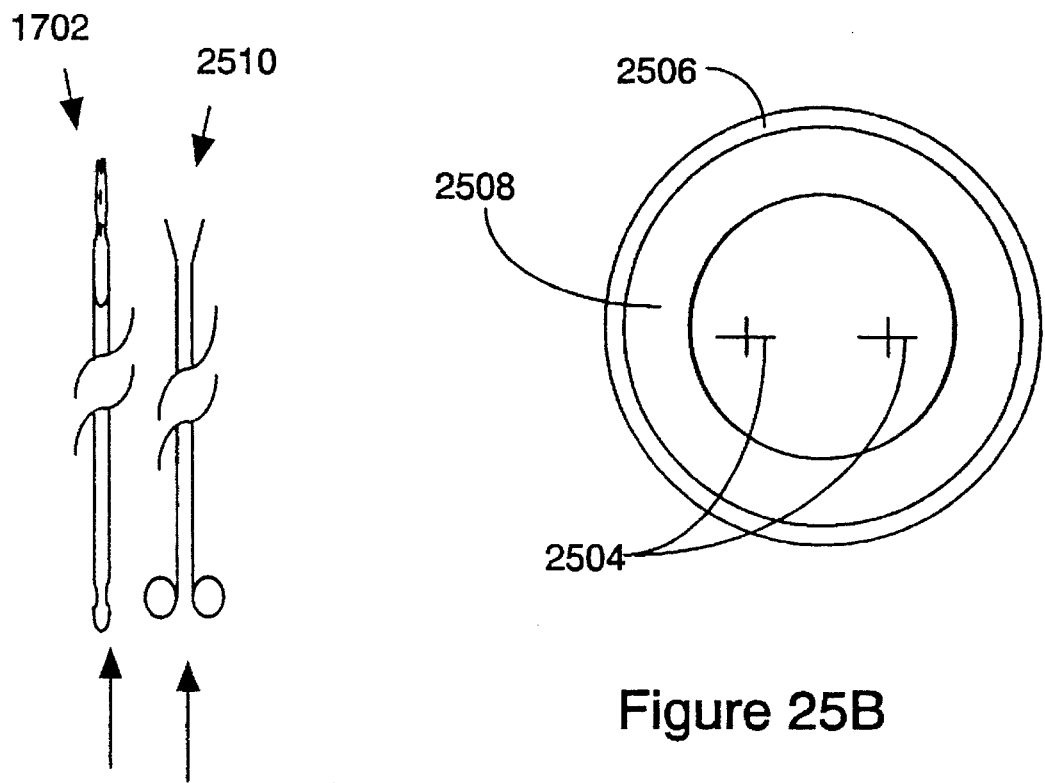
Figure 25B
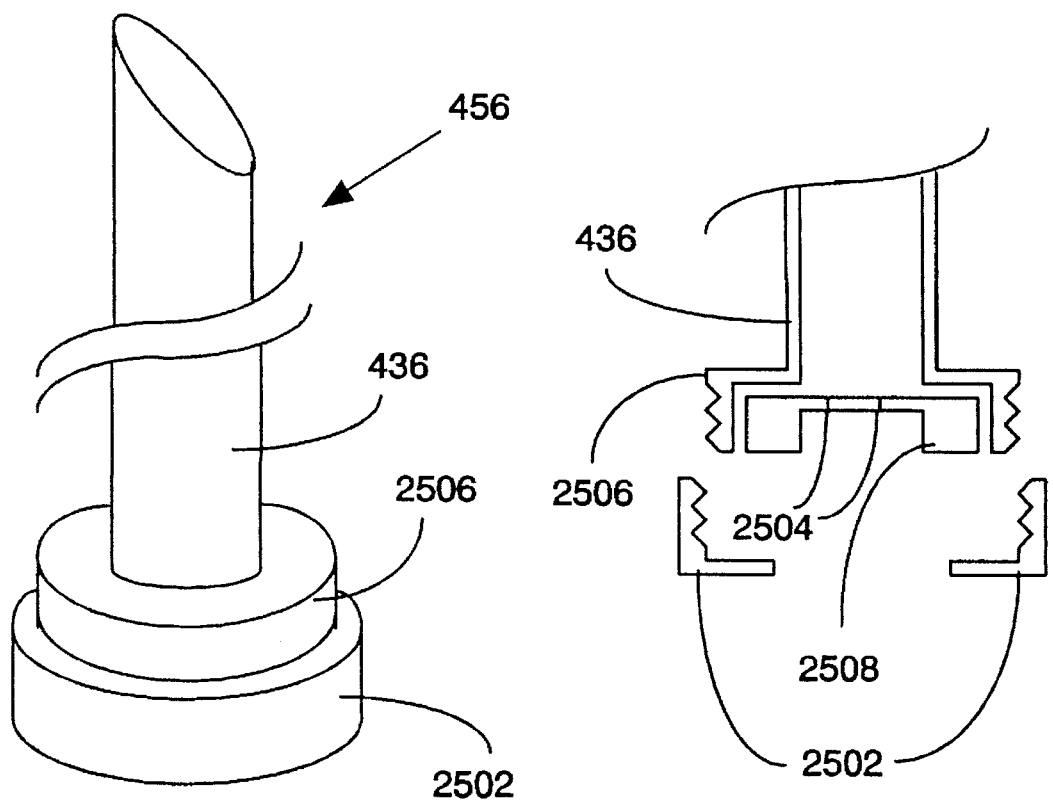
Figure 25A
Figure 25C

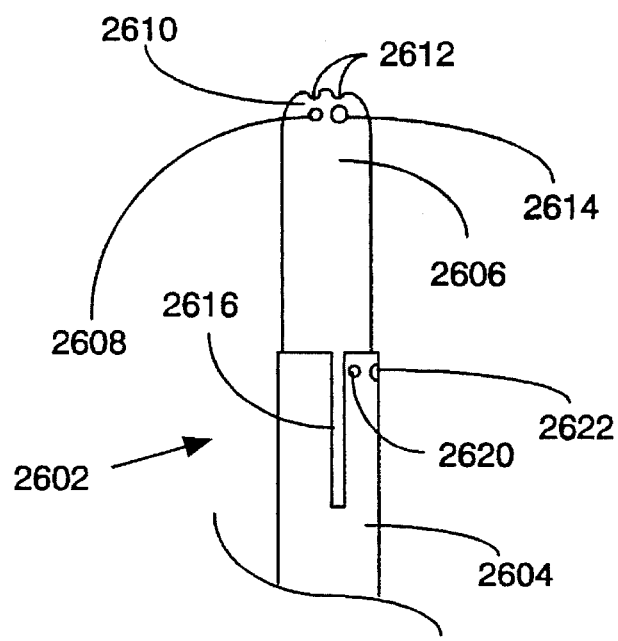
Figure 26A
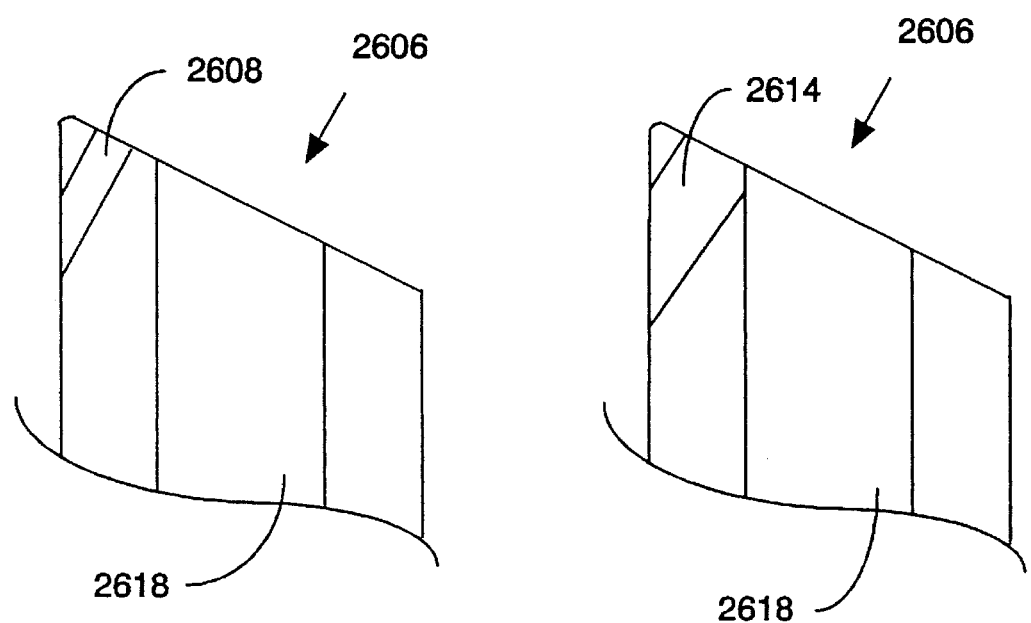
Figure 26B
Figure 26C

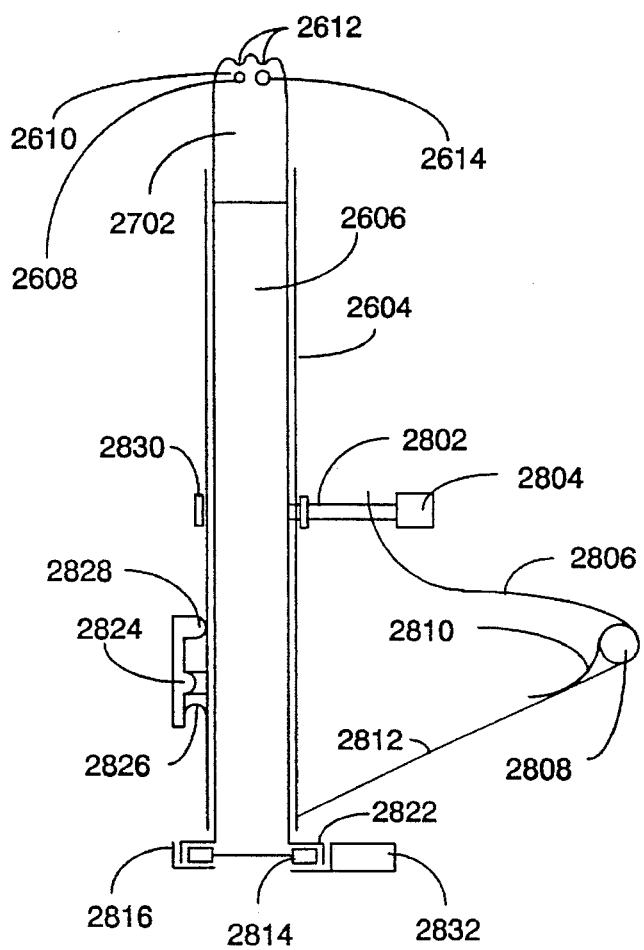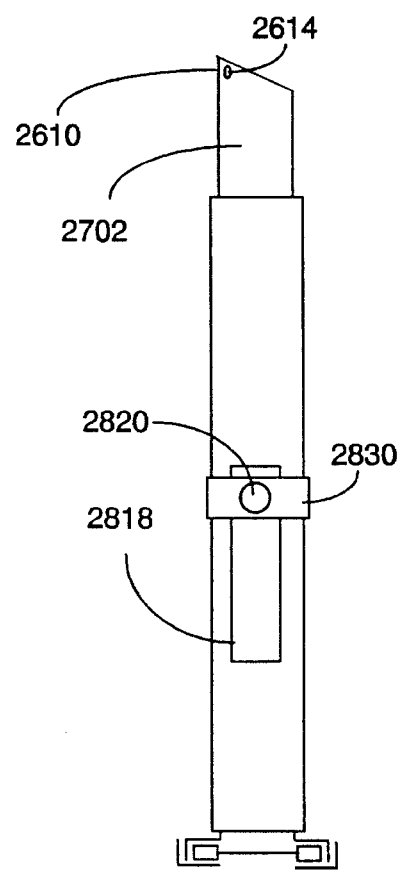
Figure 28A                    Figure 28B

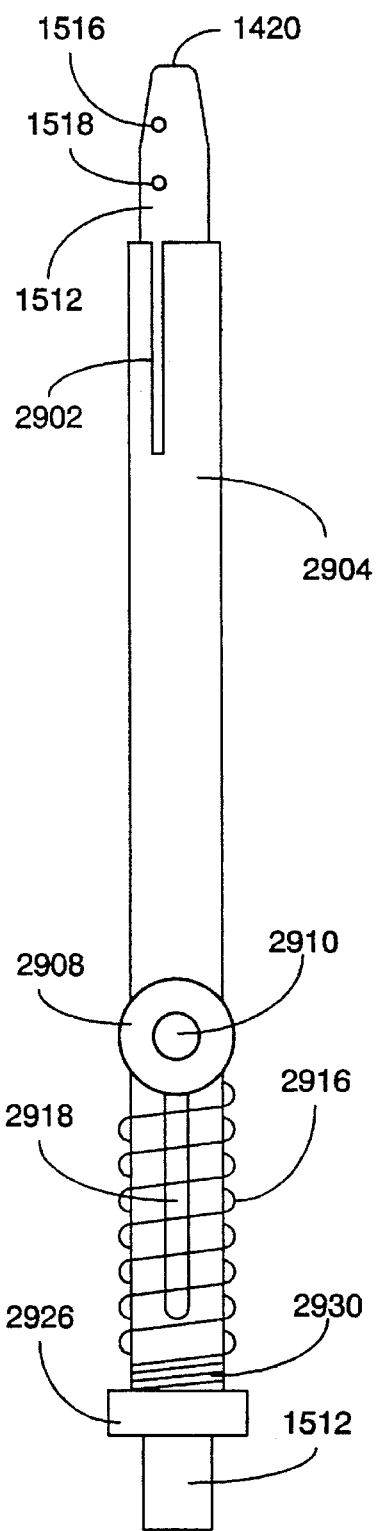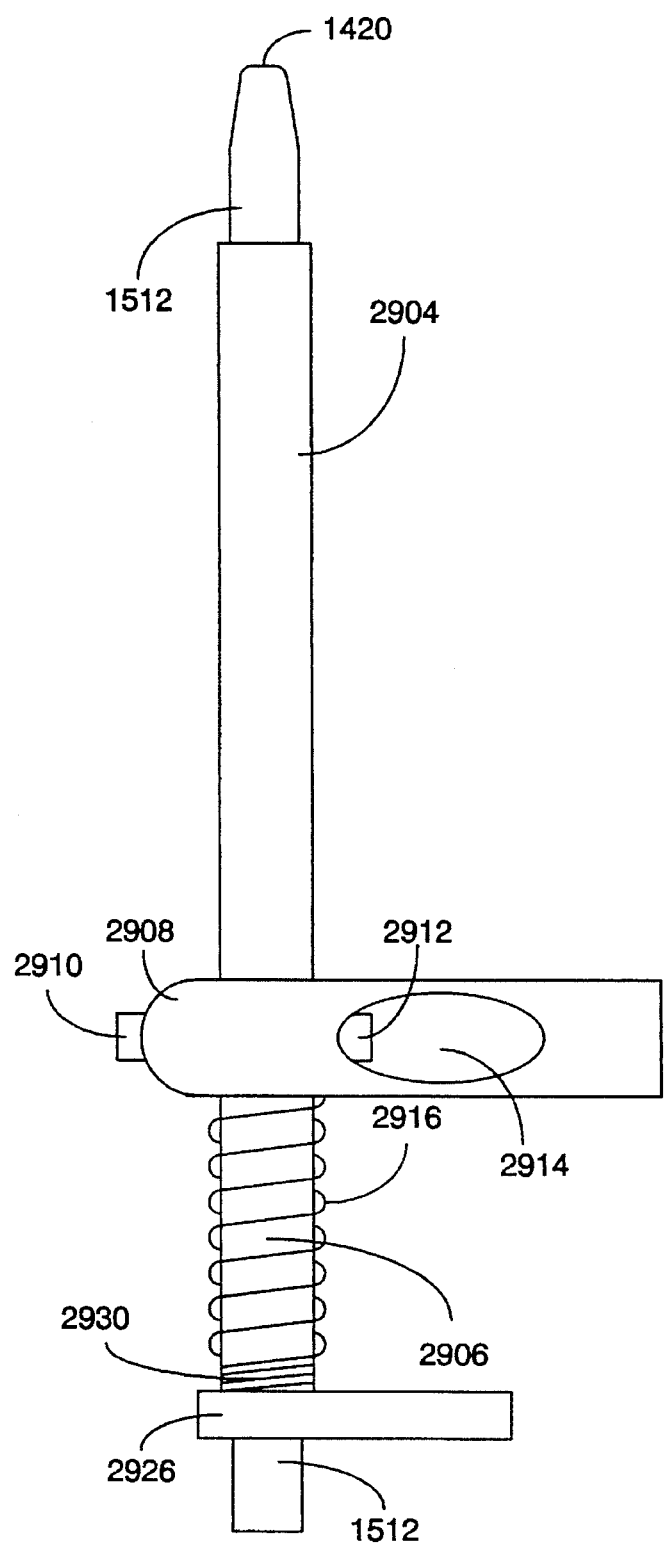
Figure 30A                    Figure 30B

APPARATUS AND METHOD OF EXTRACORPOREALLY APPLYING AND LOCKING LAPAROSCOPIC SUTURE AND LOOP LIGATURES

CROSS-REFERENCE TO RELATED APPLICATIONS

This is a continuation-in-part of the commonly owned copending application entitled "APPARATUS AND METHOD OF EXTRACORPOREALLY APPLYING AND LOCKING LAPAROSCOPIC SUTURE AND LOOP LIGATURES", filed Dec. 7, 1994, bearing U.S. Ser. No., 08/351,550 and naming Dr. Theodor Lehrer, the sole named inventor herein, as sole inventor, which was in turn a continuation of patent application entitled "APPARATUS AND METHOD OF EXTRACORPOREALLY APPLYING AND LOCKING LAPAROSCOPIC SUTURE AND LOOP LIGATURES", filed Dec. 9, 1993 bearing U.S. Ser. No., 08/164,462, now U.S. Pat. No. 5,536,273, and naming Dr. Theodor Lehrer, the sole named inventor herein, as sole inventor, the contents of which is specifically incorporated by reference herein in their entirety.

TECHNICAL FIELD

The present invention relates to surgical instruments. In particular, instruments used for the extracorporeal application of non-locking and locking slip knots to endoscopic suture and loop ligatures.

BACKGROUND ART

A wide variety of endoscopic surgical techniques for securing tissue has been developed. In addition to the suture and loop ligature methods which are the subject matter of this invention, alternative techniques to the suture and/or ligature method include the use of mechanical devices such as staples, silastic rings and clips, automatic stapling devices, electrosurgery and lasers. A high proportion of endoscopic surgeons experience difficulty in acquiring and maintaining proficiency in their use. These alternate techniques are costlier and may be associated with technical problems, more extensive tissue damage and other surgical complications.

While great advances have been made to improve them over time, improvements in endoscopic suture and loop ligatures are highly desirable because this is the preferred technique in open surgery, which is the standard for operative laparoscopy. Surgeons have mastered the suture method in open surgery and have trusted it over many years to be the most reliable and cost effective technique.

The suture method is superior at repairing organs after portions have been excised from them. For instance, as in a myomectomy procedure, the uterus can be restored. Further, in LAVH, the support of the vaginal vault can be restored to prevent vaginal prolapse by suturing it to the uterosacral ligaments. In tubal reconstructive surgery, the patency of the fallopian tube can be best restored with suturing techniques. Procedures to elevate the bladder and correct urinary incontinence are likewise best done with the suture method.

Suturing is a superior technique to effect hemostasis, particularly of large blood vessels such as the uterine vessels and ovarian artery and vein. The laparoscopic dissection to skeletonize these vessels is important to safely apply any of the methods of hemostasis. Suturing provides precision in handling the tissues, which is often required when operating in areas where the bowel, ureter, or other structures may be dangerously close to the operative site, particularly in cases where the anatomy has been distorted by adhesions, tumors, endometriosis, or inflammation.

Automatic gun staplers are too wide and rigid in shape, and may lack the precision that is required on the aforementioned surgical conditions.

In this regard, the problem with electrosurgery is the so called "field effect" that is produced by the spread of heat, which destroys a wider sector of tissues around the target. The damage to the tissues is partially invisible to the naked eye and may interfere with the reparative process. When used to effect hemostasis of large vessels, electrosurgery frequently causes extensive tissue damage.

Another example of the more extensive tissue damage of electrosurgery as compared to sutures is in tubal ligation. For electrosurgery to be effective and reliable, the surgeon must completely coagulate at least three centimeters of the tube. With the suture method, only one centimeter of the tube is taken out, which is advantageous in the event that the patient requires a tubal reanastomosis to be performed in the future. An additional advantage is that a specimen is obtained that can be examined histologically.

Silastic rings may slip off the fallopian tube, producing a failed tubal ligation.

Securing surgical ties is standard practice in open laparotomy surgery. In this form of surgery, the surgeon has wide and direct access to the operative site and can secure surgical ties with relative ease. As a result, the surgeon in this type of operative environment has great flexibility in how ligatures are applied and secured.

While this provides advantages to both the surgeon and patient, there are also serious drawbacks to this type of surgery. In particular, the size of the incision required to effect access by the surgeon creates scarring which may be of significant concern to the patient. In addition, larger incisions create larger areas which not only are injured by the incision and require greater effort to heal, but also create more potential areas of infection, more post operatory pain, and more respiratory, urinary, and gastrointestinal difficulties that may prolong the convalescence period.

One solution to these problems has been provided by the development of laparoendoscopic surgery. In this type of surgery, an illuminated tubular instrument, a laparoscope, is passed through a puncture wound in the abdomen. The laparoscope typically is used not only for examinations, but also for a variety of surgical procedures (e.g., tubal ligations, removal of tumors of the ovaries or uterus, etc.). One of the principle advantages of a laparoscope is the reduced size of the incision required to effect the surgery. Further, depending on the surgical procedure being performed, residual scarring may effectively be reduced, as well as post operatory complications. The foregoing advantages mean that hospital stays may be reduced and/or eliminated, making outpatient ambulatory surgery possible. The cost of surgery may be therefore lower and full recovery faster.

While prior approaches to laparoscopic surgery have produced the aforementioned benefits to patients, they have had an adverse effect on the surgeons flexibility in adequately applying available suturing techniques for a given situation. In particular, the limited use of the suture method in laparoendoscopic surgery is due to the difficulties that surgeons currently encounter in locking their ties.

The Surgeon's Knot and/or hitch knots are well known in the art and are the type of knots most frequently used in operative laparoscopy, but these knots have a tendency to loosen up before a second throw can be made, which may render the tie ineffective. In comparison, slip knots have better slipping strength. Non-locking slip knots have less slippage power than self locking slip knots. This difference in slippage power increases after the noose is tied proportionally to the force applied on the standing part suture that closes it. Prior art ligator devices have been developed which use slip knots. The slip knots currently in use in commercially available loop ligature and suture ligature kits are the Roeder loop, and the Duncan loop. Both of these knot types are well known in the art. The problem with using the Roeder loop, and to a lesser degree the Duncan loop, is that they are not effectively locked and the tie needs to be secured with an additional knot.

Another problem associated with the design used for these slip knots is that the manufacturers typically trim the end suture strand too short (i.e., very close to the knot). As a result, the noose of the slip knots can be tightened but not the knot itself, because the end portion of the suture is too short to be used for cinching the knot to tighten it. For this reason, the surgeon cannot restore the loss of slippage power of the knot that occurs when the noose is applied on the tissues. In addition, the slip knots cannot be effectively locked without pulling the end portion of the suture against the knot. Therefore, the prior art Roeder and Duncan loops whose end portions are trimmed will remain unlocked on the tissues.

Non-locking slip knots have less slippage power than self locking slip knots, which if woven too tightly may frequently get accidentally locked and may jam the noose. This problem of self locking slip knots may be avoided if the knot used is loosely woven. However, this requires that the knot be cinched with the end portion suture to tighten and lock it, after the noose has been closed on the target tissues. Self locking slip knots cannot be effectively locked without cinching the knot with the end portion of the suture. Therefore, the prior art loop ligatures, the prior art pretied knot sutures, and the prior art pretied loop sutures whose end portions strands are trimmed can not effectively use self locking slip knots and need to be secured with one or more additional knots.

An example of this slippage is shown in study by Hay et al (Hay DL, Levine RL, von Fraunhofer JA, Masterson BJ. Chromic gut pelviscopic loop ligature: Effect of the number of pulls on the tensile strength. J Reprod Med 1990,35:260–2) (hereinafter, Hay). The slippage power decreases after the noose of the knot is tied, and the decrease in slippage power is proportional to the force applied on the standing part suture that closes it. In this study, it was demonstrated under laboratory conditions that with a commonly known knot called the Roeder loop, the least slippages occurred when only one pull was used to apply the loop ligature. In the study, two out of five loop ligatures had slippage with one pull. However, the slippage rate increased with each additional pull to three out of five; and to four out of five loop ligatures tested.

This problem is more apparent when newer materials, such as polyglactin (Vicryl Dexon), polydioxanone (PDS) or poliglecaprone (Monocryl) are used. These suture materials have comparatively less slippage power than catgut. However, catgut is a highly reactive material which is being replaced. The advantage of the newer materials is that they cause less foreign body inflammatory reaction and may be potentially better than catgut, provided that the suture or loop ligature is properly secured.

In addition to the problem discussed above (i.e., the inability of prior art knots to tighten the knot itself, and then lock the knot due to the excessively trimmed end portion of the suture), the excessively short end suture strand also precludes locking the slip knot with an additional security knot. To compensate for this potential problem, Hunt advises using three loop ligatures to tie pedicles such as a fallopian tube (Hunt R. Atlas of Female Infertility Surgery, Second Edition, 1992 Mosby Year Book. Page 264–267). These multiple ligatures are not locked. Of course, each ligature increases the devascularization of tissue and inflicts some tissue damage when applied. This brings about an increase of inflammation secondary to the resorption of devitalized tissue that must be eliminated and a foreign body inflammatory reaction to the excess suture material, with the possibility of adhesions and of secondary intestinal obstruction. Therefore, the application of three ligatures may result in some additional damage to the ligated tissue and other intraperitoneal organs.

Surgeons would prefer to avoid using multiple ligatures as long as they can rely on the fewer ligatures remaining securely tied. If a single tie is properly locked, as in open surgery, the surgeons seldom feel the necessity to add multiple ligatures on a single pedicle. Unless ligature manufacturers stop trimming the end of the suture, surgeons need to make their own suture and loop ligatures, leaving enough length of end suture to add a security knot using either an intracorporeal or extracorporeal tying technique. Intracorporeal tying techniques are difficult to master to a degree comparable to open surgery, and can be quite time consuming to perform. Making the knot intracorporeally, and tying it with the appropriate tension is more difficult and time consuming to the surgeon which in turn creates higher cost to the patient. Further, the reduced efficiency of the surgeon and the increase in time taken to complete the surgery means that the patient is exposed for a longer period of time to the stress of surgery and anesthesia and increases the cost of surgery. This may in turn negate in part the benefits of laparoscopic surgery and create a logistical problem for busy surgical facilities and personnel in terms of manpower efficiency which also increases patient costs.

Therefore, this intracorporeal knot technique, while addressing some of the problems caused by slippage, has drawbacks which create both economic inefficiencies and health risk, both of which will ultimately be borne by the patient. Extracorporeal knot tying is more efficient and easier for the surgeon to master. By enabling the surgeon to more quickly complete the surgery, the patient is spared the aforementioned potential problems of intracorporeal knot tying.

The prior art has not recognized that leaving both suture strands sufficiently long to span the distance from the target tissues to the outside makes it possible to extracorporeally tighten slip knots and restore the slippage power; and to lock a self locking slip knot. In addition, it provides the endoscopic surgeon the ability to secure the loop ligature with extracorporeal knots, as in open surgery, avoiding the necessity of using multiple ligatures on a single pedicle.

The use of slip knot for suture ligatures has the additional problem of the "sawing effect" in which the suture that is passed through the tissues slides against the tissues and damages them much like a rope can damage the skin of the hands holding it. Those skilled in the art will recognize that the sawing effect only applies to suture ligatures. In a loop ligature, the suture material surrounds the tissue and, therefore, will not saw through it. One known technique that takes advantage of the superior holding power of a slip knot and can decrease the sawing effect that a slip knot may produce upon initial tightening is to first pass the suture needle that is attached at the end of one of the suture strands of the slip knot, first through the tissues that are being suture ligated, and then through the noose of the slip knot that has been introduced into the peritoneal cavity together with the suture needle. In this needle-thru-noose technique, the suture needle may be placed on the suture strand that controls the closure of the noose, which is called the "standing part", or similarly, the suture needle may be placed on the other suture strand, which is called the "end portion".

The first approach, introduced by Hasson HM (Suture loop techniques to facilitate microsurgical and laparoscopic procedures. J Reprod Med 32(10):765–7, 1987 Oct), is not commercially available. The second approach of the loop suture technique was introduced by Noda (Noda WN, Lubock P. Device and Method for Applying Suture. United States Patent. U.S. Pat. No. 5,129,912 Date of Patent Jul. 14, 1992) and is used in the Laparomed Suture Applier and in the pretied loop sutures that are manufactured by Ethicon and US Surgical Corporation.

These two approaches are useful, but limited because their ties remain unlocked. In addition, the ready made suture kits using these two approaches have a limited availability of suture materials and needle sizes.

The same can be said of the pretied suture method that is commercially available as the "Pretied Endoknot Suture" from Ethicon, Inc., in which a slip knot is applied directly on the target tissues instead of tying the tissues with a secondary noose. This method consists of a suture needle that is attached to the standing part and is passed first through the tissue and then through the noose of a wire guide which is then pulled back passing the standing part into the lumen of the tubular ligator and out through the proximal opening of the tubular ligator. The loops of the knot, that are pretied around the shaft of the tubular ligator are then advanced over its distal end to form a knot. This pretied method of the prior art can save time and avoid errors when fashioning the knots. However, since the knot is completed extracorporeally and then reintroduced, the large noose that extends from the knot to the target tissues requires more suture material to pass under tension through the tissues. This represents no advantage in terms of the sawing effect on tissues upon initial tightening of the slip knot when compared to prior art methods of fashioning and/or delivering an extracorporeal slip knot.

Thus, the drawback to the Pretied Endoknot Suture technique is that the knot must be completed outside the peritoneal cavity and then reintroduced. The large resulting noose extends from the outside to the target tissues which therefore requires more suture material to pass through the tissues, under tension, producing the so called "sawing effect." The large size of the noose creates more trauma to the tissue as more suture material is passed through it to close the noose as compared to the small size noose of an intracorporeal knot.

While the prior art has addressed many of the problems associated with ligature application, it has failed to provide surgeons the ability to effectively use the full spectrum of suture knots without adverse side effects, such as the "sawing effect" or tie slippage problems discussed above.

In particular, the prior art has not provided the means to most effectively employ endoscopic suture ligatures and loop ligatures by using slip knots that have better slippage power and may lock themselves to effectively lock the first throw of the ligature; has not provided ligator devices and slip knots with suture strands sufficiently long to be manipulated from outside a body cavity to allow tightening and locking the slip knot itself after it is applied on the target tissues, and allow the ties to be further secured with additional extracorporeal knots as is done in open surgery.

The prior art has also not provided efficient extracorporeal tying techniques for suture ligatures that use spools with pretied slip knots, which are simpler and easier to use than Ethicon's Pretied Knot Suture. Particularly, the prior art has not provided the means to complete intracorporeally the knot of a pretied knot suture in the proximity of the target tissues, using an extracorporeal technique to form a noose of small size that can be tied with a negligible amount of sawing effect on the tissues, if any.

SUMMARY OF THE INVENTION

The invention disclosed herein is a rapid loading "Sure-tie Ligature Application System" having introducer sleeves and loop and suture ligature appliers which can ligate a slip knot with lengthened suture strands that may be manipulated separately from outside the body cavity, closing the noose with one of the strands; and tightly cinching the slip knot with the other strand to lock the knot as the final step of the application of the first throw of the ligature. This is because both suture strands can be slidably enclosed within the ligature applier and the introducer sleeve. The first throw of the ligature may be further secured with extracorporeal hitch knots. Loosely woven self locking slip knots may be effectively used without accidentally jamming the noose. Five new knots with superior slipping power are introduced. Loop ligatures and loop sutures are provided with a lockable ready made slip knot. Pretied knot sutures use two types of spools which are incorporated in the various embodiments of the ligature application system; or which can be mounted on the needle driver, in which case it can efficiently form the knot outside the body cavity. If formed inside the body cavity, the noose is small and substantially reduces the sawing effect on the tissues. The similarity of all of the ligator devices is that their design allows them to load an elongated suture strand through a distal opening which exits the strand through a side opening and allows manipulation of both strands separately from outside the body cavity.

BRIEF DESCRIPTION OF THE DRAWINGS

FIG. 1 is a diagram showing the first Lehrer knot which is a two hitched locking simple slip knot. The diagram shows the four steps in forming the first Lehrer knot, using the end portion of the suture.

FIGS. 16A–16D is a diagram of a pretied knot spool made with the second Lehrer knot, to efficiently form the knot of the suture ligature outside the body cavity.

FIG. 18 is a diagram showing the alternative method of fashioning the knots shown in FIG. 1.

FIGS. 19A–D illustrate a method to manually make the first Lehrer knot on a suture ligature using the end portion suture.

FIGS. 21A–E show an alternate method to manually make the first Lehrer knot using the standing part suture.

FIGS. 22A–G show a method to manually make the fifth Lehrer knot using the standing part suture.

FIGS. 25A–C show an external sleeve with a double slit seal that admits two external instruments such as a loop ligature applier and a grasping forceps.

FIGS. 26A–C show the distal end of an alternative embodiment of the invention which utilizes internal and external sleeves.

FIGS. 28A–B illustrate the embodiments of FIG. 26 and 27 with a retractable sleeve mechanism and optional suture holder.

FIGS. 29A–E illustrate an alternative embodiment of the device shown in FIGS. 26–28. FIGS. 29A–C are top, side, and bottom views respectively. FIG. 29D is a proximal end view showing the proximal handle, the sleeve pusher, and the suture clamp with the proximal handle rotated away from the sleeve pusher. FIG. 29E shows the view of FIG. 29D with the proximal handle removed to show the location of the seal.

FIGS. 30A–B illustrate an alternative embodiment of the device shown in FIG. 29A–E. In this embodiment, the inner sleeve is replaced with the devise shown in FIG. 15.

DESCRIPTION OF THE PREFERRED EMBODIMENT

Figure 2:
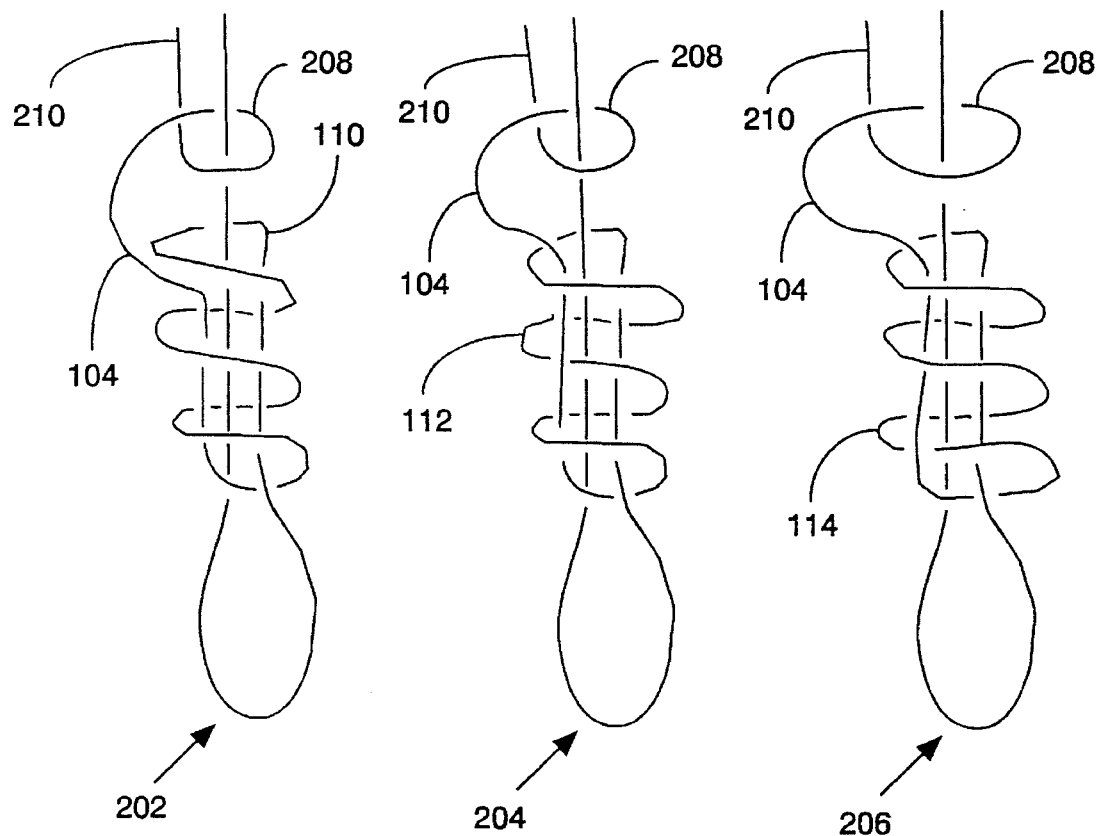
FIG. 2 which is a diagram showing the second, third, and fourth Lehrer knots being formed using the end portion of the suture.

For ease of discussion, the following terms will be used in this disclosure:

1 The "noose" is the loop formed by a sliding knot on a rope or suture, as in a lasso.

2 The "bight" is the loop formed when first crossing the suture strands.

3 The "standing part" is the suture strand that is continuous with the noose and can be mobilized through the sliding knot to control the size of the noose. The "standing part" comprises the noose and the portion of suture that extends past the sliding knot. The length of this later segment varies inversely with the size of the noose.

4 The "end portion" is the suture strand that forms the loops and hitch/s that constitute the knot itself. Once the loops are tightened to form the knot, the length of the "end portion" remains constant and does not depend on the size of the noose.

5 The term "suture ligature" is a ligature made from suitable suture material which is passed through the tissue with a needle.

6 The term "loop ligature" is a ligature made from suitable suture material which surrounds the target tissue but does not pass through it.

7 The terms "ligator device" "ligature applier", "suture applier" and "knot applier" will be used interchangeably herein.

8 The terms "external sleeve" and "introducer sleeve" are interchangeable and refer to a component of the loop ligature system that is used to keep the noose of the slip knot extended past the distal end of the knot applier device while inserting a loop ligature through the laparoscopic cannula.

For ease of illustration, the term peritoneal cavity is used when discussing the location of the surgery. However, any body cavity may be operated on using these techniques. Therefore, the term body cavity, peritoneal cavity, thoracic cavity, etc will be used interchangeably.

Prior to discussion of the suture applier, a disclosure of the following five new knots designed for use with the suture applier that is introduced will be made. The first, second, third, and fourth Lehrer Locking Slip Knots, followed by the Lehrer Double Noose Slip Knot. Those skilled in the art will recognize that while the knotting techniques disclosed herein enhance the surgeon's ability to apply ligatures and maximize the effectiveness of the suture applier, prior art knots with lengthened suture strands may also be used effectively with suture applier that is introduced. A preliminary explanation of how the knots are tied follows.

The five new knots are four locking simple slip knots and a double noosed non-locking slip knot. The first Lehrer knot is a double hitched simple locking slip knot. Its two suture strands are surrounded by the three loops that form the knot. One hitch is formed as the end portion enters the loops crossing under the anterior arch of the third loop and over the posterior arch of the second loop. The other hitch is formed after the end portion leaves the loops and forms a fourth loop around the standing part in a reverse direction to then cross the posterior arch of that fourth loop. This allows to transfer the bight to the standing part when tension is applied to the end portion suture to lock the knot. The slipping strength of this knot is superior to the prior art knots, partly due to the design of the knot and partly because these prior art knots cannot be effectively locked due to their design with a shortened suture end portion. If the first Lehrer knot is formed without step 4, the resulting slip knot has only one hitch and is non-locking. This knot is best suited for use with the pretied intracorporeal knot suture that is shown below in reference to FIGS. 14 and 15.

The three new locking knots that follow are a variation of this knot. In contrast to the first Lehrer knot, in these knots the end portion is surrounded by only two of the loops, as the end portion bypasses either the first, the second or the third loop, respectively. There is no difference in slipping strength between these three locking knots, as long as the surgeon places the bypassed loop distally, at the point where the standing part leaves the knot. The bypassed loop forms a second extra hitch that creates a bight on the standing part and will lock the knot, as long as it is positioned at the distal point of the knot. A third hitch may then be placed on the end portion and like the first Lehrer knot will be transferred to the standing part when pulling the end portion of the suture against the knot. All these triple hitched knots disclosed herein are securely lockable. The triple hitched knots are best used on loop ligatures or on the pretied knot suture ligatures and spools that are designed to complete the knot outside the body cavity. The non-locking slip knot that features a double noose is formed over a double bight in a similar fashion as the first Lehrer knot. Of course, as with other slip knots, locking the slip knot with an additional extracorporeal knot takes little extra time, but provides the surgeon an additional margin of safety.

FIG. 1 shows the first Lehrer knot. This is a simple locking slip knot 120 tied using the end portion strand. While the preferred embodiment envisions four loops, those skilled in the art will recognize that more loops may be added. Likewise, extra loops may be added to any of the other knots discussed below.

In step 1, end portion 104 crosses under standing part 102 and is wound one time around bight 108, in a counterclockwise direction.

In step 2, end portion 104 is additionally wound one and one half times around the bight 108 in a manner similar to the first round turn, and enters bight 108 from behind. The third round is counted as only one half of a round turn, because its posterior arch is not completed as end portion 104 enters bight 108 before crossing standing part 102.

In step 3, the first Lehrer locking slip knot 120 is formed by drawing the end portion 104 under the anterior arch of all three loops 110, 112, 114. A hitch 116 is formed as end portion 104 crosses under anterior arch of the third loop 114 and over the posterior arch of the second loop 112.

In step 4, fourth loop 118 is made with the end portion around the standing part, winding it in an opposite direction. Hitch 122 is formed as end portion crosses under the posterior arch of loop 118. The two ligature strands of slip knot 120 are enclosed by the four loops 110, 112, 114 and 118 that form slip knot 120, producing its superior slipping strength in comparison to other slip knots such as the Roeder loop and the Duncan loop.

Shown on FIG. 19 are pictures of a method to manually make the first Lehrer knot 120 on a suture ligature using the end portion suture. Those skilled in the art will recognize that the method shown may also be used to make a loop ligature. The steps are as follows:

(A) A bight is made by crossing the standing part suture over the end portion suture. The standing part suture is held with the thumb finger on top of the left index finger. The tip of the left index finger is placed within the bight.

(B) The left third finger is positioned parallel to the index finger, outside the bight, and over the end portion.

(C) The end portion is wound three times in a clockwise direction around the portion of the index and the third fingers that is proximal to the bight. The end portion is drawn through the bight before completing the third round turn, and enters the bight from behind.

(D) The end portion is then drawn under the anterior arch of the three loops. Each loop will be successively pulled off the left index and third fingers and closed with the end portion as the end portion is drawn under its anterior arch. The first three loops of the Lehrer knot 120 surround both suture strands and form only one hitch. The fourth loop (not shown) is then made with the end portion, forming a second hitch around the standing part suture.

The three new locking knots 202, 204, 206 that follow are a variation of the first Lehrer knot 120. FIG. 2 shows how these knots may be fashioned using the end portion suture.

The second Lehrer knot 202 is made by drawing the end portion 104 under the anterior arc of the third loop 114 and the second loop 112, bypassing the first loop 110.

The bypassed loop forms a second hitch which may produce a bight on the standing part 102 at the point where it exits the knot when the knot is cinched tightly with the end portion locking the knot.

To make the third Lehrer knot 204, the second loop 112 is bypassed by the end portion 104 and it is brought to the distal part of the knot to effectively form a bight on the standing part.

In the fourth Lehrer knot 206, the third loop 114 is bypassed by the end portion 104, and likewise, it is brought for tightening to the distal part of the knot where the standing part exits.

On Lehrer knots 202, 204, and 206, the end portion forms an extra hitch by bypassing one of the first three loops of the knot. When making any of these knots, the loop that is left only around the standing part should be placed at the point where the standing part exits the knot and loosely tightened after the other two loops are tightened first, taking care not to accidentally lock the knot.

In the knots described above, the third hitch 210 is produced by making another loop 208 with the end portion by which is wrapped around the standing part. The hitch 210 is formed as the end portion crosses under the posterior arch of the fourth loop. The third hitch 210 provides a superior degree of security of the first throw of the ligature because of the added bight it produces on the standing part, which effectively locks the knot. The first hitch formed by the first two loops must be tightened first as opposed to the second and third hitches which should be loosely formed and should be tightened by cinching the knot with the end portion after the noose has been snugly applied to the tissues 2002 (shown in FIG. 20G), as the final step in tying the ligature.

Figure 20:
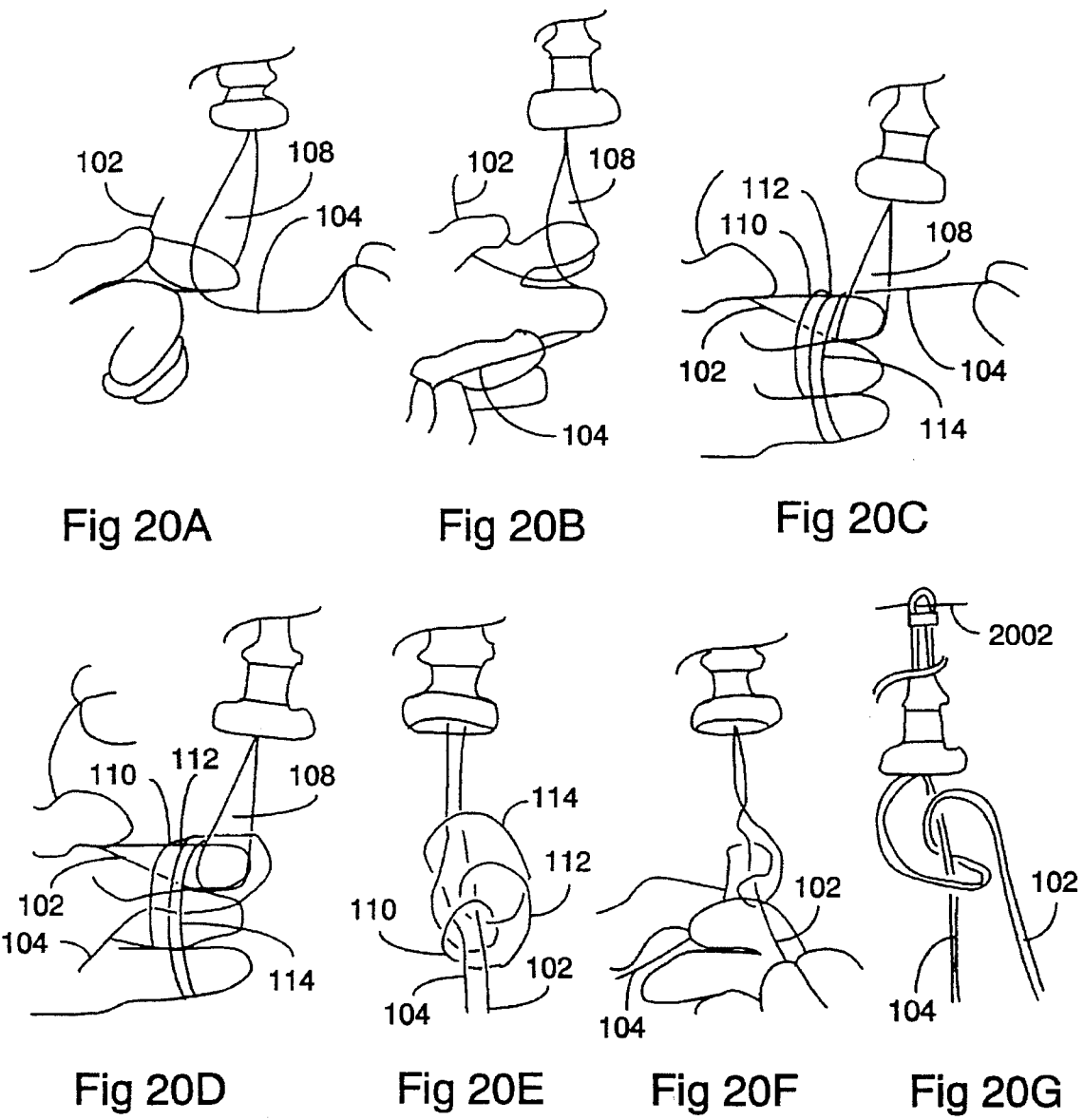
FIGS. 20A–G illustrate a method to manually make the third Lehrer knot on a suture ligature using the end portion suture; and a technique to make an additional extracorporeal security knot.

FIG. 20 shows a method to manually make the third Lehrer knot 204 on a suture ligature using the end portion suture; and a preferred technique to make an additional extracorporeal security knot.

Steps (A) and (B) are the same as described on FIG. 19.

© Likewise FIG. 19, the first round turn is made in a clockwise direction around the left index and third fingers, proximal to the bight. However, the second and third round turns are made around the index, third, and fourth fingers. The end portion is drawn through the bight, like on FIG. 19.

(D) The end portion is drawn under the anterior arch of the third and first loops, bypassing the second loop.

(E) Illustrates the arrangement of the loops just formed.

The loops will be closed with the end portion in the following manner; the third and first loops will be pulled off the fingers of the left hand as the end portion is drawn through each of them, and will then be successively tightened while the second loop is held open with one finger. This produces a rearrangement of the loops, with the second loop being positioned on the distal end of the knot, at the point where the standing part exits the knot.

The second loop will then be loosely closed with the end portion, taking care not to form a bight on the standing part which may accidentally lock the knot.

(F) The fourth loop of the knot is made with the end portion, as shown on this picture.

The second bight and the third bight may be transferred from the end portion to the standing part by cinching the knot with the end portion. This step will lock the knot and should be made at the conclusion of the application of the first tie.

(G) The first tie may be further secured with one or more extracorporeal hitch knots, if deemed necessary. The hitch knot will more easily lock the slip knot if it is made with the standing part, as illustrated; and if the standing part is used to load the hitch knot on the ligator device.

Using this suture strand instead of the end portion may be an important consideration if the surgeon has used a slip knot that is not self-locking and would like to rely on just one additional security knot to lock the slip knot.

A variation of the aforedescribed method may be used to fashion the second Lehrer knot 202, similarly using the index, third and fourth fingers to make the second and third round turns. To make the fourth Lehrer knot 206, these three fingers may be used to make the first and second round turns. Those skilled in the art know that the choice of fingers is a matter of preference that is aimed at facilitating the bypassing of one of the loops with the end portion suture.

Figure 3:
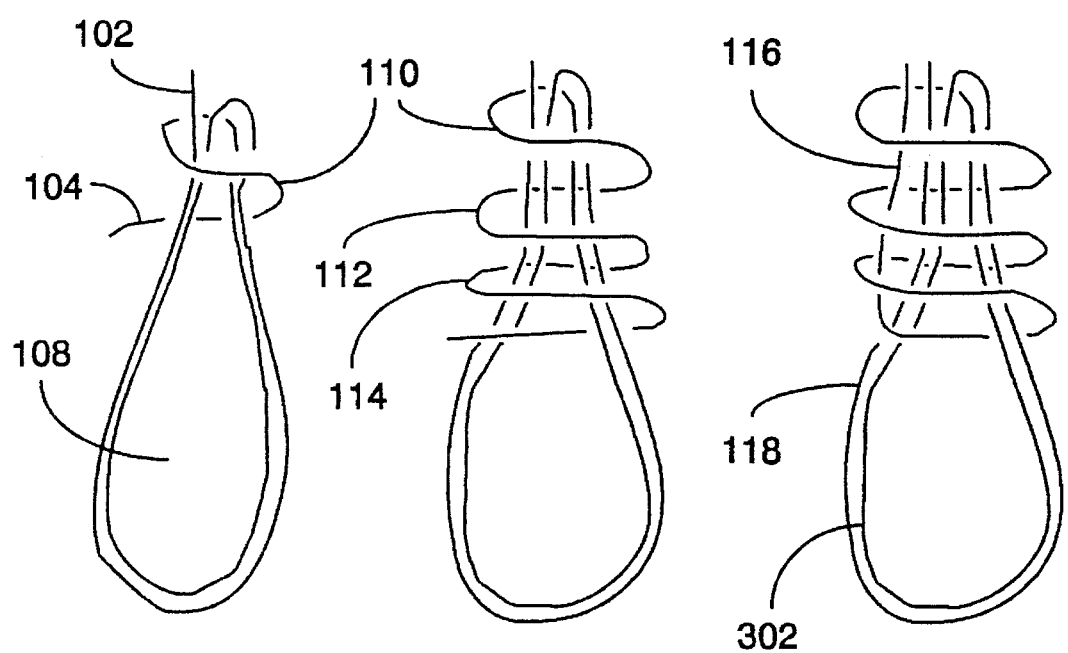
FIG. 3 is a diagram showing the fifth Lehrer knot.

FIG. 3 shows the fifth Lehrer knot 302. The double noosed slip knot is formed over a double bight in a similar fashion as the first Lehrer knot.

The feature that is common to these five new knots is that the end portion 104 first crosses under the standing part 102 to then make two and one half turns around the bight 108 and enter bight 108 from behind, forming a hitch. The third round turn is counted as only one half of a round turn, because its posterior arch is not completed as the end portion 104 enters the bight 108 before crossing the standing part 102.

In the first Lehrer knot 120, the two ligature strands are surrounded by the three loops that form the knot.

In contrast, in the three locking slip knots 202, 204, 206 the end portion 104 is surrounded by only two of the loops, as it bypasses either the first 110, the second 112 or the third 114 loop, respectively.

In the knots described above, the loop that is left only around the standing part forms the second hitch of the knot, which will more effectively lock the knot if placed at the point where the standing part exits the knot.

Those skilled in the art will recognize that while the procedure for fashioning the knots was disclosed from the point of view of using the end portion 104, the standing part 102 can also be used to make them as long as the resulting knot structure is the same and may be preferable depending on the preferences of the surgeon. Of course, pretied knots manufactured by machine will use whichever method is most efficient for the particular machine. As shown in the discussion of FIG. 18, below, the first Lehrer knot 120 can be fashioned using the standing part of the suture.

FIG. 18 shows an alternative method of fashioning the first Lehrer knot that is shown in FIG. 1 using the standing part rather than the end portion. This method can be used to fashion all the Lehrer knots with the exception of the fourth Lehrer knot. With this technique, the end portion makes three complete round turns around the bight without entering it.

As shown in steps 1 and 2, the standing part 1802 is crossed under the end portion 1804, makes three loops 1806, 1808, 1810 in a clockwise direction around end portion 1804, enclosing end portion 1804 within the loops 1806, 1808, 1810. In step 3, the third loop 1810 is drawn through the second loop 1806 and the first loop 1808; and through the bight 1812, forming the noose 1820. In step 4, another loop 1814 is made with the end portion 1804 around the standing part 1802 forming a second hitch 1818 in addition to hitch 1816 as it crosses under its posterior arch. It should be noticed that with this method, the first round turn 1806 of the standing part suture will form the third loop 114 of the final knot; and the third round turn 1810 will form the first loop 110 of the final knot. The differences between the knots shown on step 3 of FIGS. 1 and 18 is the location of first hitch 116 being on loop 114 and 110, respectively, as in FIG. 18 the end portion makes three complete round turns around the bight without entering it. However, the structure of the knots formed with either the end portion suture method or the standing part suture method is basically the same, namely, both suture strands are surrounded by the first three loops of the knot; and the number of loops and hitches of the knots is the same with both methods.

FIG. 21 shows a method to manually make the first Lehrer knot 120, using the standard part suture:

(A) The suture is placed across the top of the left index finger and is held there with the left thumb finger, leaving on the palm side an end portion strand 1804 that is about 30 centimeter (12 inches) long and about 15-centimeter shorter than the standing part suture 1802. The standing part 1802 is operated with the right hand making the first round turn 1806 and the second round turn 1808 in a clockwise direction around the index and the third fingers; and crossing under the end portion 1804 such that the end portion suture is included within these round turns.

(B) Continuing in the same direction, a third round turn 1810 is made around the third and the fourth fingers, including the end portion suture, and is held in between the left index and the third fingers.

© The surgeon grabs the end of the two suture strands 1802 and 1804 with the right hand. The first loop 1802 and the second loop 1804 will be pushed off the left index and third fingers. The third loop that is held between the left index finger and the left third finger will be pulled in a retrograde fashion through the two loops 1806 and 1808, thus forming the noose 1820.

(D) Illustrates the noose being held between the left index and third fingers. The standing part and end portion strands, which are held with the right hand are shown surrounded by the three wide open loops of the knot.

(E) The loops are closed such as to form a loose slip knot which will not get jammed. This step may be done by either using two or three fingers to enlarge the noose 1820 from within while pulling at the same time the end portion strand 1804, as illustrated here; or alternatively, by momentarily keeping the second loop open with one finger while closing the other two loops with the end portion, as show on FIG. 23 H.

The fourth loop 1814 and the second hitch 1818 will be made with the end portion strand 1804, in a similar manner as it was illustrated in FIGS. 1 and 2.

FIG. 22 illustrates a method to manually make the fifth Lehrer knot 302 using the standing part suture.

Steps (A) and (B) are the same as on FIG. 21.

© A Fourth round turn is made around the left third and fourth fingers, including the end portion suture 1804, and is held in between the index and the third fingers of the left hand, in the same manner as in the preceding round turn 1810. The surgeon grabs the end of the two suture strands 1802 and 1804 with the right hand. The noose will be formed in the same manner as described on FIG. 21 C.

(D) Illustrates the double noose being held between the index and third fingers, and the three loops that form the knot and surround both suture strands.

(E) The loops are closed such as to form a loose slip knot that will not get jammed. The preferred way to do this is using two or three fingers to enlarge the noose 1802 from within, as illustrated here, while pulling at the same time the end portion strand 1804.

(F) and (G) These diagrams of the fifth Lehrer knot 302 show that its first noose 2202 is continuous with the portion of standing part that extends past the knot; and is separated from the second noose 2204 by the hitch made by the end portion as it enters the bight and the three loops of the knot. The second noose ends with the standing part at a fixed point on the knot.

The fifth Lehrer knot has an excellent slippage power in spite of actually not being a self-locking knot. To open up the second noose, its movable portion must be mobilized upwards, which has the effect of closing the first noose, as illustrated with the arrows on (F). In fact, once both nooses are snugly applied on the target, the loosening of the second noose is prevented by the impossibility of the previously fitted first noose to close further.

Figure 23:
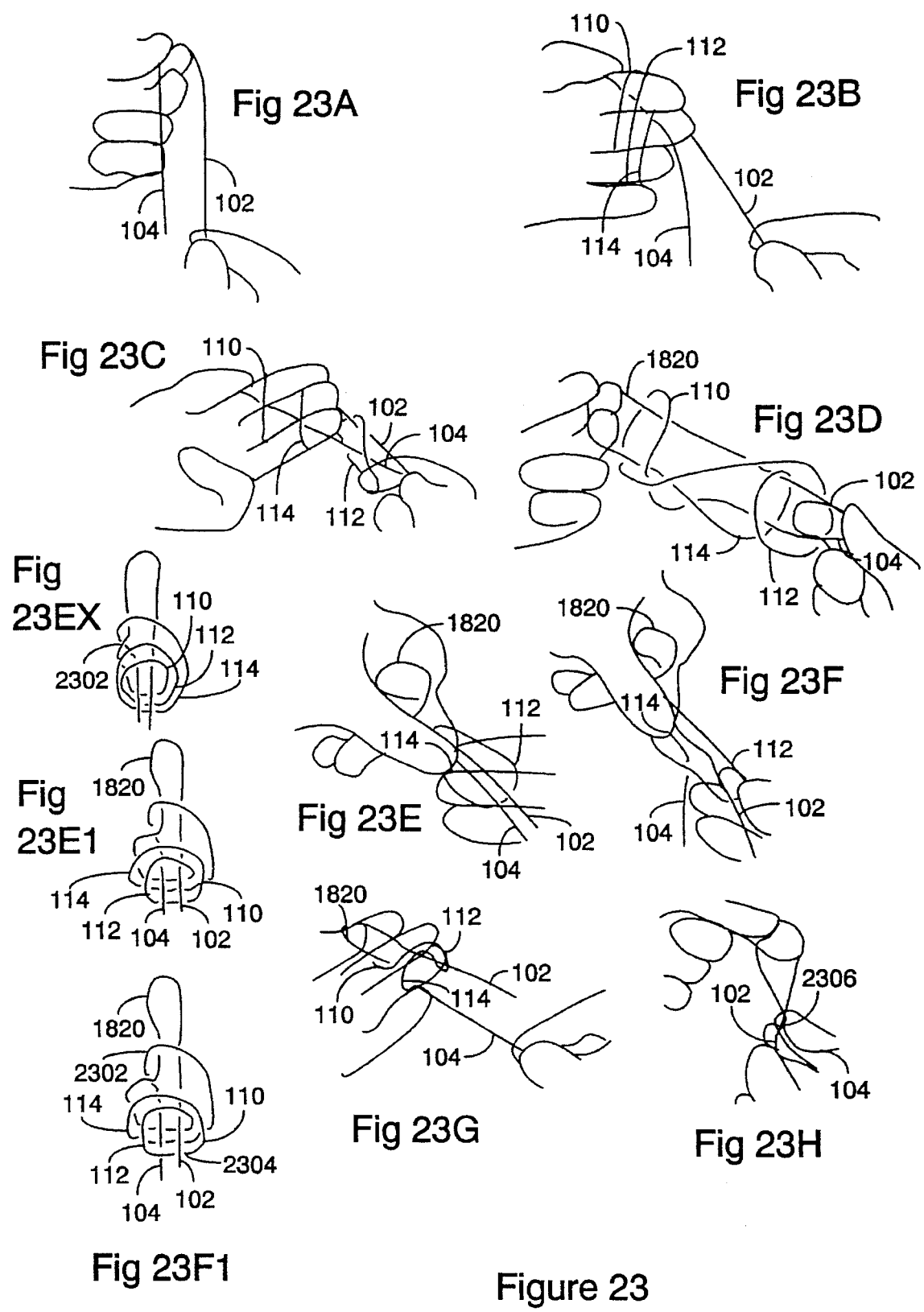
FIGS. 23A–H, 23EX, 23E1, and 23F1 show a method to manually make the third Lehrer knot using the standing part suture.

FIG. 23 shows a method to manually make the third Lehrer knot 204 using the standing part suture. This method may be also advantageously used to make the first Lehrer knot, omitting steps E and F, when using catgut or other suture materials which don't slip well:

(A) This step is the same as on FIGS. 21 and 22.

(B) The first round turn 1806 is made around the index and third fingers like on FIG. 22. The second round turn 1808 is made around the index, the third, and the fourth fingers, in order to facilitate later bringing the second round turn 1808 to the distal part of the knot. The third round turn 1810 is made around the third and the fourth fingers and is held in between the index and the third fingers of the left hand.

(Note: A similar variation may be used to fashion the fourth Lehrer knot 206 (not illustrated). The first round turn 1806 is made the largest, wounding the standing part around the index, the third, the fourth and the fifth fingers, including the end portion. The second round turn 1808 is made around the index and the third fingers. The third round turn 1810 is made in the same way as on the third Lehrer knot 204).

Those skilled in the art know that the choice of fingers is a matter of preference that is aimed at facilitating the bypassing of one of the loops with the end portion suture.

© Using the right index finger, the second loop 1808 was pulled off the fingers on the left hand, past the third loop. This picture shows the right index and thumb fingers holding the second loop, the standing part and the end portion.

As in FIG. 21, the first loop 1806 and the third loop 1810 will be pushed off the left index and third fingers. The third loop that is held between the left index and the third fingers will be pulled in a retrograde fashion through the two loops 1806 and 1808, thus forming the noose 1820.

(D) Shows the noose being held with the left index and third fingers and the relative positions of the first, third and second loops, which are widely open. The posterior arch of the second loops is held between the right index and thumb fingers.

(E) In preparation for the next step, the posterior arch of the second loop is laid on the right hand. The standing part and end portion strands are shown crossing over the posterior arch of the second loop.

(F) The surgeon drew the end portion strand under the posterior arch of the second loop. The second loop will form the second hitch 2304 around the standing part.

Before tightening the loops, the length of the standing part may be optimized such that both suture strands are left sufficiently long to span the distance from the target tissues and the outside of the abdominal cavity.

(G) This picture shows the left thumb finger placed into the noose 1820 and the left fourth finger placed within the second loop, to keep them open while mobilizing the suture strands in order to bring the end portion strand to an optimal length of about 30 cm.

The two proximal loops are then tightened one next to each other while keeping the second loop open with one of the left fingers. The second loop is then lightly closed with the end portion, taking care not to form a bight on the standing part that may accidentally lock the knot.

(H) Shows the third hitch 2306 of the third Lehrer knot, which is made with the end portion, as described on FIGS. 1 and 2.

(EX) Shows the first Lehrer knot 106. The posterior arch of the first three loops were placed one next to each other to illustrate the relative position of the three loops. In comparison with the third Lehrer knot 204, the outermost posterior arch corresponds to the third loop; the three loops of the knot enclose both suture strands; and there is one fewer hitch.

(E1) In the third Lehrer knot 204 the outermost posterior arch corresponds to the second loop of the knot. At stages D and E, the two suture strands are surrounded within all three loops, crossing over the posterior arch of the second loop as they exit the knot.

(F1) Shows the structure of the third Lehrer knot 204 at the stage F of its formation. Compared with FIG. 11, the posterior arch of the second loop lies over the end portion and under the standing part, at the point where the standing part exits the knot. Note that all three loops surround the standing part while only the first and third loops surround the end portion. The location of the first hitch 2302 and second hitch is shown.

Once the self-locking slip knot has been formed, it is good practice to tag either the end portion 104 or the standing part 102 with a clamp to identify the suture strands. In the preferred embodiment, the standing part 102 is tagged, which helps supplement its lesser initial length.

The slip knot will be loaded by its two elongated ligature strands on ligator instrument 402, 702, 902, 1002, or 1302 (shown below in reference to FIGS. 4, 7, 9, 10 and 13).

The tying technique takes advantage of both ligature strands of the slip knot, which are left sufficiently long to span the distance between the target tissues and the outside. In the preferred embodiment of loop ligatures, the end portion 104 should be drawn about 30 centimeters (or about one third of the length of a 36 inch (90 cm) suture) out of the laparoscopic cannula (not shown), leaving outside about fifteen centimeters of standing part, to allow the extracorporeal manipulation of both suture strands after the slip knot has reached the target tissues. Those skilled in the art will recognize that while a 30 centimeter long end portion suture was used in the preferred embodiment, any suitable length of end portion suture may be used as long as there is adequate length for the surgeon to extracorporeally manipulate and/or tie ligatures.

In the preferred embodiment of pretied knot suture, the lengths of end portion 104 is similar to the loop ligature. However, the total length of suture is either 36, or preferably 48 inches.

The slip knot is loaded by its two ligature strands on suture applier 402 (shown below in reference to FIG. 4). The surgeon can manipulate separately each ligature strand from outside the abdominal cavity while holding the slip knot at the tip of suture applier 402.

Pulling standing part 102 through the knot itself effects the closure of noose 118 on the target tissues. In contrast to hitch knots, slip knots cannot be pushed because the loops of end portion sutures have been already tightened to form the knot. In fact, slip knots are held at the tip of ligator device 402 as standing part 102 glides through the knot itself while the surgeon gradually pulls it to effect the closure of noose 118. The position of the knot relative to the ligature strand is not necessarily related to the spacial positioning of the knot, which is held and positioned with the tip of suture applier 402. This concept will be presented in detail when discussing the preferred knot tying technique that may minimize trauma to the tissues.

The slipping strength of the slip knot is negatively affected when tension is applied to standing part 102. As discussed above, Hay correlated the increase in slippage rate of the knot with the number of pulls applied on the standing part. The tying of the slip knot of either loop or suture ligatures should be concluded with a final pull on end portion 104 while keeping the knot applied against the tissues with the ligator. The application of tension on end portion 104 is preferably deferred until after the noose has been snugly applied on the tissues, to prevent the knot getting accidentally jammed or even locked. The extracorporeal technique introduced herein allows the surgeon to easily restore the slipping strength of the knot by applying tension on the lengthened end portion 104, against the knot being held at the tip of a suture applier 402. This tightens the knot, increasing its slipping strength, and in addition, this may close the second and third hitches of the knot, forming one or two bights on the standing part that lock the knot. This technique can be effectively used to apply any of the self-locking slip knots presented herein. The above also applies to prior art slip knots to substantially enhance their slippage power.

When using one of the spools introduced herein for a pretied knot suture, leaving both suture strands long allows manipulation of the suture strands from the outside after bringing the standing part outside with a wire guide loop. Then by manipulating the end portion suture from the outside, the pretied loops can be pushed over an appropriate length of the standing part, thus completing the formation of a knot within the abdominal cavity, forming a small noose that may be tightened with a negligible sawing effect on the tissues.

The extracorporeal technique to make one or more extracorporeal hitch knots to further secure the slip knot is best accomplished if:

First, both strands of the suture are sufficiently long to make the extracorporeal knot. In the preferred embodiment of a loop ligature, sutures having lengths of 27 inches (67.5 cm) or 36 inches (90 cm) have been found to be suitable. The slip knot is located near the mid-point of a 27-inch (67.5 cm), or preferably, a 36-inch (90 cm) suture, which will leave an end portion that is about 13 inches (32 cm) long, as an approximate minimum length of end portion suture. After tying the slip knot, the standing part will have a similar length. Those skilled in the art will recognize that many factors, including the physical size of the patient, and/or the location of the laparoscopic port relative to the target tissues will influence the ideal length of a suture. Therefore, the only requirement as to suture length is that the strands be long enough to allow convenient extracorporeal knot tying. In the preferred embodiment of pretied suture, the end portion of the suture is about 30 cm long or 12 inches, and the total suture length is 36 or 48 inches.

Second, the hitch knot is made using the standing part of the slip knot.

Third, the hitch knot is loaded on the knot pusher instrument by the standing part.

If the end portion is instead used in any of the last two aforementioned steps, the tie may remain unlocked, which is important if the surgeon relies on just one security knot to lock the slip knot. However, when multiple security knots are used in sequence, bights can be transferred from strand to strand by alternatively reversing the relative direction before applying tension on the strands to tie each of the knots. This technique allows locking of the tie without switching suture strands when making the hitch knots.

In addition to the slipping strength provided by the knots themselves, the suture materials are also an important factor in the slipping strength of a slip knot. Catgut gives the highest slipping strength but is a poor choice because it is a highly reactive material. Braided sutures such as silk and POLYGLACTIN (Vicryl or Dexon), and silk, have the second highest slipping strength; followed, in decreasing order, by POLYDIOXANONE (PDS), POLIGLECAPRONE (Monocryl), PTFE (Gore-Tex), POLYGLYCONATE (Maxon) and nylon, all of which are commonly available products.

When both the suture material and the slip knot: have a low slipping strength, the effect of their combined use on the quality of the tie can be substantial. For example, the Roeder loop and, to a lesser extent the Duncan loop, have substantially less slipping strength when made with braided suture materials instead of catgut.

Locking knots such as the second, third, and fourth Lehrer knots, and the Weston knot (which is well known in the art. e.g., Weston PV. A New Clinch Knot. Obstet Gynecol 1991: 78:29. July No. 1) have the best slipping strength, followed in decreasing order by the first and the fifth Lehrer knots, the Duncan loop and the Roeder loop. The reason for this difference lies in the structure of the knots. The superior slipping strength of the triple hitched locking Lehrer knots shown in FIG. 2 is due to the second and/or third hitch distally formed around the standing part; and the fact that the other two loops that form the knot itself enclose the end portion, holding it in place.

Regarding the structure of self locking Lehrer knots shown in FIG. 2, two of the three hitches of these knots are distally formed around the standing par; and all four loops of the knot enclose the entire end portion suture, which helps maintain the tightness of the knot.

The four loops that form the first Lehrer knot in FIG. 1 are wrapped around the end portion strand, compared to only one of the four loops of the Duncan loop and the Roeder loop. In addition, the second hitch produces a better bight on the standing part, because of its location at a point where the standing part exits the slip knot, accounting for their different slipping strength in spite of the fact that all these knots have two hitches. Another factor that determines the slipping strength of a slip knot is the technique used to apply it to the target tissues. Each time that the standing part is pulled to tie the noose of the slip knot, the resulting straightening of the standing part tends to eliminate its bight and unravel the knot itself. This is particularly true in the case of the Roeder loop, because it only has one of its loops surrounding the end portion of the suture. The loss of slipping strength of the Roeder loop that occurs in proportion to the number of pulls to apply it, reflects the loosening of the single loop that holds the end portion and the loss of compression and/or distortion in the traject of the standing part, rather than the weakening of the suture material that Hay suggested as the explanation.

The loss of slipping strength that occurs as a result of the above can be reversed by applying tension on the end portion, while holding the knot in position with the tip of the suture applier 402. For this reason, the application of a loop ligature should conclude with a final pull on the end portion strand, to restore the knot itself, which is easily done with the extracorporeal technique and suture applier 402, discussed below.

As previously stated, making one or more extracorporeal security knots requires little time, and may provide an extra margin of safety. The surgeon should preferably use the standing part of the slip knot to fashion the security knot. In most circumstances, either the second, third or fourth set of Lehrer knots are sufficient with Vicryl/Dexon or silk; and only one extracorporeal security knot may be required with Gore-Tex, Maxon or nylon, provided that these knots are made and applied using the standing part of the slip knot.

The bulk of the knot is another relevant consideration. The Roeder loop and the Duncan loop have four round turns and therefore, are bulkier than the simple slip knots introduced herein, which have as few as two and one half round turns, but may have additional turns at the surgeon's discretion. The bulk of the double noosed slip knot is less than the corresponding bulk of two simple slip knots, because these two nooses share a single knot. While its bulk is larger than the bulk of any of the slip knots discussed herein, its bulk would fare favorably visa vis the combined bulk of three unlocked Roeder loop ligatures that the prior art applies on a single pedicle.

The Weston knot is a locking knot that is the smallest of all the knots compared. However, this is not an advantage from a technical viewpoint, because a knot of larger diameter is less likely to be pulled into the opening formed by the indented end of the suture applier 402 and the sheath 416 when tension is applied on the standing part to close the noose. In the Weston knot, the end portion forms only two loops around the two suture strands but its two long hitches tend to untwist after the Weston knot has been locked, when tension is applied distally on the noose. This causes the Weston knot to unbuckle, resulting in a slight loosening of the noose in spite of the fact that the knot is well locked. Once the Weston knot is locked, it may not be possible to again tighten the noose further. These observed effects are absent in the locking simple knots that are introduced herein, which have the additional advantages of being easier to make and place on the mid-portion of the suture; and of having considerable less tendency to get accidentally locked. The Weston knot can be loaded on the suture applier 402 by both suture strands, which is the technique that works best for all locking slip knots.

Figure 4:
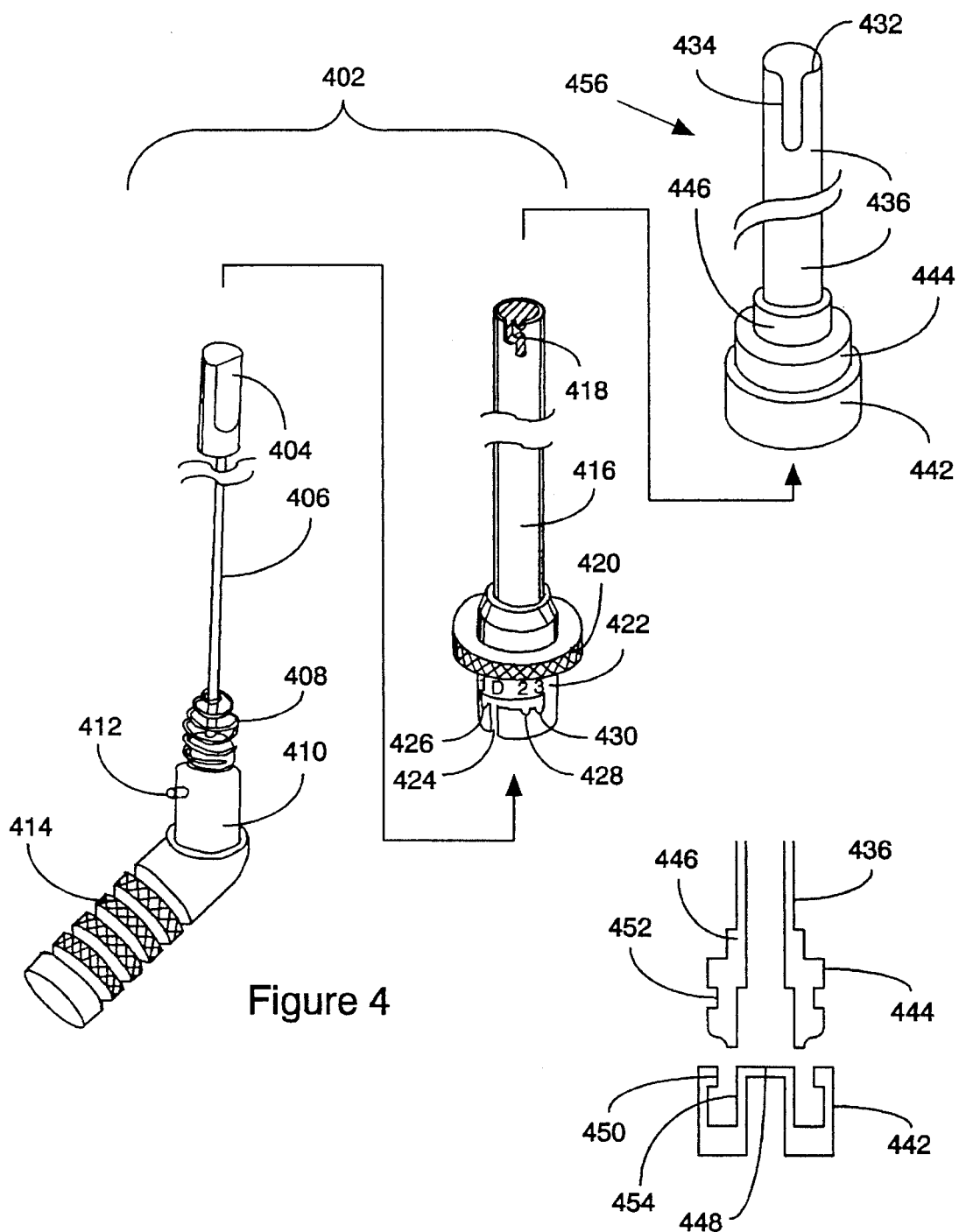
FIG. 4 is a diagram of a preferred embodiment of the knot applier device and introducer sleeve.

Turning now from the knots to the apparatus for applying the sutures, FIG. 4 shows the preferred embodiment for the invention in non-disposable form. In this embodiment, as well as the others discussed below, the slip knot is manipulated by the particular suture applier such that it can be held and tied at the distal end of the applier in close proximity to the target tissue, and its elongated suture strands are manipulated separately from outside the body cavity, closing the noose with the standing part, and cinching the knot to lock it with the end portion strand, as a final step. Addition extracorporeal hitch knots may be applied to further secure the tie if so desired. The preferred embodiment envisions a distal opening and a distal side opening. The distal opening is intended to keep the knot of the slip knot at the tip of the ligator such that it is not dragged into the space between the indented surface of the shaft and the sheath when tension is applied to the sutures. The distal side opening through which the sutures exit the instrument is intended to easily open for accepting the sutures into the instrument and to enclose or fixedly grasp the sutures at the point where they exit the instrument so that they can be manipulated externally against the knot that is held at the tip of the instrument. For ease of illustration, lengths of the instruments, and their corresponding widths are not drawn to scale in order to more readily show the particular features of the mechanical structures in question. In practice, as with other endoscopic suturing instruments the usable length of shaft is about 30 cm which is enough for the surgeon to conveniently reach the target tissues in a patient. Likewise, the diameter of the instrument at the distal end has to be wide enough to fit through the size access port selected by the surgeon. In the preferred embodiment, it should be able to fit through a size 5 laparoscopic cannula and accommodate the particular type of suture and/or guidewire being used. Of course, the proximal end should be of a size to allow the surgeon to conveniently manipulate it by hand. In this embodiment, suture applier 402 is made of a tubular external sheath 416, and a solid shaft 406, that forms one body with the handle 414.

The internal shaft 406 has one indented edge 404 on the surface of the shaft at its distal end, which determines the size of the top opening 502 (shown in FIGS. 5 and 12) which is the distal entrance to the opening that exists between the internal shaft 406 and the sheath 416. The top opening 502 at the distal end of the device is sized to prevent the knot from entering the opening between the indented edge 404 of the internal shaft and the sheath 416 when tension is applied to the suture strands.

Figure 5A:
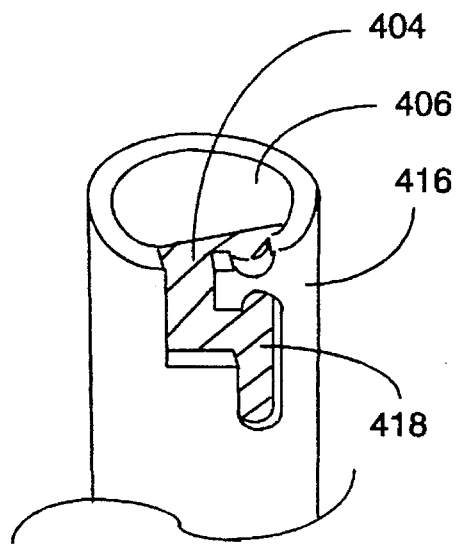
FIGS. 5A–5C are detailed view of the distal end of the knot applier device of FIG. 4.
Figure 5B:
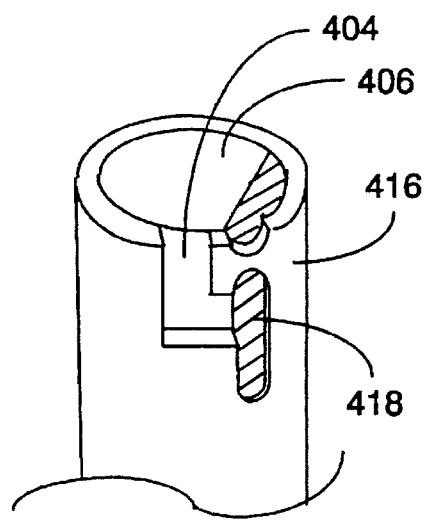
Figure 5C:
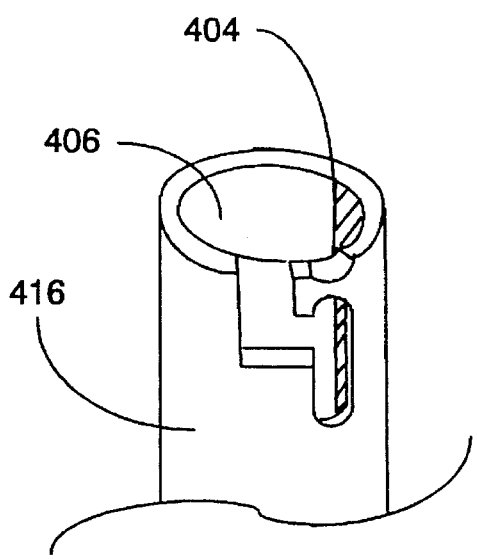

The distal end of the preferred embodiment envisions a top opening 502 and a side opening 504 (shown in FIG. 5). In the preferred embodiment, the two suture strands of the slip knot are loaded into the short opening between the sheath 416 and the indented edge 404 of the internal shaft at its distal end, and exit the instrument through the openings 502 and 504.

The side opening 504 is intended to have three functions:
A) To easily open for accepting the sutures into the instrument;
B) To loosely enclose the sutures, so that they can be manipulated from outside the body cavity while the knot is held at the tip of the instrument; and
C) To fixedly grasp the sutures at the point where they exit the instrument.

Sheath 416 and the shaft 406 are sized to fit telescopically one within the other. They are held together by the retainer 412 of shaft 406, which is maintained in place within one of the three notches 426, 428, 430 of sheath 416 under pressure from spring 408. One end of spring 408 rests against the widened proximal end 410 of shaft 406. The other end of spring 408 fits within the widened proximal end 422 of sheath 416 and provides outward pressure to hold retainer 412 in whichever notch 426, 428, or 430 which is selected. Shaft 406 is initially inserted into sheath 416 such that retainer 412 slides into opening 424. When retainer 412 is fully inserted, sheath 416 is rotated to one of the notches 426, 428, or 430. Retainer 412 and notches 426, 428, and 430 are in alignment with their corresponding distal slot 418. Suture applier 402 has three settings—Open, Enclose and Fasten—that are selected by rotating the retainer into one of the three notches 426, 428, or 430, respectively of sheath 416.

To operate suture applier 402, sheath 416 can be axially rotated using a single hand gripping intermediate portion 420, while holding suture applier 402 by handle 414. The surgeon first pulls sheath 416 toward handle 414 to compress spring 408, disengage retainer 412, and coaxially rotate sheath 416 over shaft 406. This rotation results in distal opening of slot 418 moving in and out of alignment with the indented surface 404 of suture applier 402, depending on which one of the three notches 426, 428, or 430 of sheath 416 retainer 412 is placed. For ease of illustration, the width of shaft 406 is shown greatly enlarged at the distal end to provide a better view of indented surface 404.

Figure 4A:
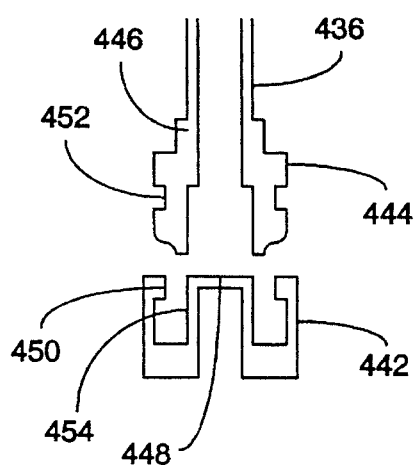

FIG. 4A shows a cross sectional view of the introducer sleeve 456 and silastic seal 442. Tab 450 fits into groove 452 to firmly hold seal 442 in place when mounted on introducer sleeve 456. Male section 454 of seal 442 fits snugly within introducer sleeve 456. Slit 448 allows easy entry of a ligator applier or other surgical instruments while closing to protect the body cavity while not in use. Slit 448 is preferably cut such that it forms a cross with one of the slits longer than the other. Those skilled in the art will recognize that introducer sleeve 456 and seal 442 can be sized to allow the use of a plurality of slits 448. By so doing, a plurality of surgical instruments can use the same introducer sleeve 456.

The foregoing structure illustrates a prior art seal structure which has the problem of sometimes becoming detached from the external sleeve when instruments are being removed. A more detailed discussion of an improved single or multiple instrument introducer sleeve 456 is provided below in regard to FIG. 25. The improved alternative seal and seal mounting structure disclosed in FIG. 25 solved the accidental detachment problem by providing a more secure hold on the seal.

FIG. 5 shows the three positions A, B, and C (open, enclosed, and fastened) of the distal end of suture applier 402 when the three notches 426, 428, and 430 are engaged. For ease of illustration, the 3 diagrams in FIG. 5 show the frontal view of sheath 416. However, it should be noted that sheath 416 is axially rotated over the shaft, which is fixedly attached to the handle of the device.

In the open position A, retainer 412 is placed within first notch 426, the indented surface 404 of suture applier 402 and the distal opening of distal slot 418 are in alignment, allowing suture applier 402 and sheath 416 to easily admit one or two suture threads within the channel (e.g. an interior space) formed between indented surface 404 and sheath 416. This channel extends between the top opening 502 and side opening 504, which corresponds to the proximal section of slot 418.

Those skilled in the art will recognize that while the size of a knot depends on the thickness of the suture material and the number of loops it is made of, the size of the top opening 502 must be adapted accordingly, in order to keep the knot at the tip of the knot applier device and prevent the knot from being drawn into the opening formed between the indented surface 404 and sheath 416. The size of the top opening 502 depends on the width and depth of the indented edge 404, which is different in the various knot applier devices for use with one particular size of surgical sutures. The design for smaller sutures requires to make an L-shaped indented edge 404 that is rounded at its elbow, such that it may admit the two sutures laid into it through the transverse and distal sectors of slot 418 which overlies it, as shown on FIGS. 9, 11, 12, 13 and 24. The transverse extension 922 of the indented edge 404 allows to load the two suture strands of the slip knot through the entire extension of the opening that exist between the indented edge 404 and the overlying sheath, from the top opening 502 to the side opening 504, when the device is placed in the open setting.

In the enclose setting B, the distal section of slot 418 is closed by the underlying shaft, thus loosely enclosing the suture within the proximal section of distal slot 418 that remains open on the side of the instrument. Enclosed position B is engaged as follows. Sheath 416 is rotated, moving retainer 412 into notch 428. This places distal section 418 of suture applier 402 out of alignment with indented surface 404, and the distal section of distal lateral slot 418 is closed by the underlying shaft. This prevents the suture from falling out of suture applier 402. However, because distal slot 418 has two parallel sections, one distal and the other proximal, the proximal section remains in alignment with indented surface 404 while the distal section is no longer in alignment. This allows the suture to freely slide within side opening 504 without disengaging from suture applier 402. In the enclose setting B, suture applier 402 can be used to apply and tighten the slip knot of suture and loop ligatures. In addition, it can be used as a closed-end knot pusher, to deliver one or more extracorporeal security knots to lock a tie, like in Open Surgery. A Surgeon's Knot and/or one or more hitch knots can be applied without encountering the loss of contact with the suture that can occur with the prior art open knot pusher devices.

Before changing the setting of the instrument from Enclose into Fasten, the knot must be brought to touch the top opening 404 at the distal end of the suture applier 402, to fixedly position it centrally on the tip of suture applier 402 in preparation to the insertion of the loop ligature through the laparoscopic cannula.

Further rotation of sheath 416 places retainer 412 into the last notch 430 (fasten position C). Side opening 504 is almost completely obliterated by the underlying shaft, resulting in the fastening or gripping of the suture—or sutures—that were loaded on suture applier 402. In this position, the side opening 504 of distal slot 418 is substantially closed such that a suture is firmly grasped by suture applier 402. Those skilled in the art will recognize that the size of the lateral enclosure can be adjusted to fit a variety of suture materials. Likewise, the indented surface 404 can be made of various widths or can be shaped as a groove, which determines the size of the distal opening 502 of the space formed between the indented surface of shaft 406 and the sheath 416, in order to fit a variety of slip knot sizes and prevent the knot from being drawn into the space formed between the indented surface 404 and sheath 416 when tension is applied against it with the suture strands. Side opening 504 of the sheath is almost completely obliterated by the underlying shaft, resulting in the fastening or gripping of the suture—or sutures—that were loaded on suture applier 402. In this position the side opening 504 of lateral slot 418 at the distal end of the sheath is substantially closed such that a suture is firmly grasped by suture applier 402.

Those skilled in the art will recognize that the size of the side opening 504 can be adjusted to grip a variety of suture thickness sizes.

Suture applier 402 can be used in the fasten setting to introduce loop ligatures into the peritoneal cavity. The slip knot is preferably loaded by both suture strands and it is positioned centrally on the tip of suture applier 402 to be inserted through a laparoscopic cannula. This requires an introducer sleeve in order to keep the noose in an extended position past the distal end of the ligator.

This setting can also be used to introduce or remove suture needles through a laparoscopic cannula, by grabbing the suture at one or two-centimeter distance from the needle.

In the preferred embodiment, the external sleeve 436 of suture applier 402 fits through a size #5 laparoscopic cannula, leaving extra room for the sutures. However, those skilled in the art will recognize that the size of suture applier 402 can vary to suit the needs of a particular procedure. Likewise, the number of notches can also be varied. For example, four, five, or more notches could be employed to allow suture applier 402 to hold a variety of suture thickness sizes. In addition, only two notches may be employed to create a device which has only open and enclose positions with no fasten position, but has similar functions as a slip knot applier and as a closed end hitch knot pusher.

In this knot applier device, the lack of a fasten position C may be compensated by slidably bringing the suture strands to the outside of the body cavity through an adequate opening between the external sleeve 436 and a sheath 416 of a lesser diameter. The slip knot must be loaded before mounting the sleeve 436 over the sheath 416. After loading the sleeve through the distal end of the sheath, the sleeve must first be displaced towards the proximal end of the sheath to allow extending the noose forwards and past the end of the sheath; to then advance the sleeve around the noose, encasing it for insertion through the laparoscopic cannula. Those skilled in the art will recognize that this knot applier device with only open and enclose settings may also function as a closed end knot pusher, without the need of sleeve 436. For further discussion, please refer to FIG. 17.

Figure 6:
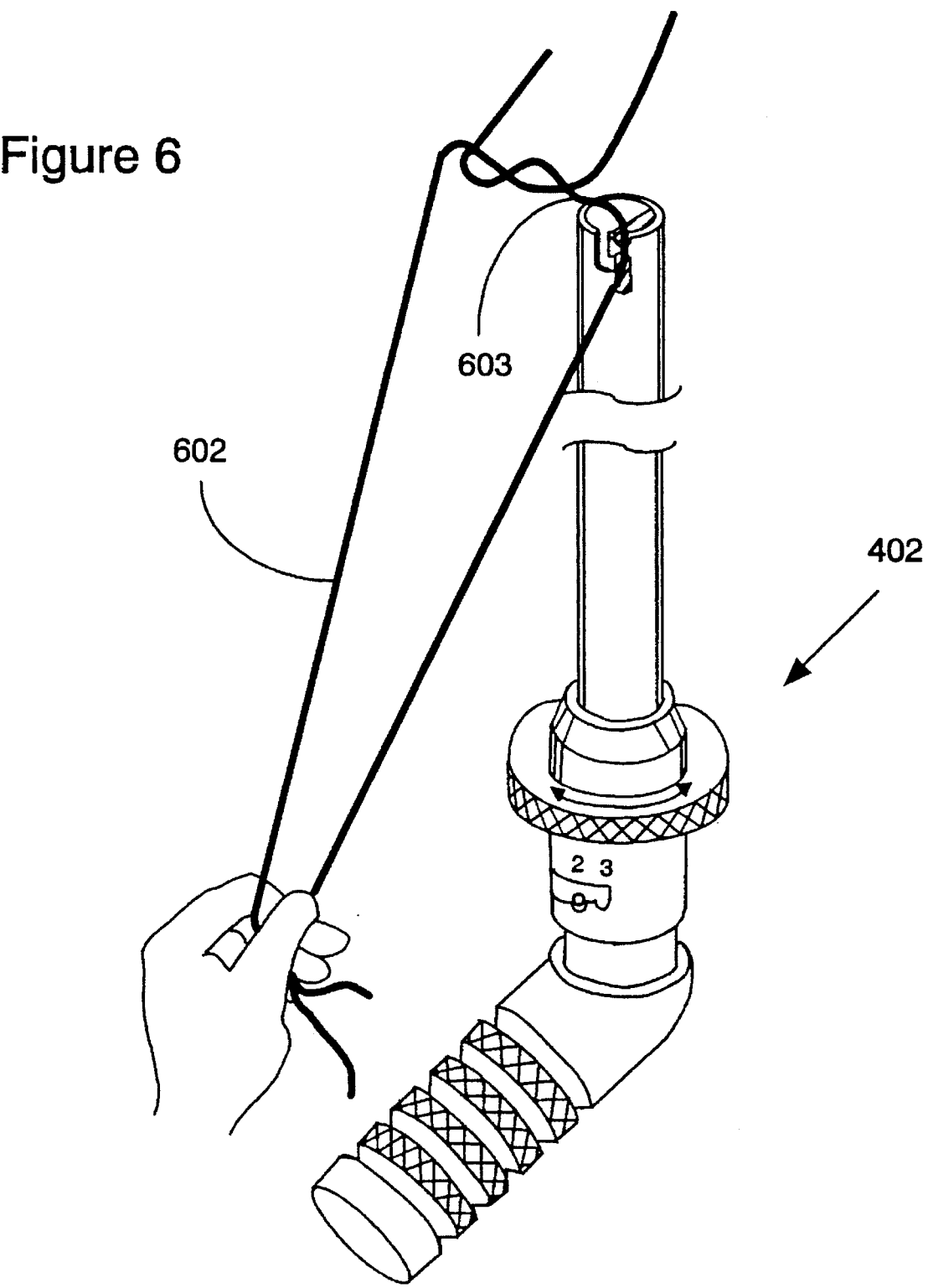
FIG. 6 shows the ligator device of FIG. 4 in use as a knot pusher.

In FIG. 6, a hitch knot which is loaded on the ligator device is shown. The standing part 603 of previously tied slip knot is shown loaded onto suture applier 402 in enclose setting B. The portion of standing part 603 that is proximal to the hitch knot should be left two or three centimeters longer than the corresponding length of end portion suture 602 in order to facilitate pushing the knot toward the tissues. This allows the surgeon to extracorporeally push a hitch knot and tie it on the tissues without the problem of losing control of the suture.

The steps to load the ligator instrument are graphically shown below, on FIG. 24.

The ease of loading this instrument makes it suitable for use as a reusable ligator apparatus in conjunction with slip knots self made by the surgeon; ready made slip knots for loop ligatures, or pretied knot sutures mounted on a spool. As discussed in regard to FIG. 16, these spools may be mounted on the shaft at the proximal end of an endoscopic needle driver, and are used to rapidly form the slip knot outside the body cavity after the needle driver has been used to pass the suture needle through the tissues, remove it through the cannula, and pass the standing part suture through the spool after cutting the suture needle off the suture. This also effectively opens the doors for surgeons to make their own loop ligatures and suture ligatures using regular suture materials and a wide variety of suture needles, as described on FIGS. 19, 20, 21, 22 and 23. As mentioned before, the instrument can also be used as a knot pusher that is easy to load, which allows surgeons to extracorporeally make an effective square tie with a minimum number of knots by alternately switching the suture strands as in open surgery when forming each of the hitch knots, which is an advantage in comparison to other closed-end knot pusher devices because the surgeon is more assured of delivering a square tie.

A faster technique to tie hitch knots that saves the need for switching the suture strands when successively making a hitch knot on a suture ligature consists of advancing the suture that carries the knot past the knot, before tying it, thus reversing the relative direction of the strands and resulting in the alternate transfer of a bight from one strand to the other, which is similar to the bights formed by a square tie (Leslie Sharpe, M.D., personal communication).

The same external sleeve 436, shown on FIG. 4, can be used with any of alternate models 702, 902, 1002, 1302 and 1702 (shown below in reference to FIGS. 4, 7, 9, 10, 13 and 17). It can also be used with ligator devices 1402 and 1502 (shown below in reference to FIGS. 14 and 15) and the loop ligature applier that is discussed in relation to FIG. 17.

The external sleeve 436 is about 15 to 17 centimeters long. Those experts in the art will recognize that the length may be changed, depending on the relative lengths of the surgeon's preferred laparoscopic cannulas and ligator devices. The external sleeve 436 is mounted over the knot applier device 402 before loading the slip knot, such that the suture strands are outside the sleeve 436 while introducing it through a size 5 laparoscopic cannula. The two lengthened suture strands that extend from side opening 418 of ligator device 402 to the outside of the body cavity slidably occupy the opening existing between the external sleeve 436 and the laparoscopic cannula, such that the sutures may be manipulated from the outside without necessitating the withdrawal of the external sleeve 436 from the cannula. A proximal rubber or silastic seal 442 is mounted on an adaptor 444 which opens through the distal end 432. Longitudinal groove 434 measures approximately 6 centimeters in length and about 1 mm in width and its purpose is to allow advancing the introducer sleeve 434 past the distal end of the ligator device to enclose the extended noose, bypassing the sutures that exit the device from its distal side opening 504. Distal end 432 is slanted towards the groove and like groove 434 has rounded and smooth edges. The sutures will exit the body cavity through the space between the introducer sleeve and the laparoscopic cannula.

The introducer sleeves that are used in conjunction with the ligator devices which lack the fasten mode discussed above, differ from the above described sleeve in that the groove 434 is not required as discussed more fully below in the discussion of FIG. 17. Likewise, the sutures and the noose are enclosed within the introducer sleeve in order to protect them from the drag that the laparoscopic cannula may produce on the sutures during the procedure to introduce the loop ligature into the body cavity.

Excepting those knot applier devices that lack a fasten setting, the external sleeve 436 must be mounted on the ligator device 402 before loading the loop ligature. Once the slip knot is loaded, the noose is extended forward past the distal end of ligator device 402 and then the external sleeve 436 is advanced forwards, such that the proximal end of groove 434 reaches side opening 504 at the proximal end of slot 418, without blocking it; and sleeve 436 completely contains the entire noose to keep it in an extended position, past the distal tip of the ligator device after the insertion through the cannula. The relative positions of the external sleeve 436 and the knot applier device 402 within this aforedescribed assembly must be maintained while the two components are introduced simultaneously, until the distal end of external sleeve 436 that contains the noose is extended about 3 to 6 centimeters past the tip of the laparoscopic cannula. The external sleeve 436 is then pulled back, thus exposing the noose and the distal end of sheath 416, which may then be advanced towards the target tissues.

Figure 7:
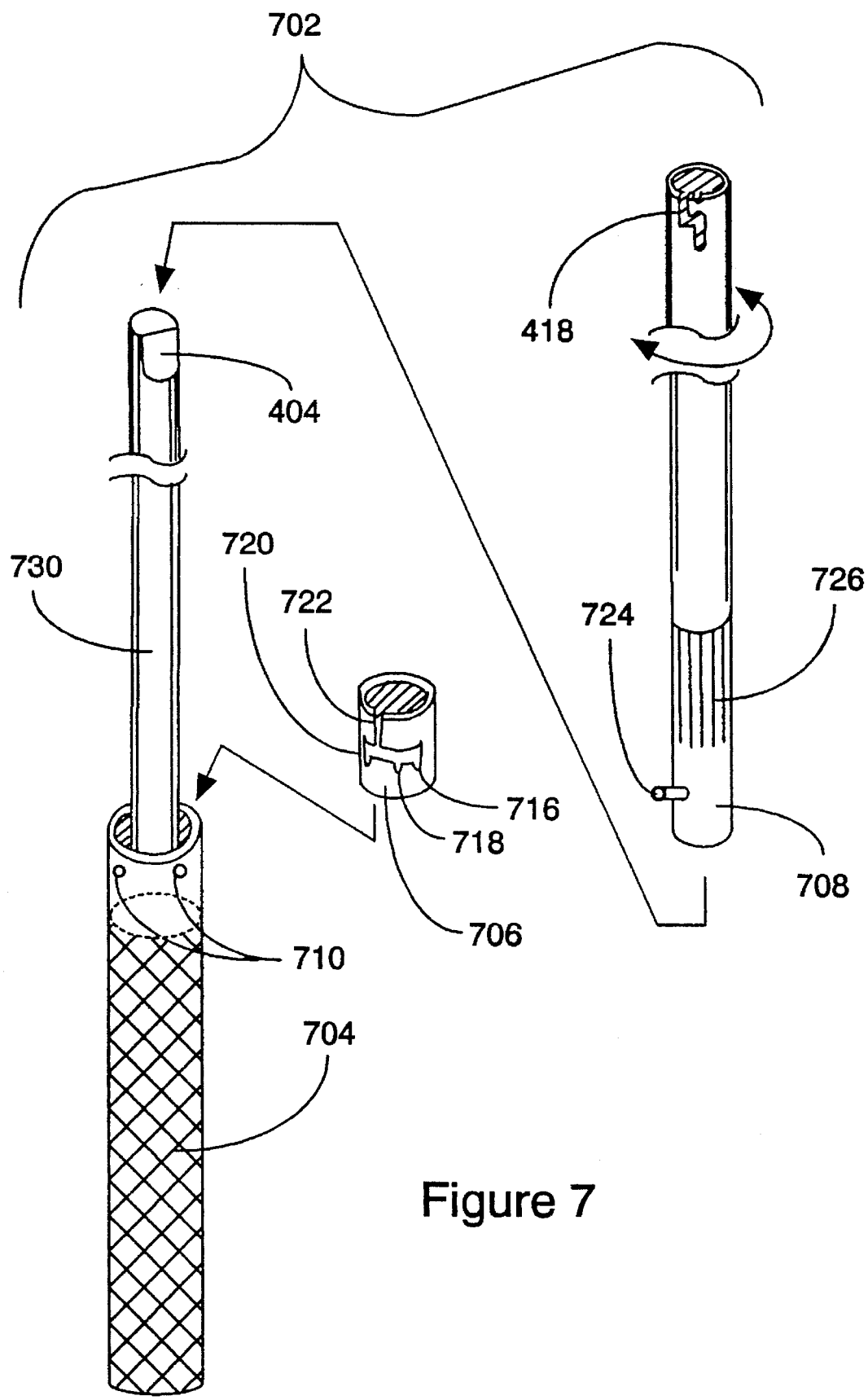
FIG. 7 is an exploded view of an alternative embodiment of the knot applier device.

An alternative embodiment in the form of a disposable suture applier 702 is illustrated on FIG. 7. Similar to the reusable suture applier 402, the surgeon places the two components of the instrument in or out of alignment by rotating sheath 708 over shaft 730 while holding handle 704. Only the proximal portion of disposable suture applier 702 was changed from the design discussed above in relation to FIG. 4, leaving the same distal elements on sheath 708 and on shaft 730.

Sheath 708 is greatly simplified by eliminating intermediate portion 420 and spring 408. Intermediate portion 420 is effectively replaced by providing a knurled surface 726 for gripping. Spring 408 is replaced by providing a pressure fit created by constructing slot insert 706 of flexible material such as plastic or the like. This allows slot insert 706 to either deform when sheath 708 is inserted into slot insert 706 and retainer 724 is then rotated into one of the notches 716, 718, or 720, or it allows retainer 724 to snap in and out of notches 716, 718, or 720 on the proximal end of the shaft.

The wider segment 410 of shaft 406 was likewise eliminated and retainer 724 was transferred to the outside of sheath 708.

In the preferred embodiment, the distal portion of handle 704 is tubular and extends about 1.5 to 2 centimeters over the end of the shaft, which forms one body with it, as in the reusable suture applier 402. Those skilled in the art will recognize that this distance is not critical and may be modified to suit variations in design.

Slot insert 706 has an L-shaped slot and three notches. It is attached inside the tubular portion of handle 704. Slot insert 706 is held in place by set screws 710. Those skilled in the art will recognize that any suitable retention means may be used in place of set screws 710, such as rivets, tacks, glue, epoxy, etc. However, screws allow the operator the versatility of rotating slot insert 706 to fine tune the instrument by realigning the notches.

Sheath 708 is sized to telescopically fit within handle 704 and around shaft 730. Sheath 708 has a knurled portion 726 that is ergonomically placed close to handle 704 of suture applier 702 and may be placed across the surgeon's index finger to grasp it between the index and thumb fingers. The retainer snaps in or out notches 716, 718, 720 when the surgeon pulls or pushes sheath 708 to rotate it and operate the device.

Figures 8A, 8B, 8C:
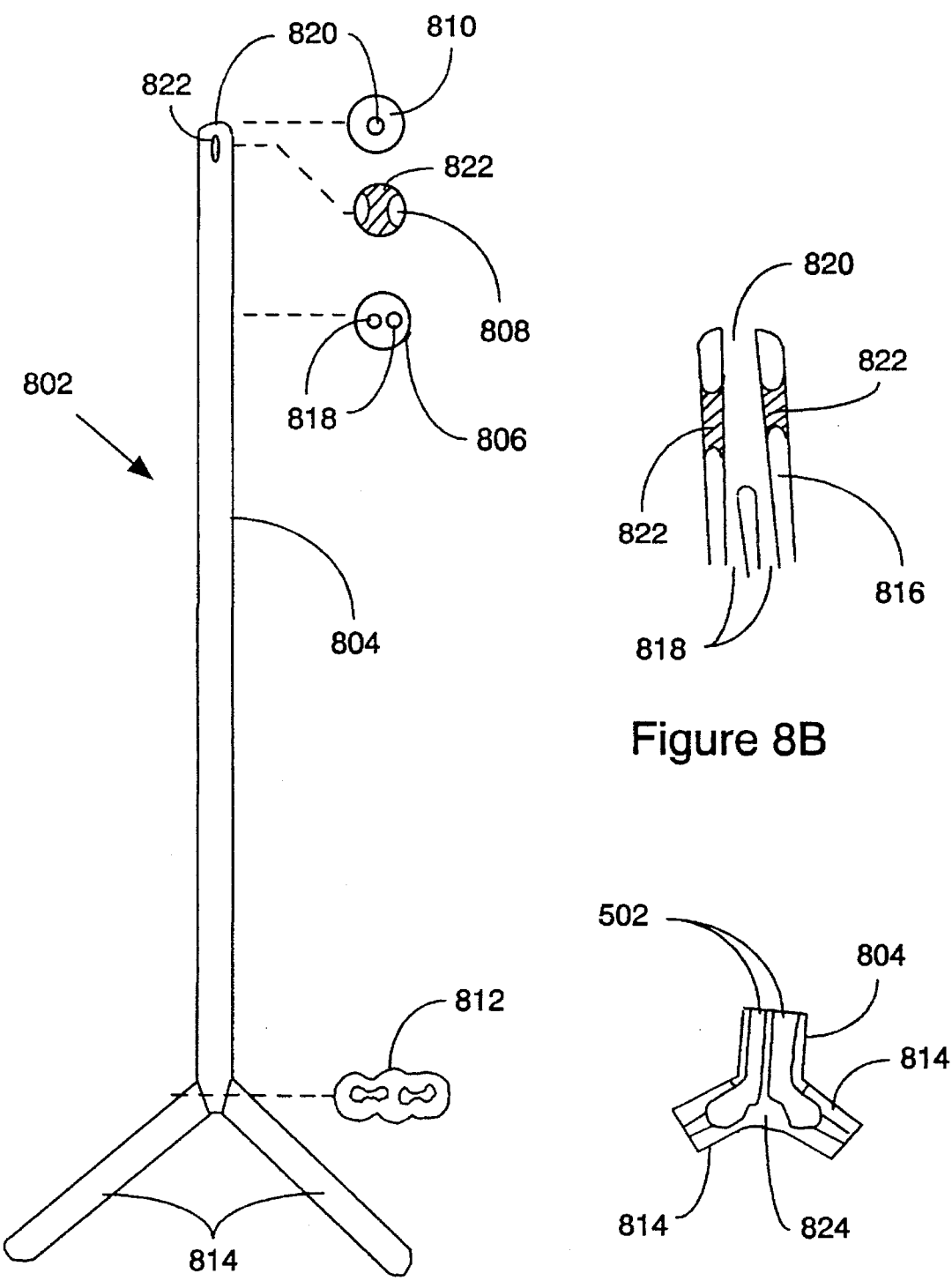
FIGS. 8A–8C are the third embodiment of the knot applier device.

Another alternate embodiment of the suture applier 802 is illustrated in FIG. 8. Like the other embodiments discussed above, this ligator device is designed to separately manipulate lengthened suture strands from outside the body cavity in order to effectively apply locking slip knots and further secure them with extracorporeal hitch knots. Cross sectional views A, B, and C illustrate the internal structure of the suture applier 802. Its shaft 804 has dual channels 818 that each accommodate a suture strand (not shown). The dual channels 818 are shown in a sagital sectional views in FIG. 8B. Side openings 822 which connect to create a transverse channel (e.g., an interior space) are shown in the side view of the device. FIG. 8A shows a cross sectional view 808 of side openings 822. The sagital cross sectional view shown in FIG. 8B illustrates how one of the suture strands of a hitch knot may be inserted into side opening 822 and then extracted through the other side opening 822. One of the side openings 822 is larger than the other to provide an oblique direction on the suture strand that is loaded through them when pushing a knot. This facilitates advancement of the knot through a narrow cannula. As shown in FIG. 6, the surgeon holds together the proximal part of the two suture strands on the left hand, leaving 2 or 3 centimeters longer the one that was loaded on the ligator. In addition, the tension on the sutures distal to the knot is released while the knot is being pushed in order to help the knot advancing and to avoid pulling the sutures off the tissues. This allows the instrument to be used as a closed end knot pusher when adding hitch knots to secure the tie. Cross sectional view 810 shows distal opening 820 at the distal end of suture applier 802. Cross sectional view 812 shows channels 818 at the entrance to breakable portions 814. The narrow width of the channel 818 in cross section 812 shows a method of taughtly holding the suture on the breakable portions. When loaded with one of the Lehrer locking knots, the sure-tie ligature system can effectively deliver a secure first tie. Using the same ligator as a knot pusher, this tie may be further secured with one or more extracorporeal knots. In the preferred embodiment, the shaft 804 is 27-cm long with two additional 3-cm long, separate breakable portions 814. Those skilled in the art will recognize that the lengths are not critical and may vary for convenience to suit a particular surgical procedure.

The slip knot (not shown) is kept centered on the tip of the suture applier 802 and its two suture strands 502 are threaded through a single or double distal opening 820 that does not accommodate the knot. The channels 818 diverge in shaft 804 at bulge 824. Separate breakable plastic portions 814 hold the ends of the sutures and are color coded to distinguish the end portion of the suture from the standing part. In the preferred embodiment, the portion holding the standing part is color coded green and the end portion is color coded red. A slot 822 of approximately 1 mm diameter is made on each side at approximately 2 millimeters from the tip of the suture applier 802 to adapt it for use as a closed-end knot pusher to apply additional extracorporeal knots. A snare wire may be enclosed to help loading the suture strands on the device.

A variety of suture materials and suture sizes could be used, from microsutures to larger suture materials. In the preferred embodiment, suture applier 802 comes with one of the previously described locking simple slip knots, or with the double noosed slip knot. The ready-made slip knot is placed on the mid-portion of a 36-inch suture.

The method used with suture applier models 402, 702, 902, 1002, and 1302 to hold the slip knot for insertion through the cannula is designed to prevent the noose from getting accidentally closed by the drag that the seal of the cannula produces on the knot itself and/or on its suture strands. That may have been one of the reasons to design the prior loop ligatures with a shortened end portion. However, the benefits of making a slip knot with a long end portion far outweigh the above potential drawback by allowing the effective use of self locking slip knots and of an easier extracorporeal technique for making additional security knots. A slip knot that has long suture strands may also be inserted through a cannula by the alternative method of grasping it with a suture grasper at the point where the end portion strand is the closest to the knot.

Instrument model 1702 requires an additional introducer sleeve 436 to completely enclose the two suture strands of the slip knot and noose. The noose is extruded past the distal end of the ligator device and is enclosed in its entirety within the introducer sleeve before introducing it through the cannula. Further, suture appliers 402, 702, 802, 902, 1002, or 1302 can be used, as discussed earlier, to apply either a loop ligature or a suture ligature. In the later situation, the suture applier 402, 702, 802, 902, 1002, or 1302 is first used to tie the first throw of the suture, using an extracorporeal technique. The suture ligature is tied by manipulating the suture strands extracorporeally and using either one of the two aforedescribed needle-through-noose techniques to tie a suture ligature, forming a secondary noose. These models of the ligature device can also be used with one of the two pretied knot suture techniques. In the needle through noose technique, the suture needle is first passed through the tissues and then through the noose of the slip knot, creating a secondary noose. The secondary noose is then locked with three or four extracorporeal hitch knots using the suture applier 402, 702, 802, 902, 1002, 1302 which is being used as a knot pusher. With this technique of suture ligature, the needle may be attached to the end portion strand or to the standing part. Two other techniques use one of the knots that have been pretied after the standing part with a needle attached to it has been drawn out of the loops of the slip knot. These techniques will be discussed more fully below in regard to FIGS. 14, 15 and 16.

Figure 9:
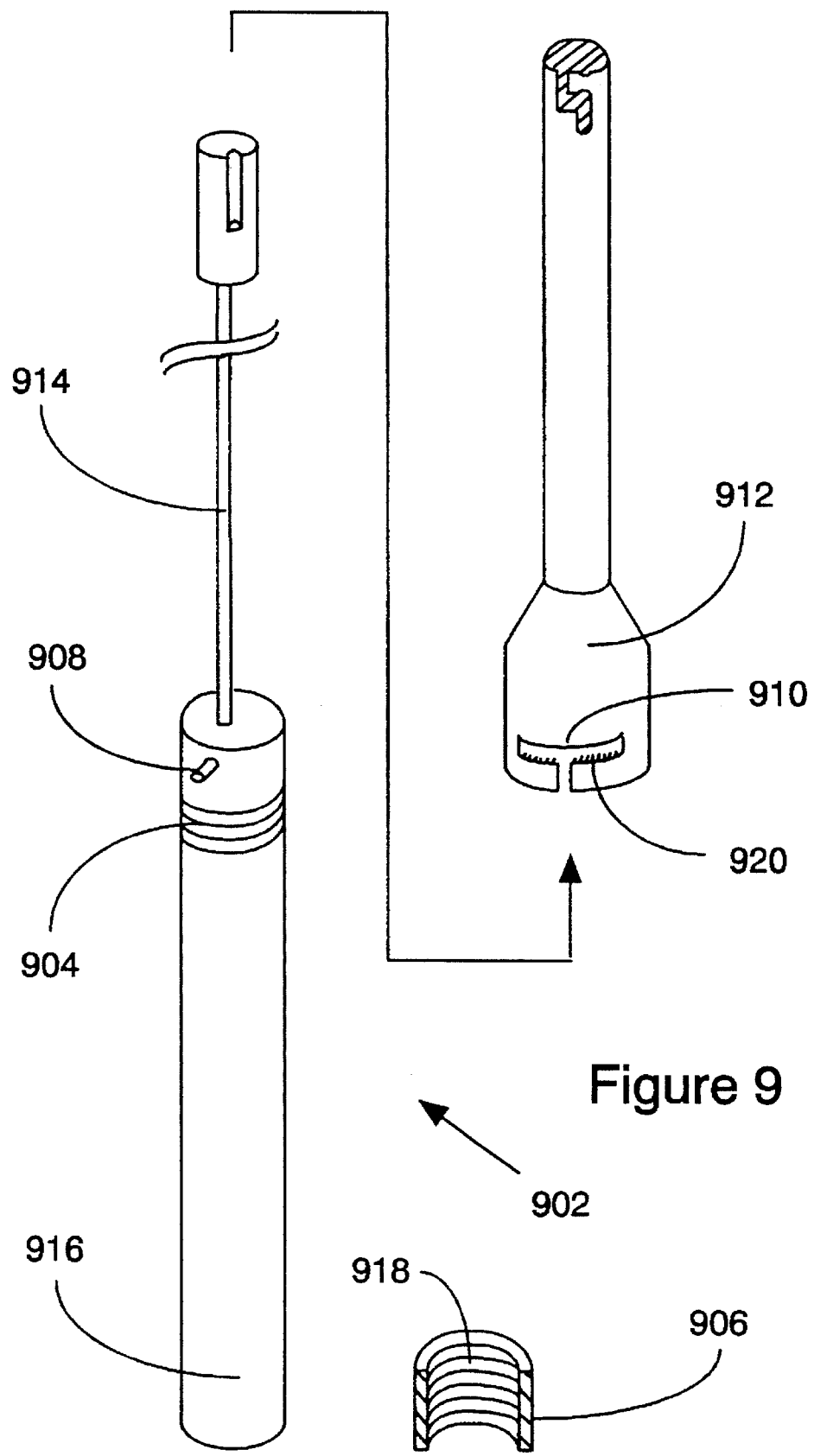
FIG. 9 is a fourth embodiment of the knot applier device.

FIG. 9 shows another alternative embodiment. In this embodiment, sheath 912 is mounted on shaft 914. Retainer 908 (which is fixed to shaft 914 in the preferred embodiment) enters slot 910 and is held in place by means of a pressure nut 906 (shown in cross sectional view to expose the inner threads 918). The pressure nut fits over the proximal end of the handle and engages threads 904, pushing the proximal end of sheath 912 forward, compressing the retainer 908 against slot 910, thus holding the setting mode. In the preferred embodiment, the proximal edge of slot 910 is notched with many small serrations 920 to accommodate a variety of positions without slippage of retainer 908 when it engages slot 910. This embodiment allows a variable number of positions to be set. By so doing, multiple sizes suture material may be grasped by a single suture applier. However, the distal opening between shaft 914 and sheath 912 must be adjusted to hold the knot outside the suture applier 902 by manufacturing devices that have an indentation 404 of various sizes at the distal end of shaft 914.

In this embodiment, the indented edge 404 is made narrow and shallow, and has a transverse extension 922 that gives it the appearance of an L-shaped groove with a curved elbow. This alternate indented edge on the surface of the shaft at its distal end is discussed below in more detail, in relation to FIG. 12, and is also shown on FIGS. 10, 11 and 13.

Loading one or two suture strands into the ligator instrument requires that when it is set in the open mode, the opening formed between the indented surface 404 of the shaft and the sheath 912, extends between distal opening 924 of that space and the proximal arm 926 of the slot of the sheath 912. This requirement is achieved with a transverse extension 922 of the indented edge 924. The resulting L-shaped indented edge at the distal end of the internal shaft is shown in FIGS. 9, 10, 11, 12 and 13.

Notice that stub 928 is square on the proximal end. This lies above the rounded elbow of indented surface 922, and provides a lip for swinging the suture strands towards the distal end of the sheath 912 for easier loading.

Figures 10, 10A:
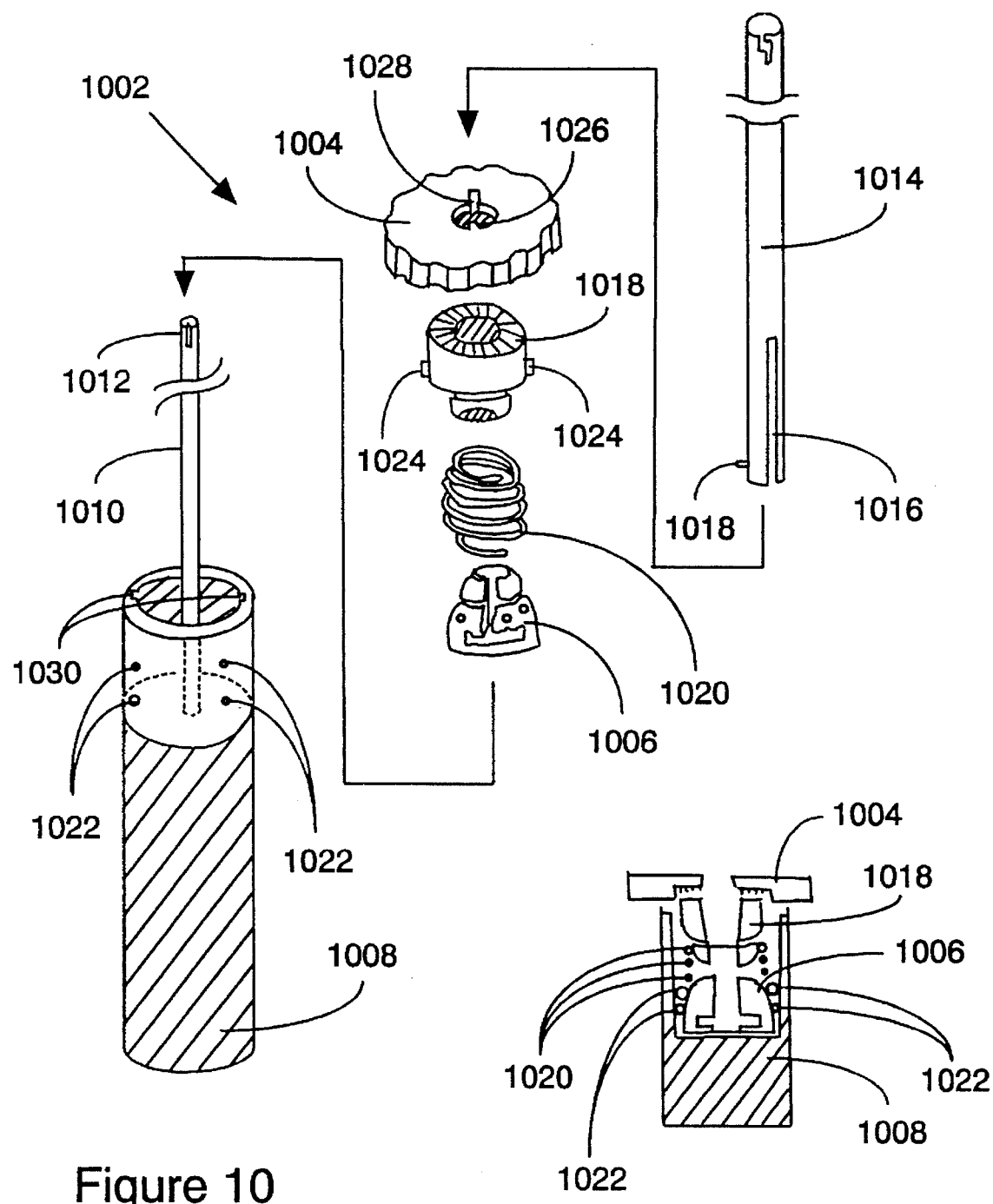
FIGS. 10A–10A are the fifth embodiment of the knot applier device.

FIG. 10 illustrates a second embodiment which also allows a variable number of positions to be set on the distal end of the instrument. In this embodiment, slot insert 1006 is sized such that a portion of the internal space of handle 1008 is taken. The remaining portion is used by the clicker assembly 1018 and spring 1020. Wheel 1004 is positioned above handle 1008. Clicker assembly 1018 has teeth on the distal surface which fit into a recessed portion of wheel 1004 which has a corresponding set of teeth. Sheath 1014 is inserted through wheel 1004, clicker 1018, spring 1020, and slot insert 1006. Sheath 1014 is then mounted over shaft 1010 and its proximal retainer 1018 enters into slot insert 1006. Holders 1022 in turn hold slot insert 1006 in place. Holders 1022 may be screws, rivets, glue, or any other appropriate method of retaining slot insert 1006 in place. Clicker retainers 1024 fit into handle slots 1030 preventing its rotational movement while allowing it to move in a distal or proximal direction. Clicker 1018 is pressed against wheel 1004 by spring 1020. Wheel 1004 in turn is held in position by the key 1026 which fits into slot 1016 of sheath 1014 which in turn is held within the transverse portion of the slot of slot insert 1006 which is in turn fixedly attached to the handle 1008. When wheel 1004 is rotated, clicker 1018 is compressed against spring 1020 and snaps from tooth location to tooth location.

Insert A shows a cross sectional view of wheel 1004, clicker 1018, spring 1020, and slot insert 1006 as aligned in handle 1008.

Figure 11:
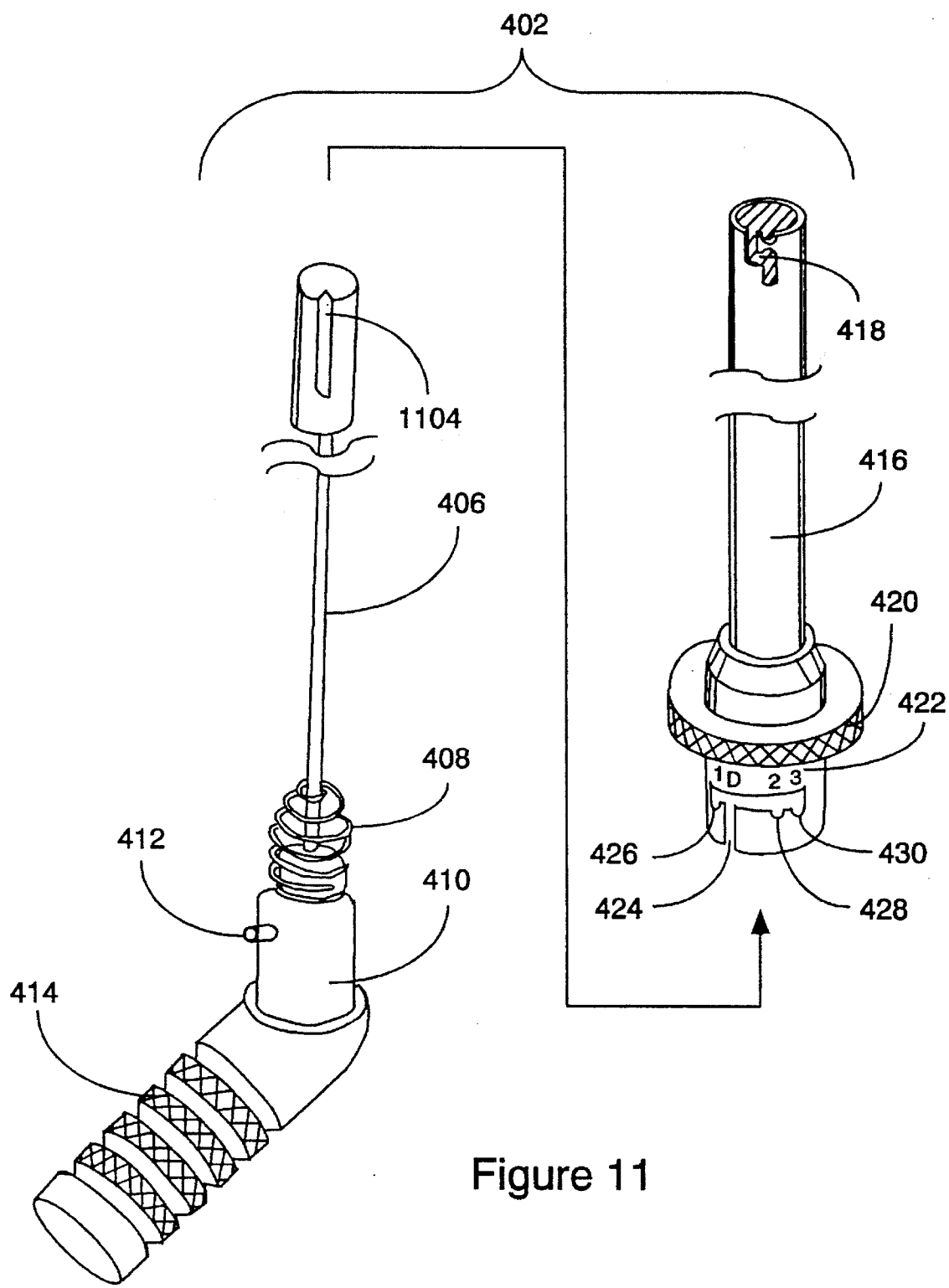
FIG. 11 is an alternative embodiment of the ligator device disclosed in FIG. 4.

FIG. 11 illustrates an alternative embodiment of the device shown in FIG. 4. In this embodiment, the indented surface 404 is shaped as a distal groove 1104. Groove 1104 is discussed below in more detail in the discussion of FIG. 12.

Figure 12A:
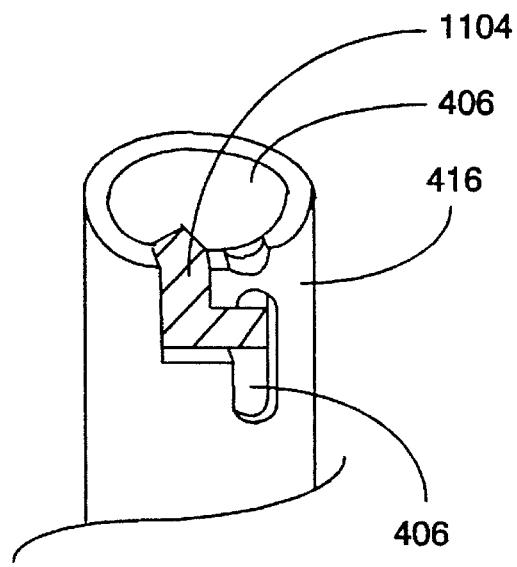
FIGS. 12A–12C are detailed view of the distal end of the ligator device of FIG. 11.
Figure 12B:
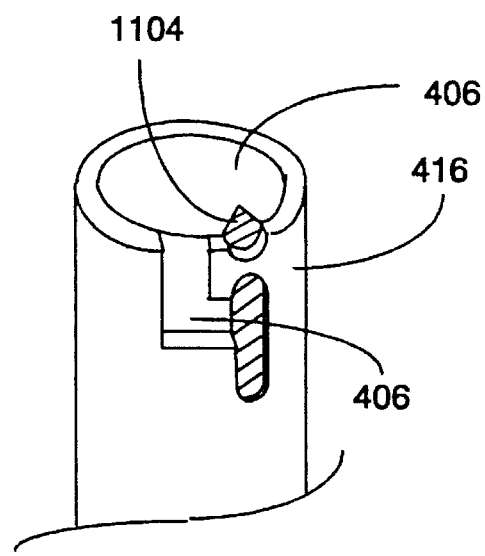
Figure 12C:
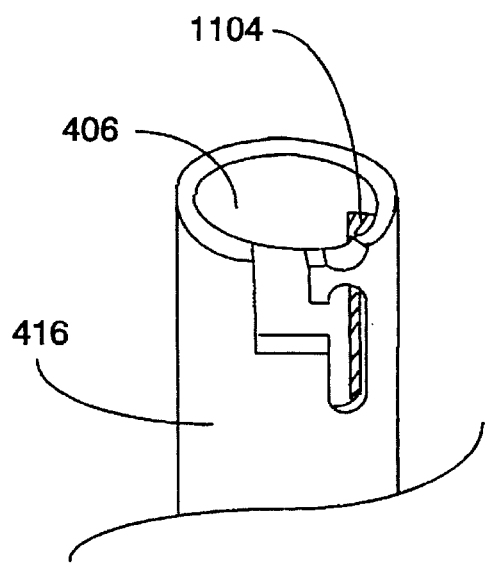

FIG. 12 is an enlarged view of the distal end of the device shown in FIG. 11 showing the three positions of the device. As can be seen when compared with FIG. 5, the groove 1104 provides a smaller area for a suture and reduces the possibility of a suture knot becoming lodged between the shaft 406 and the sheath 416, and allows smaller knots to be used.

Figure 13:
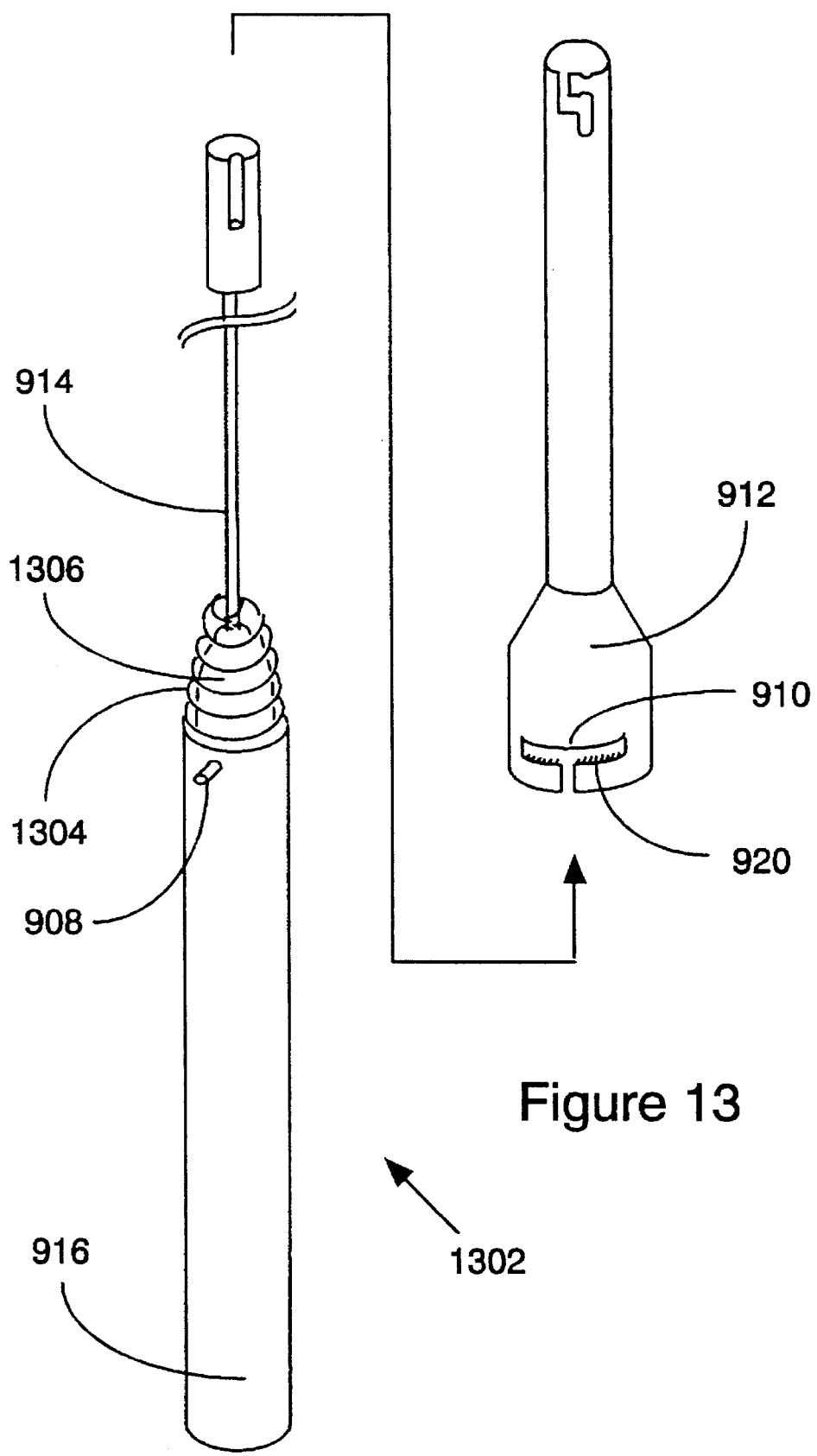
FIG. 13 is an alternative embodiment of the ligator device shown in FIG. 9.

FIG. 13 is an alternative embodiment of the ligator applier 902 discussed above in relation to FIG. 9. In this embodiment, pressure nut 906 and threads 904 are replaced by spring 1304 which mounts over widened base 1306.

Suture appliers 402, 702,802, 902, 1002, or 1302 can be used, as discussed earlier, to apply either a loop ligature or a suture ligature. In the later situation, the suture applier 402, 702, 802, 902, 1002, or 1302 is used to tie the first throw of the suture, using an extracorporeal technique and an extracorporeal slip knot.

Figure 24:
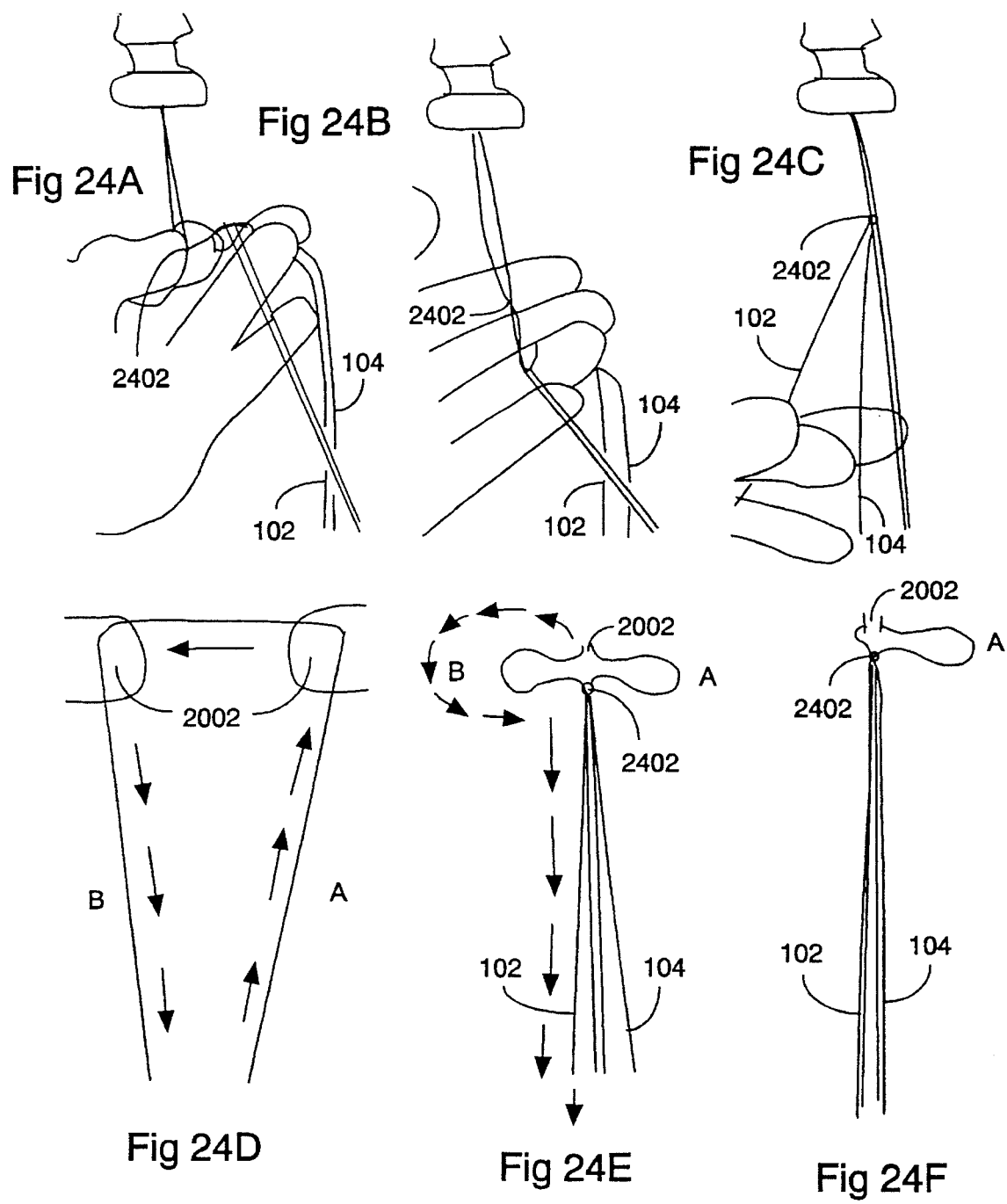
FIGS. 24A–F show a technique to load the ligator device and tie an extracorporeal slip knot.

FIG. 24 illustrates the technique to load the slip knot on the ligator device 402. The slip knot is loaded on the knot applier 402 by its two suture threads, in such a manner that the knot is positioned distal to the top opening 502 of suture applier 402; and the two suture threads exit the instrument through its distal side opening 504.

(A) The slip knot 2402 is loaded by its two suture strands, which are introduced first through the transverse arm of the slot 418, as shown in the picture; and then, through its longitudinal arm. The two suture strands must fit within the indentation 1104 and 922 of the shaft 406 allowing to change the open setting to the enclose setting of the ligator instrument.

(B) In the enclose setting, the two suture strands can be manipulated from outside the body cavity, sliding them through the distal segment of the instrument.

© The slip knot is held at the tip of the ligator instrument. "Sawing" on the tissues may occur if the standing part is pulled while keeping the knot at the maximal distance from the tissues, which is contrary to the recommended technique.

Before continuing with the discussion in FIG. 24 regarding the sawing effect that a slip knot may produce on tissues upon initial tightening, the following concepts regarding the tying of suture ligatures may be applicable in minimizing the trauma to the tissues.

When applying a slip knot, the ligator instrument is not used a "knot pusher". Slip knots cannot be pushed because the loops of the end portion strand that form the knot have already been tightened to form the noose. Hitch knots may be pushed only while still open. In fact, slip knots are held at the tip of the ligator device while the standing part is pulled through the knot itself to effect the closure of the noose.

Moreover, the position of the knot relative to the suture strand is not necessarily related to the spacial positioning of the knot, which is held on the tip of knot applier device 402 and is positioned with it. The sawing effect on tissues may be minimized by bringing the tip of the device to touch the target tissues, holding the knot in that position before pulling the standing part suture to close the noose.

(D) The non-recommended technique is shown: the surgeon is closing the noose with the standing part while keeping the knot at a maximal distance from the tissues. The afferent 2404 and efferent 2406 segments of the noose have a similar length and are being simultaneously mobilized through the target tissues, pulling and producing a "sawing effect" on the tissues.

(E) In contrast to the above technique, before pulling the standing part, the tip of the ligator instrument that is holding the slip knot was advanced to bring the knot to touch the target tissues, thus creating a slack on the afferent and efferent segments of the noose.

(F) Half of the noose has been closed by gently pulling its efferent segment past the knot while its afferent segment remains unchanged. This step was accomplished without mobilizing any length of suture through the tissues, and therefore, there was absolutely no "sawing effect". This effect will be minimized because of the smaller size noose that remains to be gently closed on the tissues and the reduced tension of the suture that is brought about by the proximity of the knot to the tissues, which may be gently supported with the tip of the instrument.

The techniques to tie a suture ligature include using an extracorporeal slip knot that may be made by the surgeon, as shown on FIGS. 19 and 20; a pretied loop suture; a pretied knot suture that completes the slip knot outside the body cavity, as it was already discussed in reference to FIG. 16; and a pretied intracorporeal knot suture that will be discussed more fully below in regard to FIGS. 14 and 15.

The knot applier 402, 702, 802, 902, 1002 and 1302 can be used with the pretied loop suture technique. It's advantage is that the same instrument can be used to secure the secondary noose with three or four extracorporeal hitch knots.

Figure 14:
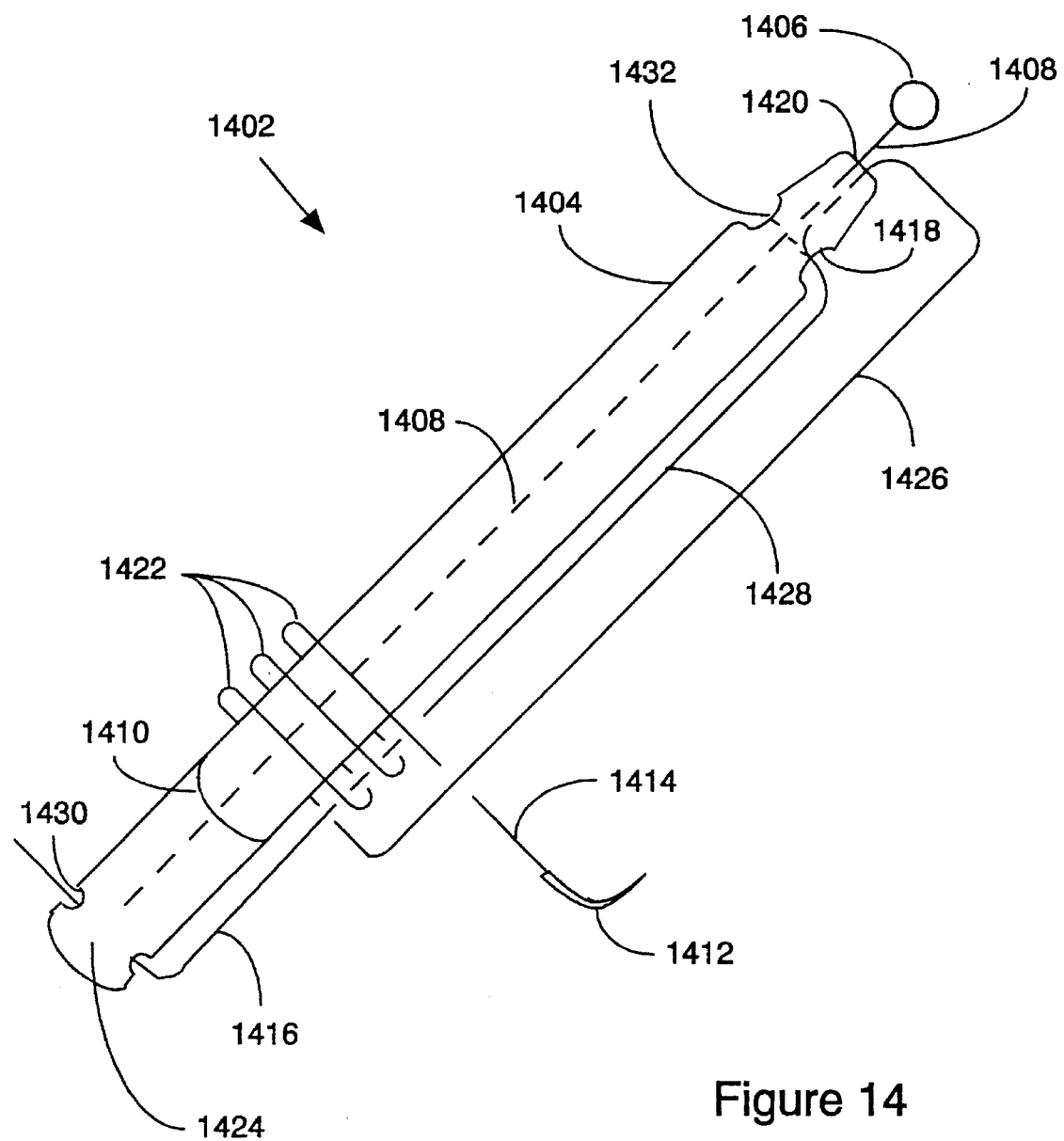
FIG. 14 is an alternative embodiment showing a pretied knot suture that comprises a disposable ligature applier with sutures mounted on its shaft. The pretied loops of the first Lehrer knot are shown. This knot having its step 4 omitted and the standing part suture pulled out of the loops of the knot. This embodiment may be used to intracorporeally form a slip knot by manipulating lengthened sutures from outside the body cavity. The reduced size of the resulting noose allows the slip knot to be applied without a sawing effect on the tissues.

FIG. 14 is a disposable embodiment of the ligator applier 1402. For ease of illustration, the diameter of shaft 1404 is shown greatly enlarged in relation to the length to better illustrate the structure of the device. Also, the suture which is comprised of end portion 1416 and standing part 1414 is shown with a relatively short length to eliminate clutter in FIG. 14.

Suture applier 1402 is used with a pretied knot suture that is designed to intracorporeally complete a slip knot that has a small noose which might be tied without producing a significant sawing effect on the tissues. An initial discussion of suture applier 1402 as it is configured prior to use follows. The preferred knot is the first Lehrer knot which is fashioned as outlined above in the discussion of FIG. 1, preferably without the second hitch produced by step 4. The suture needle 1412 is attached to the standing part 1414 of the suture which is pulled back through the knot 102, undoing the noose but leaving the pretied loops of the knot 1422.

The method to load these loops on the ligator instrument is as follows. The first step consists of introducing the end portion 1416 through the opening 1420 on the distal end of suture applier 1402, which has an interior channel of a size sufficient to accommodate both the end portion 1416 and guide wire 1408. Then the end portion 1416 exits through side opening 1418.

The second step consists of mounting pretied loops 1422 over the shaft 1404 loosely enough such that they may slide along the surface of shaft 1404. These pretied loops 1422 are placed proximal to the side opening 1418. This creates two external loops 1426 and 1428. These loops 1426, 1428 are part of the end portion of the suture. Loop 1426 extends from the third pretied loop to opening 1420 on the distal end of the ligator. Loop 1428 extends from side opening 1418 to the end of the end portion 1416 passing within the first two distal pretied loops. By pulling the loop 1426, the pretied loops can be loosened of the shaft 1404 and can be displaced toward the proximal end of the ligator dragging the end portion of the suture into the suture applier. Conversely, pulling the end portion of the suture 1416 mobilizes the external loop 1428 and the pretied loops 1422 are displaced toward the distal end of the ligator and can be pushed over its end. This method allows extracorporeally pulling the pretied loops over the standing part 1414, once the suture needle 1412 is passed through the tissues and then through the loop 1406 of the guidewire 1408, and after the standing part 1414 has been pulled out of the abdominal cavity using the guidewire 1408. Outer sleeve 436 is used to push the loops off the distal segment of the device. Guidewire 1408 forms a loop 1406 at the distal end. Guidewire 1408 is fixedly attached to the breakable portion 1424 of suture applier 1402. Further, guidewire 1408 is shown as a dashed line to indicate that it is within the internal channel of shaft 1404. Breakable end 1424 of shaft 1404 may be disconnected from shaft 1404 by breaking shaft 1404 at weakened point 1410. End portion strand 1416 is loaded through aperture 1430 when to assist in backloading the device into an introducer sleeve.

In the preferred embodiment, a large curved suture needle 1412 is slightly flattened to facilitate its introduction through a size 10 laparoscopic cannula. Of course, other sizes of suture needles may also be used, including small suture needles used for microsurgical procedures that can be performed laparoscopically.

The following discussion details the method in which suture applier 1402 is used. Standing part 1414 is introduced via a cannula into the body cavity along with suture needle 1412. After suture needle 1412 passes through the target tissue, the loop 1406 at the distal end of suture applier 1402 is brought in proximity with suture needle 1412 which is then passed through the loop and cut off the suture after passing two or three centimeters of the suture through the loop 1406. Breakable end 1424 of suture applier 1402 is broken at weakened point 1410. End portion strand 1416 is loaded through aperture 1430 when to assist in backloading the device into the introducer sleeve 436 that was discussed in relation to FIG. 4, which may be used to assist in pushing the loops 1422 off the distal end of the suture applier 1402. Guidewire 1408 is pulled through shaft 1404 taking with it standing part 1414. Guidewire loop 1406 deforms to fit through the internal channel of suture applier 1402.

Standing part 1414 emerges at the proximal end of suture applier 1402, and is pulled such that about three centimeters of standing part suture extends from the distal end of the ligator to the tissues. At this point, pretied loops 1422 may be advanced toward the distal end of suture applier 1402 by pulling on the proximal end of end portion 1416 and by pushing the loops with the introducer sleeve 436. Pretied loops 1422 will slide off the end of suture applier 1402 in close proximity to the target tissue where the small noose of the knot so formed may be tied and locked by manipulating the suture strands from outside the body cavity, avoiding any significant degree of sawing effect on the tissues. After tying the slip knot, security knots may be added by the surgeon to ensure that the knot does not loosen. One or more hitch knots are fashioned extracorporeally using the standing part of the slip knot which is then introduced through side openings 1418 and 1432. The surgeon holds the suture strands with one hand while advancing the hitch knot with the instrument using the other hand.

By moving the pretied loops 1422 along shaft 1404 in this manner, the knot can be formed in close proximity to the target tissues. This knot has a small size noose and as a consequence, less suture material must be drawn through the target tissues, thereby reducing the tissue damage caused by the sawing effect of prior art methods. In addition, the preferred embodiment uses any of the locking knots discussed above, preferably the first Lehrer knot with or without the distal hitch created with step 4. However, the triple hitched (second, third and fourth Lehrer knots) knots should not be used because the pretied loops cannot be advanced over the distal end by pulling the end portion suture. The surgeon may elect to add additional security knots to lock the tie. While delivering the knot to the tissue rather than pulling a large amount of suture material through the tissue to form the knot extracorporeally, a large noose is eliminated which decreases the trauma to the tissues. In addition, the use of additional security knots reduces the total number of suture ligatures required. This, in turn, reduces the total amount of trauma to the tissue.

Figure 15:
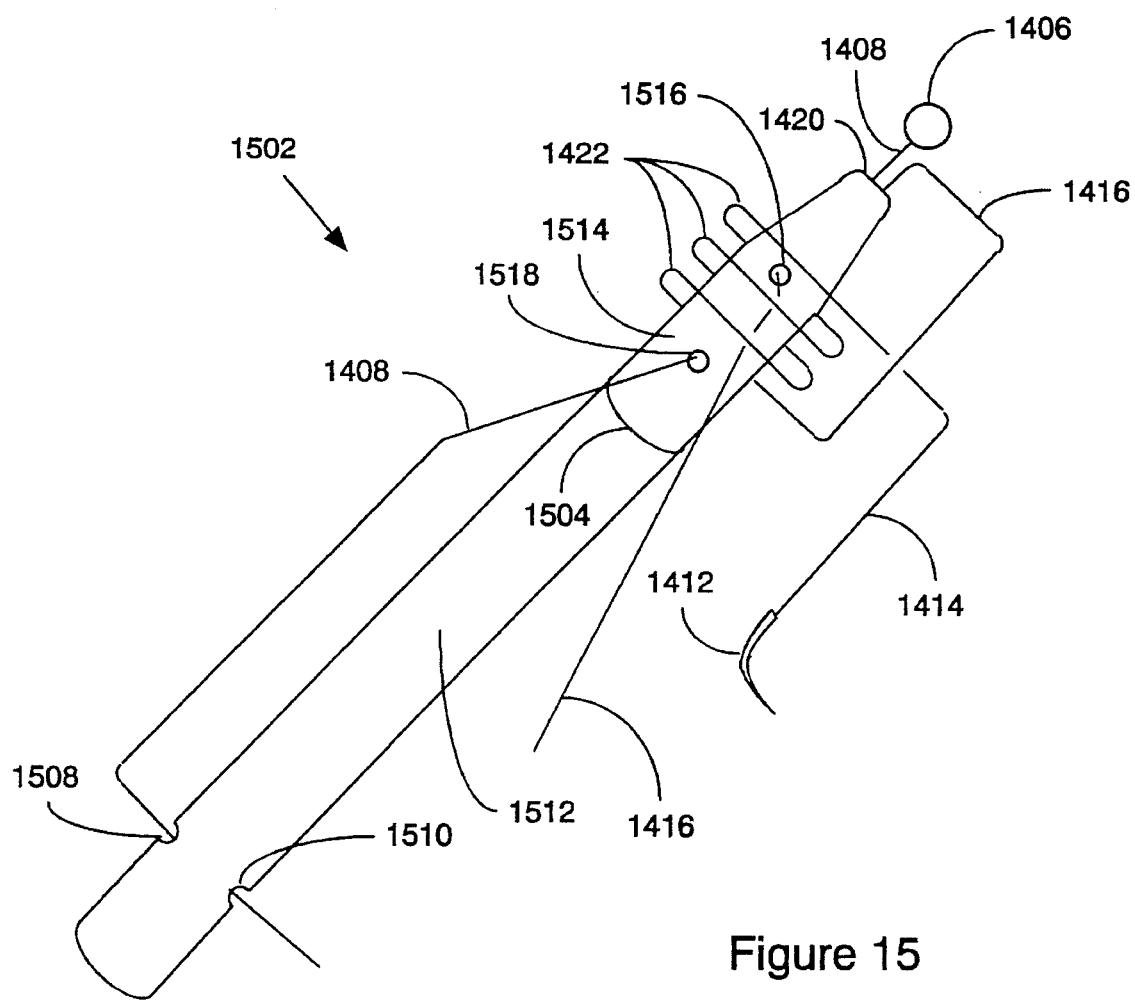
FIG. 15 is an alternative embodiment of the ligature applier in FIG. 14 which has a reusable proximal end.

FIG. 15 shows an alternative embodiment of the suture applier shown in FIG. 14. In this embodiment, the longitudinal and transverse channels of the device are restricted to the distal 1.5 to 2 cm of the ligator device, approximately; and there is an additional side opening 1518 which is continuous with the proximal end of the aforementioned distal longitudinal channel. Most of shaft 1512 is solid, except for its distal 1.5–2 cm approximately, which may form one body with it; or may constitute a separate disposable portion 1514. In the later case, proximal end 1512 and distal end 1514 are joined at shaft connection 1504. The two ends of the suture applier 1502 may be joined by any suitable method, such as snap on connectors, screw connectors, etc. For a more detailed discussion of the angles used in the transverse channel, refer to the section below which describes FIG. 17C, which is similar in structure to the device of figure 15. In this embodiment, pretied loops 1422 are loaded onto the portion of the distal end 1514 that is distal to third side opening 1518. End portion 1416 enters the internal channel of distal end 1514 at opening 1420 and exits at opening 1516. Side opening 1516 is one of the two openings of a distal transverse channel in the preferred embodiment, having a second opening (not shown) on the opposite side of the device. Guidewire 1408 enters opening 1420 and exits at opening 1518. For ease of illustration, one internal channel is discussed as well as one distal opening 1406. However, the device can be manufactured with two internal channels and two distal openings for more convenient manipulation of certain types of materials, such as smaller sutures and suture knots. After the disposable distal end 1514 is attached to proximal end 1512, guidewire 1408 is inserted through opening 1508 and exits opening 1510 of proximal end 1512. The free end of end portion 1516 is also inserted through opening 1508 and exits opening 1510 before the surgeon proceeds to backload the ligator into introducer sleeve 436 (not shown) to effectively hold the pretied loops in place on the distal segment of the device and in preparation of insertion through the laparoscopic cannula (not shown). Once assembled, the device operates in the same fashion as the embodiment of FIG. 14. It should be noted that inserting the device through the laparoscopic cannula, the slot at the distal end of introducer sleeve 436 allows the sleeve to advance past the standing part 1414 at its exit point 1518 on the suture applier device 1402. The suture applier 1402 slidably fits within the external sleeve 436, which in turn first through a size 5 laparoscopic port. The proximal end of introducer sleeve 436 has a handle which is described more fully below in regard to FIG. 30. The seal of the cannula helps keep guidewire 1408 and end portion suture in place. The introducer sleeve may be used to push the pretied loops off the distal end of the ligator device and onto the standing part.

The aforedescribed instruments have shown a variety of ways in which the knots disclosed herein may be used. While any of the knots may be tied by hand, it would be advantageous if pretied knots could be mounted quickly on any of the instruments without the delay in the surgical procedure which occurs when knots are hand tied.

FIG. 16 discloses a spool 1602 with a pretied knot suture which allows a surgeon to quickly form an extracorporeal slip knot that can then be mounted on the suture appliers disclosed herein. The pretied loops of one of the Lehrer knots are placed on the outside of spool 1602, which is then mounted over the ligator device. The standing part which has been pulled out of the loops in a retrograde fashion has the suture needle attached to its end. The spool is slidably mounted over the shaft of the needle driver. The needle driver is then used in the usual manner, first to introduce through the cannula the suture needle by grasping the suture near the needle; second, to pass the suture needle through the tissues; and to quickly pass the standing part suture through the pretied loops of knot 1422. This later step is done by first cutting the suture needle off the standing part suture and by advancing the spool over the distal end of the needle driver. Once the spool has been advanced off the needle driver, the spool may be compressed by the surgeon. While compressed, pretied loops of knot 1422 may be slid off of spool 1602 onto the standing part suture. The knot is completed extracorporeally, tying the first two distal loops and then loosely closing the other two loops taking care not to accidentally lock the slip knot. The knot is then easily loaded on either model of suture applier 402, 702, 902, 1002, or 1302, thereby reducing the time needed to complete surgery.

In FIG. 16A, a rear view of spool 1602 is shown without a suture. Spool 1602 is made of any suitable flexible material such as rubber, plastic, etc. Spool notch 1604 is cut out to allow spool 1602 to be manually compressed such that the diameter of spool 1602 can be reduced to allow the pretied loops to slide off the spool. Those skilled in the art will recognize that while a particular slot shape is shown, any shape slot, or any other method of providing for compression of spool 1602 will work as well, so long as the spool holds the knot in the uncompressed state and allows the knot to be slid off in the compressed state.

FIG. 16B is a front view of spool 1602. Suture notches 1606 are cut at both ends to hold the suture strands. While notches are used in the preferred embodiment, any suitable method of securing the suture strands is acceptable so long as it does not interfere with the mounting of spool 1602 on any of the needle drivers commonly used in operative laparoscopy; or on the subsequent transfer of the knot from spool 1602 to the standing part of the suture ligature. Transfer of the extracorporeal slip knot to a suture or ligature applier is discussed more fully below in reference to FIGS. 16 and 24.

FIG. 16C shows a rear view of the pretied loops 1422 of the triple hitched third Lehrer knot 204 mounted on spool 1602. FIG. 16D shows a front view of the pretied loops 1422 of the triple hitched second Lehrer knot 204 mounted on spool 1602. The suture strands 1608 which extend from knot 1422 are held by notches 1606. Those skilled in the art will recognize that the size and shape of the notches are not important so long as they can hold suture strands 1608 in place. Likewise, the location of the notches on either end is not critical to the invention as they can easily be relocated so long as the strands are held in place. The preferred knot for the spool is one of the Lehrer non-locking or locking slip knots. However, other knots may be employed as well. Spool 1602 may be mounted over a needle driver or a grasping forceps.

Compared with prior art devices, such as Ethicon's Pretied Endoknot Suture, the foregoing technique simplifies the formation of the knot outside of the body cavity as follow: A) The intracorporeal steps of passing the suture needle through the loop of the guide wire; cutting the needle off the standing part suture; and pulling the loop guidewire and the suture through the internal channel of the loop ligator are eliminated. B) The spool fits over the needle driver and is designed to facilitate forming the slip knot by easily passing the standing part suture through the pretied loops and unloading them off the spool. C) Ligator instrument 402, 702, 902, 1002, or 1302 (show below in reference to FIGS. 4, 7, 9, 10 and 13) is used to introduce and apply the first throw of the suture ligature which uses a locking slip knot which can be effectively locked with the lengthened end portion suture. D) Additional extracorporeal knots may be quickly applied with the same instrument to further secure the tie in a manner that is more efficient than intracorporeal knot tying.

Conversely, the prior art pretied knot sutures are single use devices that employ a guidewire loop to bring the standing part suture out of the body cavity, passing it through the internal channel of the ligator instrument and through the loops that are pretied on its shaft. The intracorporeal steps involved are unnecessary, because the needle driver that will be used anyway to remove the suture need through the cannula, can also be used to remove the standing part at that time, without resorting to the guidewire. Passing the standing part through the pretied loops is better accomplished outside the body cavity using the needle driver and spool. Therefore, the intracorporeal steps of the prior art referred above are unnecessary and cumbersome, because the knot will be formed outside the body cavity, anyway. In addition, the prior art ligator device can not be used with hitch knots or with a Surgeon's Knot or as a knot pusher. The first throw made with the slip knot is unlocked and a more time consuming intraperitoneal technique to make a security knot is required by the prior art.

Figure 17A:
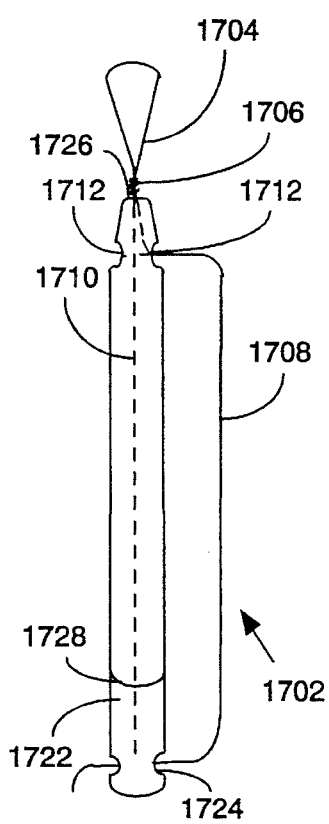
FIGS. 17A–17C show a loop ligature applier and knot pusher that has included an integral loop ligature with elongated suture strands and one of the Lehrer knots in ready made form. This figure also shows an alternative embodiment of the loop ligature applier and knot pusher that is most cost effective, and an alternative embodiment of the introducer sleeve.

FIG. 17A shows a greatly simplified embodiment of the ligator device which may be used as an alternative to the devices described in relation to FIGS. 4, 7–11, and 13–15. In the preferred embodiment, one of the self locking Lehrer knots disclosed herein is provided loosely woven and with elongated suture strands as an integral suture with the knot applier device 1702. The slip knot is preloaded by its two suture strands through the distal opening 1726 of ligator device 1702. The shaft of loop ligator applier 1702 has an internal channel 1710 which is occupied by the standing part suture 1716 which is fixedly attached to a breakable portion 1722. In addition, the distal end of the shaft has a transverse channel 1712 which communicates with the longitudinal channel 1710 and ends in two substantially diametrically opposed openings.

The distal opening 1726 accepts two suture strands plus the guidewire that is required to preload the two suture strands of the slip knot on the loop ligature device 1702. Distal opening 1726 is sized such that it does not admit the knot itself, preventing the knot from being dragged into the internal channel while the elongated suture strands are manipulated from outside the body cavity.

For ease of illustration, the standing part is described as occupying the internal channel and attached to the breakable portion. However, either suture strand could occupy the internal channel.

When the internal channel is occupied by the standing part, the end portion suture 1708 enters distal opening 1726 and exits the device through one of the side openings of transverse channel 1712. The end portion 1708 is introduced through aperture 1724 of breakable portion 1722 in order to assist in back loading the loop ligature device through the introducer sleeve 436 (shown in FIG. 17C). The external sleeve 436, an integral component of the loop ligature system, fits through a size 5 laparoscopic cannula and slidably admits the loop ligature applier 1702 and at least one of the suture strands of the slip knot.

Compared to the introducer sleeve which is used in conjunction with the ligator device that has a fasten mode, such as discussed in regard to FIGS. 4, 9, 10, 13, the introducer sleeve described for use with the device shown in FIG. 17 (which has no fasten mode) differs in that it lacks the distal groove and in that the sutures are placed within the sleeve in order to protect the sutures from the drag produced by the laparoscopic cannula during insertion of the ligator device. Before introducing the loop ligature through the laparoscopic cannula, the external sleeve 436 is advanced over the distal end of loop ligature applier 1702 to completely encase the noose which is extended forwards, past the distal end of loop ligature applier 1702. The position of the ligator device relative to the introducer sleeve must be maintained when introducing the introducer sleeve through the laparoscopic cannula. The external sleeve is introduced to approximately 4–5 cm past the distal end of the laparoscopic cannula, after which is pulled back in a retrograde direction to expose the noose.

To tie the slip knot on the tissues, breakable portion 1722 is detached at weakened point 1728 to pull the standing part suture 1716 against the knot that is held at the tip of the ligator 1702. The opening 1726 is smaller than the size of the knot to prevent the knot from entering the internal channel 1710. Care must be taken to defer pulling the end suture 1708 until after the noose 1704 has been snugly applied on the tissues to prevent accidentally locking the knot. The end portion 1708 of the suture is used to tighten the knot itself and lock it. This should be the last step in the process of effecting the tie.

Figure 17B:
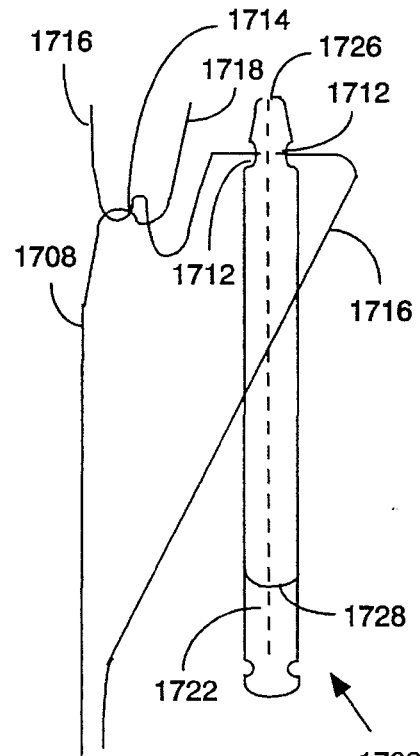

FIG. 17B shows the device when used in the preferred embodiment as a knot pusher to lock the already tied slip knot with an additional extracorporeal hitch knot. The standing part 1716 of the slip knot previously applied is used to fashion the hitch knot. The segment of standing part 1716 proximal to the hitch knot is passed through the transverse channel 1712. While holding both ends of the suture 1708 and 1716 with one hand, the surgeon pushes knot 1714 forward with the ligator 1702. The standing part of the suture 1716 is held in such manner that it is two or three centimeters longer than the end portion of the suture proximal to the hitch knot, and the traject of the sutures through the transverse channel of the ligator is slightly oblique in order to facilitate advancing the hitch knot 1714 toward the tissues.

Figure 17C:
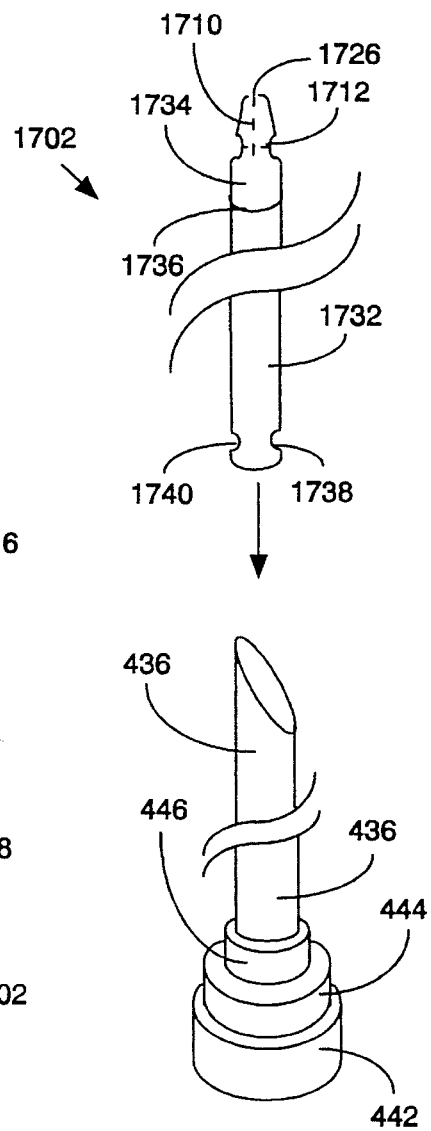

FIG. 17C shows an alternative embodiment of the loop ligature applier 1702 shown on FIGS. 17A and 17B. The embodiment which is shown in FIG. 17C is the simplest alternative to the ligator devices listed above. Similar to the device 1502 which was discussed in relation to FIG. 15, the distal portion of the shaft has a longitudinal channel 1710 which is approximately 0.2 to 0.4 cm long and extends from the distal opening 1726 of ligator device 1702 to a transverse channel 1712 which ends in substantially diametrically opposed openings.

In this embodiment, the internal longitudinal channel 1710 is made limited to the segment of the shaft that is distal to the transverse channel 1712, which connects to it. A guidewire may be provided for loading the suture strands in the device, which is relatively easy to do due to the short length of the distal channel. The shaft of the loop ligature applier is composed of either a single part, or is composed of a reusable proximal end 1732 and a disposable distal end 1734 which may be preloaded with an integral suture and sold ready to use with the suture strands coded with strand identifiers. Proximal end 1732 and distal end 1734 are joined at shaft connection 1736. The two ends of the suture applier 1702 may be joined by any suitable method, such as snap on connectors, screw connections, etc. Compared to ligator devices 402, 702, 902, 1002 and 1302, this alternative embodiment 1702 lacks the external sheath 1436 and has no mechanism to open the device for accepting the sutures; or fastening the sutures. However, there is a similarity, in that this embodiment 1702, like the other ligator devices introduced herein, is designed to deliver a slip knot with elongated suture strands which can be separately manipulated from outside the body cavity, closing the noose with the standing part, and cinching the knot to lock it with the end portion, as a final step. If the surgeon deems it necessary, the same instrument may be used to apply one or more additional extracorporeal hitch knots to further secure the tie. In this embodiment, the two suture strands of the slip knot are loaded onto distal portion 1734 through distal opening 1726; the two sutures enter internal longitudinal channel 1710 of distal end 1734 and exit through one of the side openings of the single transverse distal channel 1712, either together or separately. For ease of illustration, one internal longitudinal channel is discussed as well as one distal opening 1726. However, the device can be manufactured with two internal longitudinal channels and two separate distal openings for more convenient manipulation of certain types of materials, such as smaller gauge loop ligatures and slip knots.

In preparation of insertion through the laparoscopic cannula (not shown) loop ligator applier 1702 is backloaded on external sleeve 436 after the free end of the two suture strands of the slip knot are inserted through opening 1738 and exit through opening 1740. The seal 442 fits snugly enough over the sutures and the ligature applier 1702 to hold the sutures in place. Once assembled, the two suture strands are slidably placed between the knot applier device 1702 and the external sleeve 436.

For ease of illustration, the transverse distal channel 1712 is shown at a 90 degree angle to the longitudinal channel which extends from the distal opening to the transverse channel. However, in the preferred embodiment, the path from the distal opening to the side openings is angled to facilitate sliding the sutures by eliminating the elbow which would result if the path had a 90 degree bend or a sharp corner.

The aforedescribed loop ligature system has the following advantages:

A) It effectively delivers a loosely woven, triple hitched self locking slip knot with elongated suture strands which can be manipulated separately from outside a body cavity, first closing the noose with the standing part and then, cinching the knot to tighten and lock it with the end portion, which effectively secures the ligature;

B) This ability to cinch the knot after the noose has been applied on the target tissues allows to use self locking slip knots that are initially loosely woven to prevent the noose from accidentally getting jammed, which is a frequent problem when self locking knots are woven too tightly. The prior art loop ligature appliers lack this ability and are unable to deliver a well locked slip knot. The prior art loop ligature appliers are likewise incapable of tightening a non-locking slip knot to increase its slippage power;

C) the same instrument may be used as a closed end knot pusher to apply additional extracorporeal knots to further secure the tie, if the surgeon deems it necessary;

D) Operating the loop ligature system from outside the body cavity is easier and faster than performing intracorporeal manipulations; and provides a superior control of the tension that is applied on the sutures when tying the knot; and E) One alternate embodiment of this instrument is reusable, and has been simplified, which may translate in lower costs.

The prior art loop ligatures are single use devices and can not be used as a knot pusher with hitch knots or the Surgeon's Knot. They are provided with an integral suture which has a slip knot with an end portion suture that has been trimmed very close to the knot. As a result, the noose of the slip knot can be tied but the knot itself can not be tightened again nor locked, because this requires cinching the knot with the end portion of the suture against the knot. The surgeon is unable to restore the loss of slippage power of the knot that often occurs when the prior art loop ligatures are applied on the tissues. Therefore, the prior art loop ligatures that are currently in use are often not effectively locked and remain unsecured on the tissues.

The method used with suture applier models 402, 702, 902, 1002, and 1302 to hold the slip knot for insertion through the cannula is designed to prevent the noose from getting accidentally closed by the drag that the seal of the cannula produces on the knot itself and/or on its suture strands. That may have been one of the reasons for the faulty design of the prior art loop ligatures with a shortened end portion. However, using an introducer sleeve 436 as described above eliminates that problem. The benefits of making a slip knot with an elongated end portion strand far outweighs the above potential drawback by allowing the effective use of self locking slip knots and of an easier extracorporeal technique for making additional security knots.

FIG. 25A, 25B and 25C illustrate the use of an alternative embodiment of an introducer sleeve 456 to allow insertion of a ligator device 1702 and other instruments such as grasping forceps or suture scissors 2510. As shown in FIG. 25A, a single ligator device 1702 would be inserted through one of the slits 2504 in seal 2508 as shown while a second device such as a grasping forceps 2510 would be inserted through the other slit 2504. In this embodiment, seal 2508 is formed as a gasket, but may in fact take any suitable form capable of sealing the opening in the external sleeve 456. Cap 2502 is threaded onto coupler 2506 and holds seal 2508 firmly in place. Those skilled in the art will recognize that the number of devices introduced by introducer sleeve 456 can vary based on the size of the devices and the size of introducer sleeve 456. Likewise, the cap does not have to be attached via a threaded screw type design as shown in the preferred embodiment, but may be any suitable mechanism such as snap on, pressure fit, etc.

FIG. 25C shows a cross sectional view of the introducer sleeve 456, seal 2508, and end cap 2502. The central opening in the proximal end of end cap 2502 is smaller than the diameter of seal 2508. End cap 2502 is removably attached to the widened portion of external sleeve which forms a cap mounting attachment 2506. While the preferred embodiment uses a thread attachment, any suitable method of coupling the cap 2502 to the cap mounting attachment 2506 can be used, such as twist cap, cammed lever, etc. The seal 2504, in the preferred embodiment a gasket, is a unibody seal which is made from a central end wall which includes the slits 2504 and which is surrounded by an outer support ring. The outer ring may have an integrated support such as a metal washer or like structure, but in the preferred embodiment rests on the inner surface of the cap mounting attachment. The central end wall in the preferred embodiment is preferred to be the same diameter as the internal channel of the external sleeve but does not have to be. The central end wall has at least one slit 2504 to allow easy entry of a ligature applier 1702 or other surgical instruments while closing the body cavity to maintain the gas which has been insulated therein at pressures up to 20 mm of mercury. When the instrument is removed, the resiliency of seal 2508 automatically closes the slit 2504, such that the air tight seal is maintained at all times even when the instrument is removed. Seal 2508 may be made from any suitable elastomeric material, such as silicone, polyurethane, propypropylene, nylon, rubber, etc. In the preferred embodiment, seal 2508 is made from silicone and the slit 2504 is preferably cut such that it forms a cross with one of the slits longer than the other.

Those skilled in the art will recognize that introducer sleeve 456 and seal 2508 can be sized to allow the use of a plurality of slits 2508. By so doing, a plurality of surgical instruments can use the same introducer sleeve 456. In addition, the structure of the seal and removable cap disclosed in FIG. 25 can also be implemented on any of the embodiments disclosed herein which use a seal, such as that shown in FIG. 4. In addition, more than one seal 2508 may be used. When using a single seal 2508, its central end wall is preferably oriented towards the distal end of the external sleeve 456. When two seals 2508 are placed within the widened portion of cap mounting attachment 2506, the distally placed seal 2508 is oriented as described above; and the second seal 2508 is turned in the opposite direction with the central end wall facing the proximal end of the external sleeve 456. The interior space that is formed between the central end walls of the two seals 2508 provide a safety valve that may prevent fluid from escaping from the body cavity under pressure during insertion or removal of instruments. As a result, the dual seal 2508 structure provides enhanced safety for operating room personnel from contamination of potentially infectious body fluids such as blood. In the case of a dual seal 2508 system, either seals 2508 with thinner outer rings can be selected or the internal space between the cap 2502 and the cap mounting attachment 2506 can be designed to accommodate the two seals 2508.

FIG. 26 illustrates the distal end of a tubular device 2602 that is comprised of an inner sleeve 2606 which fits slidably and telescopically into an outer sleeve 2604. In the preferred embodiment, the fit is such that the pneuroperitoneal gas will not escape between the inner and outer sleeves 2604, 2606. Therefore no gasket or seal is required for the outer sleeve.

The term inner sleeve is used interchangeably with internal sleeve, and the term outer sleeve is used interchangeably with external sleeve throughout this application. This new embodiment shown in FIG. 26 is designed to make a knot in the proximity of the target tissues without the need of a guidewire like that used in regard to FIGS. 14 and 15. This is applicable to both pretied knot sutures and pretied knot ligatures. In addition, the new embodiment 2602 is a loop ligature applier complete with introducer sleeve and handle for easy single handed operation; and can be used to perform tubal ligation. An advantage provided by this embodiment is that a tubal ligation can be performed via laparoscopic surgery using the suture and excision method more efficiently and also with one less port, thereby avoiding the risks associated with the extra puncture required by prior art methods.

The inner sleeve 2606 combines features of the introducer sleeves and spools which were described above in the other embodiments. The similarities with the spool are as follows:

A) The internal channel accepts 5 mm instruments such as a needle driver; a grasper; or a suture scissor.

B) The suture needle is attached to the end of the standing part.

C) The pretied slip knot is prepared as follows:
  I) The noose is first undone by pulling the standing part out of the loops of the knot in a retrograde fashion.
  ii) The loops are then snug around the device and kept in place by maintaining the tension on the end portion strand.

D) The technique to use it is also similar:
  I) The target tissues are sutured with the suture needle, which is then cut off the suture. The standing part is then passed through the internal channel of the sleeve.
  ii) The pretied loops are then pushed on the standing part, forming the noose again.

Similarly to the aforedescribed embodiments of the Sure-tie Ligature Application System, inner sleeve 2604 has at least one side opening 2608 at the distal end which is sized to slidably accept at least one suture strand, but not the knot formed by the suture strands. Two or more side openings of different sizes may be placed next to one another to enhance the versatility of the new device such that a single device may be used with various suture sizes (3-0 and 2-0 sutures may require a smaller size distal side opening, as opposed to size 0 sutures). A larger size extra side opening 2614 may be made to easily load the sutures on the device when using the device as a closed end knot pusher or as a loop ligature applicator. The method used to tie and secure the slip knot with this new embodiment is the same one described above for the other embodiments of the Sure-tie Ligature Application System.

An advantage of this device as a loop ligature applicator is that the inner channel 2618 formed by the inner sleeve 2606 is large enough to allow the introduction of 5 mm devices such as needle drivers, graspers, suture scissors, etc., thereby reducing the number of required access ports (i.e., punctures) to accommodate laparoscopic cannulas into the body cavity.

Described in the discussion of FIGS. 14 and 15 is an introducer sleeve which is used to push the pretied loops off the ligature applicator device and over the standing part suture. This concept is extended to this new embodiment, which like the embodiments of FIGS. 14 and 15, use an outer sleeve to discharge the pretied loops of the knot off of the distal segment of the inner sleeve and make the knot in the proximity of the target tissues. An advantage of this device as a pretied knot suture applicator is that the internal channel 2618 eliminates the need for a guidewire, and therefore efficiency is improved. Outer sleeve 2604 on this new embodiment may be advanced beyond the distal end of inner sleeve 2606 to enclose the noose of a loop ligature in preparation to introducing it into a body cavity through the laparoscopic cannula. The loop ligature is loaded in the instrument by inserting both suture strands through the side opening 2614 from inside out such that the strands are outside of inner sleeve 2606 and also exit through slot 2616 in outer sleeve 2604.

Shown in FIG. 26A is distal slot 2616 of outer sleeve 2604. Slot 2616 can be aligned with side opening 2608 or 2614 and is designed to allow outer sleeve 2604 to be advanced past the distal end of inner sleeve 2606 without damaging the suture strand which is inside openings 2608 or 2614. The length of distal slot 2616 matches the length of proximal slot 2818 which controls the forward movement of outer sleeve 2604, as will be described in connection to handle elements 2802, 2804, 2806, 2808, and 2812. This figure also shows side openings 2620, 2622 in outer sleeve 2604 which allow loading the slip knot by its two suture strands on the outer sleeve from inside out like it can also be done on the inner sleeve 2606. The advantage provided by this embodiment is that the laparoscopic tubal ligation can be performed using the suture and excision method more efficiently and also with one less port, thereby avoiding the risks associated with the extra puncture required by prior art methods. The procedure is performed as follows. A grasper which was previously introduced into the noose of a slip knot that was loaded on the outer sleeve 2604 is used to grasp a knuckle of the fallopian tube. Outer sleeve 2604 is advanced over the distal end of inner sleeve 2606 and the knuckle of the fallopian tube, and the noose of the slip knot is then closed around the knuckle of the fallopian tube. The ligator device is then used as a knot pusher to deliver one or more extracorporeal knots to secure the tie. A suture scissors is introduced through the internal channel 2618 to excise the knuckle of the tube and cut the suture after which the specimen is retrieved.

As shown in FIGS. 26B and 26C, the side openings 2608, 2614, 2620 and 2622 are sized such that a knot will not fit within them, thereby avoiding the possibility of having the knot stuck in the side openings 2608, 2614, 2620, 2622. As can be seen, the diameter of the side openings 2608, 2614 can vary. In addition, side openings 2620, 2622 are oriented in the same manner as side opening 2608, 2614 to facilitate handling of suture strands.

The preferred embodiment envisions side openings 2608 and 2614 as being placed as distally as possible, such that the opening is at the top end of the inner sleeve's 2606 wall if its size is sufficiently small to fit there. In addition, the side openings 2608, 2614 are slanted to better accommodate movement of the suture strands though them while at the same time preventing the knot from entering side openings 2608, 2614. The angling of the distal end of inner sleeve 2606 is designed to facilitate insertion of suture strands into side openings 2608, 2614 from inside out. In addition, it provides a larger surface to center the entrance of the side opening on the top end of the inner sleeve 2606 leaving enough thickness of material around the opening which can be shaped to prevent the knot from entering the side opening 2608, 2614. One effective way to minimize the chance that the knot will slip into side opening 2608, 2614 is to angle side openings 2608, 2614 such that sutures enter the distal surface of the inner sleeve 2606 at approximately a perpendicular angle and exit the side opening 2608, 2614 on the side of the inner sleeve 2606 at an oblique angle. Likewise, in the preferred embodiment, side openings 2608 and 2614 are rounded at the edges and angled to prevent snagging suture strands.

FIG. 26A also shows two shallow and rounded grooves 2612 are made on the edge of the distal end of the device which are placed in alignment with one of the distal side openings 2608, 614. Grooves 2612 are used to catch the suture between the tissue and the instrument when additional locking knots are applied.

Figure 27:
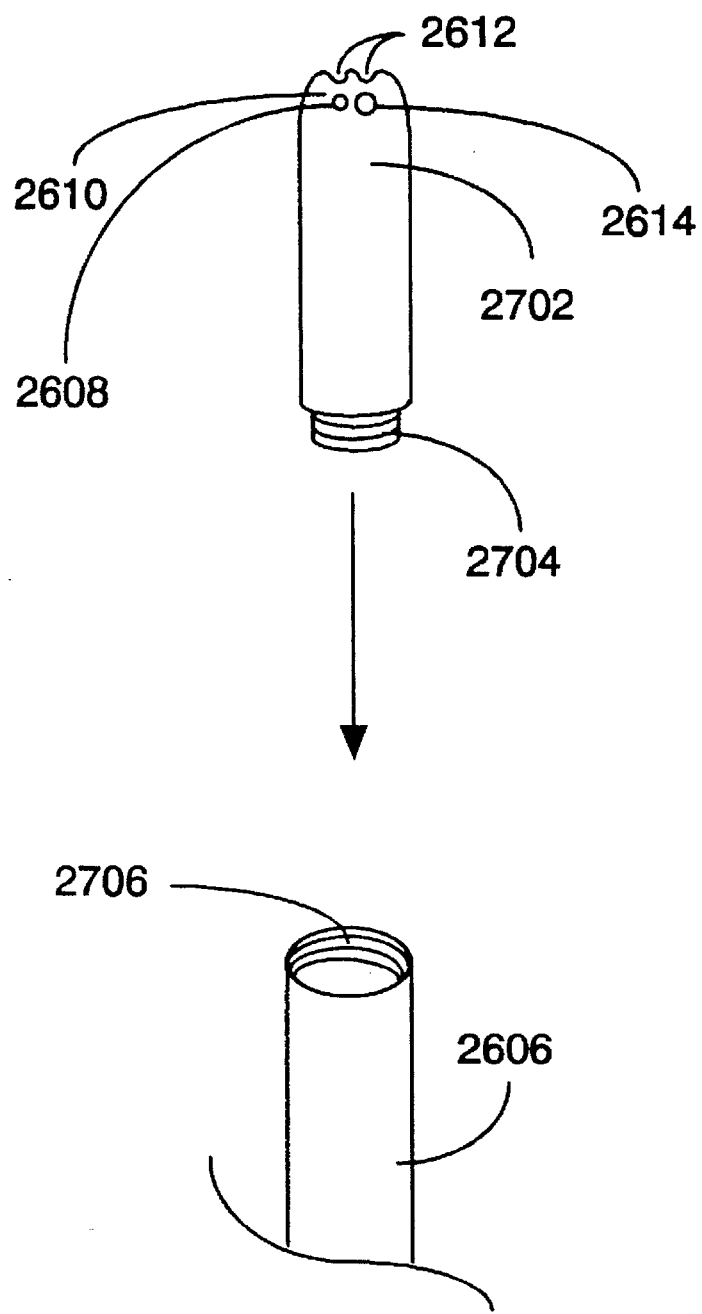
FIG. 27 shows a replaceable spool for use with the embodiment of FIG. 26.

FIG. 27 shows a disposable spool 2702 which can be used on an alternative embodiment of the device shown in FIG. 26. The angled configuration of the distal end described in FIG. 26 is used in FIG. 27 and the portion that projects beyond the remaining distal edge contains the two distal side openings 2608, 2614 and the groove 2612 on the distal edge which were previously described. The pretied knot (not shown) will be discussed in connection with the method used to load the pretied knot on the device.

The proximal end of the spool 2702 has threads 2704 that fit threads 2706 on the distal end of the inner tube 2606 of the reusable devices that use ready made pretied knot sutures and ligatures.

FIG. 28A is a side cross sectional view and FIG. 28B is a bottom view of the inner and outer sleeves 2606, 2604 of the ligature applicator device. The device presented in FIG. 28 can be made with the removable spool 2702 shown in FIG. 27 or with the integral distal end shown in FIG. 26. In the former instance, inner sleeve 2606 has threads that accept the spool 2702 on its distal end. The outer sleeve 2604 is backloaded over the inner sleeve 2606 and has a slidable snug fit on it. The proximal end of the inner sleeve 2606 has a seal 2814 housed within the cap retainer 2822 and the cap 2816. The cap retainer 2822, seal 2814, and cap 2816 are constructed in the same manner as those discussed in previous embodiments.

A pistol shaped handle 2806, 2808, 2810, 2812 is attached distally to inner sleeve 2606 by means of pin 2802 which is in turn attached to distal bar 2806. Distal bar 2806 is hingedly connected via hinge 2808 to proximal bar 2812. Proximal bar 2812 is in turn attached to outer sleeve 2604. Spring 2810 holds the outer sleeve 2604 in the retracted position relative to inner sleeve 2606 when the handle 2806, 2808, 2810, 2812 is not compressed. Those skilled in the art will recognize that alternative handle means other than a spring 2810 may be used such as a spring plate, a wire handle, or a coil spring which may be placed between the finger holder piece 2804 and the proximal handle 2812, and around the outer sleeve 2604.

The pinhole 2820 used to screw the finger holder piece 2804 on the inner sleeve 2606 is also shown. Finger holder piece 2804 and pin 2802 can be a single integral piece. Collar 2830 is used to secure pin 2802. This finger holder piece 2804 is fixedly attached to the inner sleeve 2606 by means of a pin 2802 and provides a fixed point against which proximal bar 2812 can be compressed to advance outer sleeve 2604. This mechanism controls the relative positions of the outer sleeve 2604 and the inner sleeve 2606 because of a slot 2818 in the outer sleeve 2604. More than one pinhole 2820 may be used in a given embodiment and the number of slots 2818 would equal the number of pinholes 2820. For ease of illustration, a single pinhole 2820 is shown on collar 2830. However, a second opposing slot 2818 and pinhole 2820 would provide a more smoothly sliding operating mechanism by balancing pressure on the opposing sides of the device. At a minimum, the length of slot 2818 must equal the length of the distal portion of inner sleeve 2606 which in the non-compressed resting state of the handle extends past the distal end of the outer sleeve 2604. However, those skilled in the art will recognize that the distance the distal end of the outer sleeve 2604 travels past the end of inner sleeve 2606 can vary depending on the length of slot 2818 selected for a particular device. Slot 2818 can be made longer to allow advancing the outer sleeve 604 past the distal end of inner sleeve 2606 and enclose the noose of a loop ligature. In the preferred embodiment, the slot 818 is long enough to allow a surgeon a choice of use as an introducer sleeve for loop ligatures or for use as a pretied knot suture applicator by pushing the pretied knot off of inner sleeve 2606 with outer sleeve 2604.

Shown in FIG. 28A is a suture holder 2824 which is attached to the outside of outer sleeve 2604. The suture holder 2824 has a spring 2826 to hold the tension of the end portion suture under clamp grip 2828 and keep the pretied knot in position at the distal end of the inner tube. The spring 2826 can be implemented in a variety of alternative ways. Those skilled in the art will recognize that any number of suitable methods of clamping or holding sutures may be used in addition to those discussed above in regard to suture holder 2824. Likewise, suture clamp 2824 may be placed on any suitable location, such as proximal handle bar 2812. Therefore, suture holder 2824 should only be considered exemplary of those devices.

Optional extension 2832 allows the surgeon to handle the instrument by holding finger piece 2804 and extension 2832 without accidentally compressing proximal handle bar 2812 and thereby moving the outer sleeve 2604. Optional extension 2832 may also be formed as one piece with cap 2816.

The following illustrates the steps that are necessary to make a pretied knot suture directly on the ligature applier device. The following description also applies to pretied knot ligatures. The reader is referred to FIG. 21, which describes the method used to make the first Lehrer knot (which is the knot used in that illustration) using the standing part suture. A 36 inch suture is preferred. The suture needle is attached to the end of the standing part. The steps are as follows:

A) The end portion is threaded through the distal side opening 2608 or 2614 at the distal end of the inner sleeve from inside the channel 2616 and exits on the outside side surface of the inner sleeve 2606. The end of the suture is held on the suture holder 2824 leaving behind about two thirds of the suture length to maximize the length of the standing part. Place your left index finger alongside the distal end of the device, which points to your left; and hold the standing part with your right hand.

B) Use the standing part to make two loose turns in a counterclockwise direction around the left index finger, the shaft of the device, and the end portion suture that is being held on the instrument. Make a third turn only around the shaft of the instrument and the end portion suture and hold the suture between the tip of the index finger and the shaft of the instrument. Push the first and second loops to the right to remove the loops off the left index finger.

C) Pull the standing part to the left passing the suture needle through the loops. The entire standing part suture with the suture needle attached to its end is thus extended past the distal end of the instrument.

D) Snug the loops and tightly secure the free end of the end portion with the suture holder 2824. The device is now ready to use.

The surgical technique used for pretied knot sutures with the device is as follows. Before introducing the new embodiment of pretied knot applicator device through a cannula, the standing part suture is grasped 1 or 2 cm from the suture needle to introduce it through the laparoscopic cannula, using a needle driver. A size 10 cannula is preferred. The suture needle is then loaded on the needle driver and passed through the target tissues being sutured. The suture needle is then cut off the suture and removed from the body cavity using the same instrument. The removal of the suture needle may be deferred until the ligature has been tied and secured, providing the surgeon is careful not to forget removing the needle. The needle driver is inserted through the ligature applicator device and both instruments are introduced through the laparoscopic cannula to retrieve the standing part and take it out of the body cavity, leaving sufficient suture to form the knot in the proximity of the target tissues. The pretied loops are pushed off the distal end of inner sleeve 2606 by advancing outer sleeve 2604 over it. The surgeon should be careful to close the three loops simultaneously by pulling the end portion through the distal side opening while placing some counter pressure on the noose using the standing part. This results in a slip knot that has a smaller noose than a slip knot that is formed outside of the body cavity.

To close the noose on the target tissues with the standing part, the knot is preferably held on the device by keeping firm tension on the end portion suture to snugly apply the knot against the distal side opening of the instrument. Alternatively, the knot may be held with the distal groove 2612 while applying the distal end of the ligature applicator device against the target tissues.

As discussed previously, after the noose is closed on the target tissues, the slip knot should be cinched with the end portion as the final step in applying the first throw of the ligature. Extracorporeal knots may be applied over the first throw of the ligature to further secure the tie in the manner described previously for the Sure-tie Ligature Application System and in relation to FIGS. 12 and 24. This is possible because the larger size distal side opening allows the ligature applicator device to be used as a knot pusher.

Figure 29A:
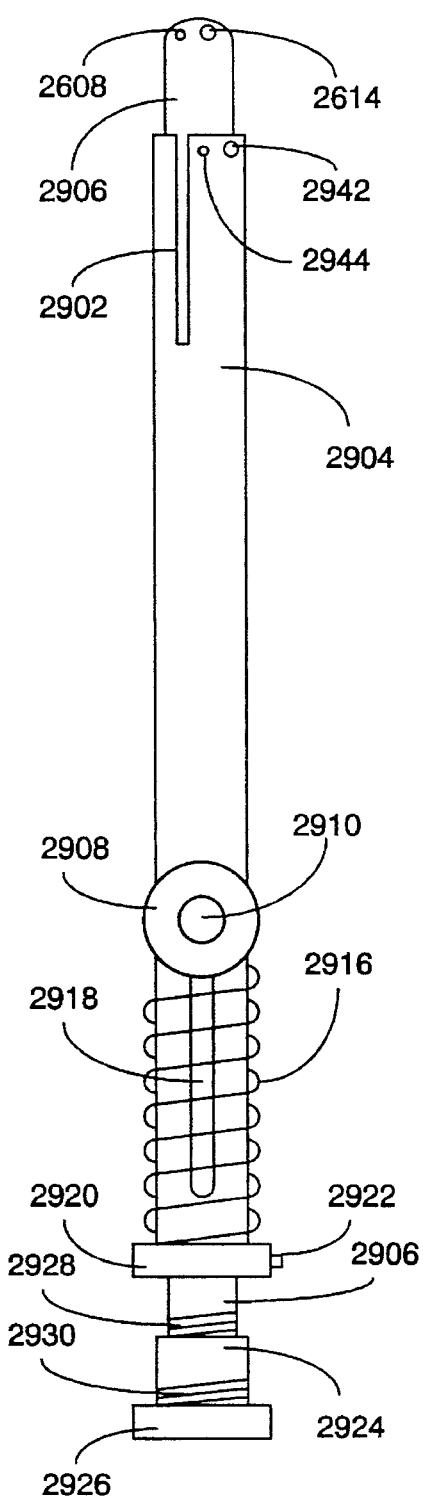

FIG. 29A–E illustrates an alternative embodiment to the device of FIGS. 26–28 which has an improved handle. Referring to FIG. 29A, a top view of the device is shown. Inner sleeve 2906 is similar to inner sleeve 2606 of the previous embodiment. Likewise, side openings 2608, 2614 are equivalent to those discussed above in regard to FIGS. 26–28. In addition to side openings 2608, 2614 in inner sleeve 2906, side openings 2942, 2944 are also included to allow suture strands to be mounted on the distal end of the outer sleeve 2904 in the same fashion. For ease of illustration, rounded grooves 2612 were omitted from FIG. 29, but those skilled in the art will recognize that they can be easily integrated into this embodiment.

Slot 2902 is aligned with side opening 2608 to allow outer sleeve 2904 to be extended past the distal end of inner sleeve 2906 without damaging a suture strand exiting side opening 2608. Outer sleeve 2904 is held in alignment with inner sleeve 2906 by pin 2910 which extends through trigger finger assembly 2908, outer sleeve slot 2918, and into the side of inner sleeve 2906. Pin 2910 can be attached to inner sleeve 2906 by any suitable means, such as pressure fit, threaded attachment, etc. In the preferred embodiment, pin 2910 is threaded at the end and screws into the side of inner sleeve 2906. The length of pin 2910 is selected to allow secure attachment to inner sleeve 2906 without extending into the inner channel of inner sleeve 2906. The reason for this is that the inner channel of inner sleeve 2906 is used by instruments such as graspers, suture scissors, and the like during surgery. If pin 2910 were to extend into the inner channel of inner sleeve 2906, there would be a risk of interference with those other surgical instruments during surgery.

The normal resting state of outer sleeve 2904 is fully retracted as shown in FIG. 29A. Outer sleeve 2904 is pushed toward the proximal end of the device by sleeve spring 2916 which is compressed between trigger finger assembly 2908 and sleeve pusher 2920. During surgery, when the surgeon wishes to push a pretied knot off of the distal end of inner sleeve 2906, sleeve pusher 2920 is pushed forward, compressing sleeve spring 2916 and extending the distal end of outer sleeve 2904 past the end of inner sleeve 2906 thereby pushing the pretied knot off of inner sleeve 2906. Inner sleeve 2906 and outer sleeve 2904 are sized such that inner sleeve 2906 can slidably move within outer sleeve 2904, but snug enough to prevent a suture strand from entering the space between them. Also shown in this embodiment is proximal handle 2926, seal casing 2924 and suture clamp 2922, explained more fully below in the discussion of FIGS. 29 B–E.

Figure 29B:
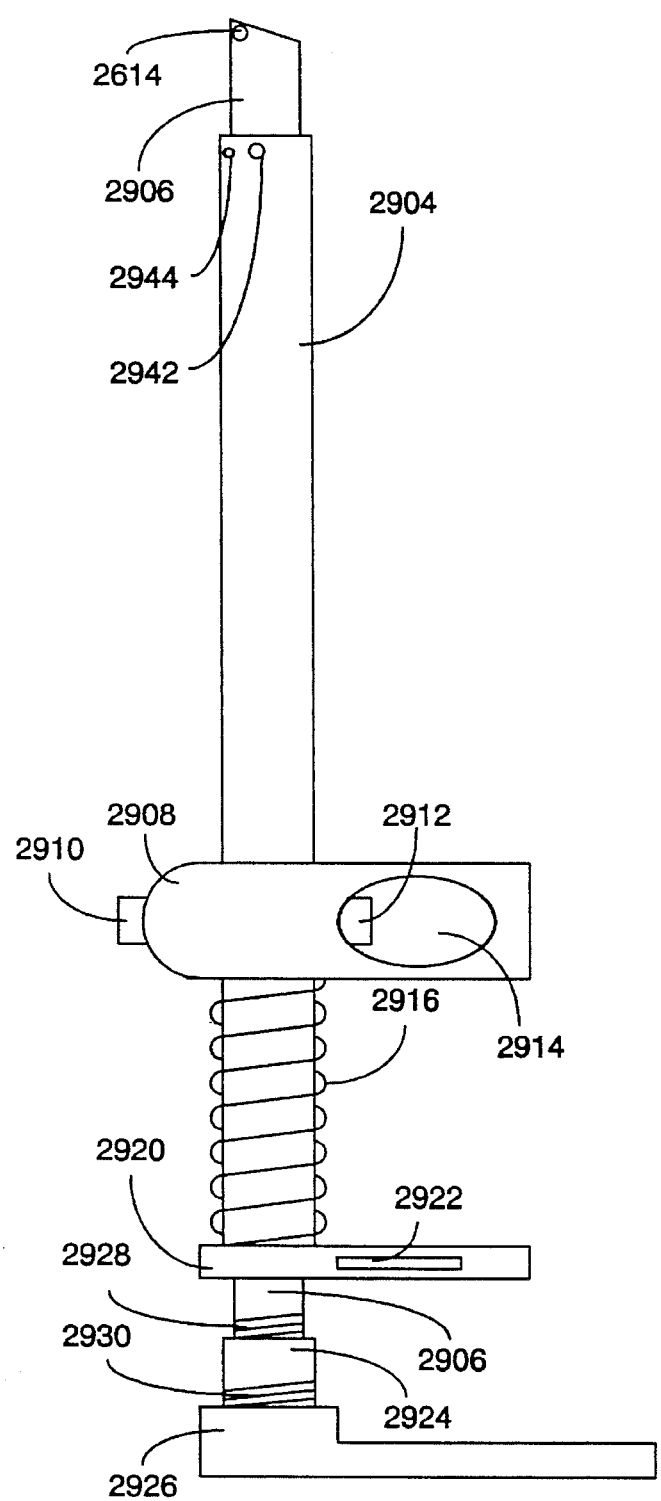
Figure 29A:
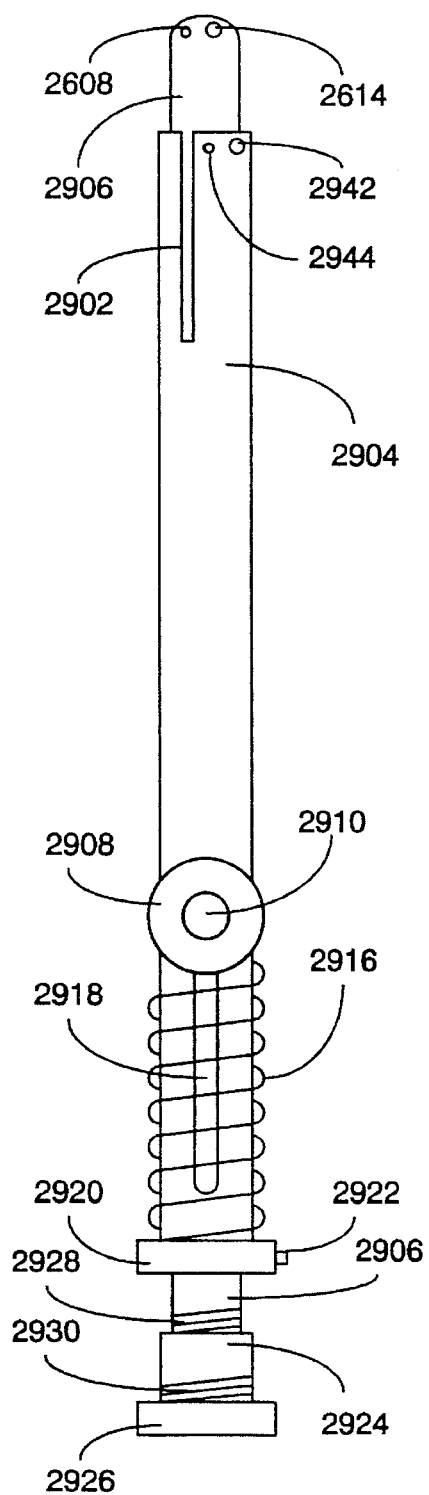
Figure 29B:
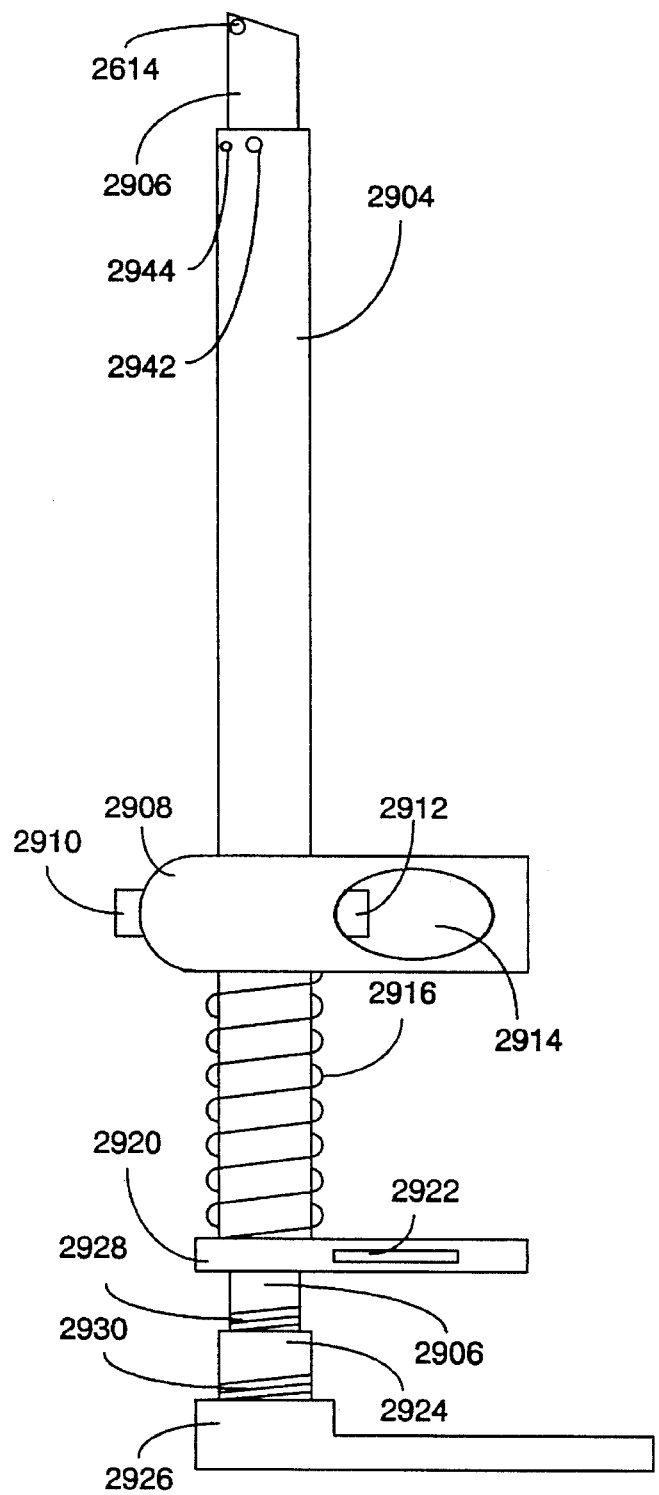

In FIG. 29B, a side view of the device is shown. As can be seen, trigger finger assembly 2908 provides a finger hole 2914 which allows the surgeon to securely grip and control the device during surgery. In addition to pin 2910, discussed above, an additional pin 2912 is shown in this figure to illustrate how multiple pins may be used. As discussed earlier, pins 2910, 2912 do not impinge the internal channel 2618 of inner sleeve 2906. However, they can go through the wall of inner sleeve 2906. In addition, in the preferred embodiment, the pins 2910, 2912 fit snugly into inner sleeve 2906 to prevent pneumoperitoneal gas from escaping. Those skilled in the art will recognize that any suitable number of pins may be used.

Proximal handle 2926 is removably attached via threads 2930 to seal casing 2924. Seal casing 2924 is in turn attached to the proximal end of inner sleeve 2906 via threads 2928. In the preferred embodiments threads 2928, 2930 are used to hold the components together. However, those skilled in the art will recognize that any suitable attachment method may be used, such as pressure fit, adhesives, set screws, etc. may also be used. The screw on method used in the preferred embodiment allows proximal handle 2926 to double as a cap for seal casing 2924. Since proximal handle 2926 and trigger finger assembly 2908 are rigidly attached to inner sleeve 2906, the surgeon can hold the device by proximal handle 2926 and trigger finger assembly 2908 without inadvertantly pushing a pretied knot off of the distal end of the device.

When the surgeon desires to push the pretied knot off of the distal end of inner sleeve 2906, the surgeon's finger only needs to move from the proximal handle 2926 to sleeve pusher 2920 to apply the necessary pressure to unload the pretied knot. Another advantage of the threaded attachment used in the preferred embodiment is that the proximal handle 2926 can be swiveled out of the way of the sleeve pusher for the convenience of the surgeon such that the surgeon can press on the sleeve pusher 2920 with the palm of the hand.

The trigger finger assembly 2908 of FIG. 29 is used for illustrative purposes only. While the illustrated device uses an aperture to facilitate grasping the device, any suitable shape trigger finger assembly can be substituted so long as the device can be conveniently manipulated.

FIG. 29C is a bottom view of the device which shows a second outer sleeve slot 2934. In addition, the bottom of trigger finger assembly 2908 has an aperture 2932 which allows a screw driver to be inserted into trigger finger assembly 2908 to tighten or remove pin 2912.

FIG. 29D is a proximal end view of the device which illustrates how the surgeon may rotate the proximal handle 2926 out of the way to allow the surgeon to press against sleeve pusher 2920. Suture clamp 2922 is shown protruding from the side of sleeve pusher 2920. Suture clamp 2922 is attached to sleeve pusher 2920 via pin 2940. When the surgeon wishes to grasp a suture strand, the suture clamp is pivoted away from sleeve pusher 2920, the suture strand is then placed betwwen sleeve pusher 2920 and suture clamp 2922. Suture clamp 2922 is then pushed back into sleeve pusher 2920 to snugly grasp the suture strand. Those skilled in the art will recognize that the suture clamp 2922 does not have to be located on the sleeve pusher 2920, but can also be placed on any other suitable location in the device so long as it is not in a portion of the device which would be inserted into the body cavity during surgery; and that portion is fixedly attached to outer sleeve 2904, thus loosening the end portion suture while advancing the outer sleeve to push the pretied loops off the inner sleeve 2906.

FIG. 29E shows the device of FIG. 29D with the proximal handle unscrewed and removed. The seal 2936 is shown resting within seal casing 2924. As mentioned above, proximal handle 2926 eliminates the need for a seal retaining cap for seal casing 2924. Seal 2936 is sized to allow a 5 mm instrument such as a suture grasper or suture scissors to slide through the inner channel of inner sleeve 2906.

In the preferred embodiment, a size 10 cannula is used which allows the device to be sized with a 5 mm internal channel. However, those skilled in the art will recognize that the diameter of the device and the cannula used with it can vary to suit a particular application.

The device of FIG. 29 is used in a similar fashion and for the same purposes as discussed in regard to FIGS. 26–28. In addition to the foregoing discussion of the features of FIG. 29, it is also possible and desirable to fit the inner sleeve 2906 of this embodiment with the removable spool discussed above in regard to FIG. 27.

In FIG. 30, an alternative embodiment of the device shown in FIG. 29 is illustrated. In this embodiment, the inner sleeve 2906 is replaced with the solid shaft 1512 of the device shown in FIG. 15. In addition, proximal handle 2926 and sleeve pusher 2920 are merged into a single sleeve pusher handle 3002 with no seal. The shaft 1512 extends out of the proximal end of sleeve pusher handle 3002. In the preferred embodiment, the fit between shaft 1512 is snug enough to allow shaft 1512 to slide inside outer sleeve 2904, but also snug enough to substantially prevent pneuroperitoneal gas from escaping between the shaft 1512 and outer sleeve 3002. An O-ring (not shown) placed at an appropriate location on shaft 1512 may also be used to prevent gas from escaping if necessary. No seal 2936 is used on the preferred embodiment. In this embodiment, since the shaft is solid, a single pin may be used to penetrate the shaft 1512 either partially or completely through. Thus, pins 2910, 2912 can be two separate pins or a single pin which travels entirely through the diameter of the shaft 1512. Of course, two opposing slots 2918, 2934 are required to accommodate a pin traveling through the shaft 1512 to allow the outer sleeve 2904 to slide past the pins.

In this embodiment, a smaller cannula can be used since the shaft 1512 does not have an internal channel sized like the internal channel of FIG. 29. Therefore, the preferred embodiment fits through a size 5 cannula, leaving space for at least one suture to travel from the distal end of the instrument to the outside of the body cavity. The handle described allows a single hand operation of the device which can be used for pretied knot sutures, pretied knot ligatures, and loop ligatures. As in the embodiment of FIG. 29, the length of slots 2918, 2934 determined the distance the outer sleeve 2904 is allowed to advance past the distal end of shaft 1512 and can be used to enclose the noose of a loop ligature in preparation for introducing it through the cannula and also can be used to push the pretied loops of the knot off the distal end of shaft 1512.

An advantage of the embodiment of FIG. 30 is that the shaft 1512 can be either reusable or disposable. In addition, a reusable shaft can be used in conjunction with a disposable spool similar to that discussed above in the other embodiments to allow quick replacement of loop ligatures or pretied knots for suture ligatures or tie ligatures.

In use, suture strands and the guide wire 1408 (shown in FIG. 15) from side openings 1516, 1518 will fit in slot 2902 in the same manner as suture strands discussed above in regard to FIG. 29A–E. The sutures exit between the outer sleeve 2904 and the cannula (not shown).

While the invention has been described with respect to a preferred embodiment thereof, it will be understood by those skilled in the art that various changes in detail my be made therein without departing from the spirit, scope, and teaching of the invention. For example, numerous small variations can be made on the mechanism employed to accomplish a rotating sheath, wire loops can be used to assist in loading ligatures, a variety of materials can be used to fabricate the seal of the introducer sleeve, etc. Likewise, the spool can have many variations so long as it allows the pretied loops of the knot to be transferred to the standing part suture by the surgeon. Accordingly, the invention herein disclosed is to be limited only as specified in the following claims.

I claim:

1. A ligator device for extracorporeally manipulating the ends two suture strands of a slip knot and pushing hitch knots, comprising:
an internal/inner sleeve having a proximal end and a distal end, the internal sleeve having at least one side aperture at its distal end sized such that at least one suture strand is slidably inserted into the side aperture;
an external/outer sleeve having a proximal end and a distal end, the external sleeve further having an inner diameter sized to slidably accept the internal sleeve; and
extension means to slidably move the external sleeve a predetermined distance range over the internal sleeve such that the distal end of the external sleeve is advanced over the internal sleeve or extended past the internal sleeve.

2. A device, as in claim 1, further comprising:
a side slot in the external sleeve having a proximal end and a distal end, the side slot providing a path in the side of the external sleeve oriented approximately from the proximal end to the distal end of the external sleeve;
handle means attached at a first end to the side of the inner sleeve and extending from the side of the inner sleeve through the side slot of the outer sleeve, the handle means attached at a second end to the outer sleeve, the handle means further having a hinge to allow compression of the handle such that the distance between the first and second end is selectably altered to move the outer sleeve over the inner sleeve.

3. A device, as in claim 2, wherein:
the handle means further comprises:
a retaining pin attached to the inner sleeve and passing through the side slot in the outer sleeve;
a distal handle bar attached at a first end to the retaining pin and at a second end to hinge means;
a proximal handle bar attached at a first end to the hinge means and at a second end to the outer sleeve;
spring means between the first and second handle bar means to hold the first and second handle bar means in a predetermined position when the spring means is not compressed; and
means in the inner sleeve to attach to the retaining pin.

4. A device, as in claim 3, further comprising suture clamp means attached to the outer sleeve, the suture clamp means capable of removably holding s suture strand extending from the side aperture.

5. A device, as in claim 2, further comprising suture clamp means attached to the outer sleeve, the suture clamp means capable of removably holding a suture strand extending from the side aperture.

6. A device, as in claim 3, further comprising:
a removable spool removably attached to the distal end of the inner sleeve and in which the side aperture is located on the distal end of the removable spool; and
a pretied ligature, pretied knot suture, or loop ligature mounted on the removable spool.

7. A device, as in claim 2, further comprising:
a removable spool removably attached to the distal end of the internal sleeve and in which the side aperture is located on the distal end of the removable spool; and
a pretied ligature mounted on the removable spool.

8. A device, as in claim 7, wherein the distal end of the inner sleeve includes a groove having a diameter suitable to accommodate a suture strand.

9. A device, as in claim 1, wherein the extension means further comprises:
a trigger finger assembly attached to the internal sleeve;
a proximal handle attached to the proximal end of the internal sleeve;
a sleeve pusher attached to the proximal end of the external sleeve; and
retraction means attached to the sleeve pusher which holds the external sleeve toward the proximal end of the device when in the resting state.

10. A device, as in claim 9, wherein the retraction means further comprise a spring which is compressibly attached to the trigger finger assembly and the sleeve pusher.

11. A device, as in claim 10, wherein the proximal handle is rotatably attached to the device such that the proximal handle can rotate in at least one direction away from the direction of the sleeve pusher.

12. A device, as in claim 11, further comprising:
at least one slot in the distal end of the external sleeve, the slot aligned with at least one side aperture in the internal sleeve; and
at least one pin extending from outside of the external sleeve, through the slot in the side of the external sleeve and attached to the internal sleeve such that rotational movement of the external sleeve about the internal sleeve is restricted.

13. A device, as in claim 12, further comprising a suture clamp, attached to the device at a proximal location such that the clamp would remain outside of the body cavity during surgery.

14. A device, as in claim 13, wherein the suture clamp is attached to the sleeve pusher.

15. A device, as in claim 13, wherein the suture clamp is attached to the outer sleeve.

16. A device, as in claim 13, wherein the external sleeve has at least one external sleeve side aperture at its distal end sized such that at least one suture strand is slidably inserted into the external sleeve side aperture.

17. A device, as in claim 13, further comprising:
a removable spool removably attached to the distal end of the inner sleeve and in which the side aperture is located on the distal end of the removable spool; and
a pretied ligature, pretied knot suture, or loop ligature mounted on the removable spool.

18. A ligator device for extracorporeally manipulating the ends two suture strands of a slip knot and pushing hitch knots, comprising:

a substantially solid internal shaft having a proximal end and a distal end, the internal shaft having an internal channel at the distal end which connects a distal aperture with at least one side aperture at its distal end sized such that at least one suture strand is slidably inserted into the side aperture;

an external sleeve having a proximal end and a distal end, the external sleeve further having an inner diameter sized to slidably accept the internal shaft; and extension means to slidably move the external sleeve a predetermined distance range over the internal shaft such that the distal end of the external sleeve can be advanced over the internal shaft or extended past the internal shaft.

19. A device, as in claim 18, wherein: the extension means further comprises:

a trigger finger assembly attached to the shaft via a pin inserted through a slot in the external sleeve;

a sleeve pusher attached to the proximal end of the external sleeve; and a spring compressibly attached to the trigger finger assembly and the sleeve pusher.

20. A device, as in claim 19, further comprising:

a removable spool removably attached to the distal end of the internal shaft and in which the side aperture is located on the distal end of the removable spool; and a pretied ligature, pretied knot suture, or loop ligature mounted on the removable spool.

* * * * *